United States Patent
Liotta et al.

(10) Patent No.: US 11,649,235 B2
(45) Date of Patent: May 16, 2023

(54) PAN-TROPIC ENTRY INHIBITORS

(71) Applicant: Emory University, Atlanta, GA (US)

(72) Inventors: Dennis Liotta, Atlanta, GA (US); Edgars Jecs, Decatur, GA (US); Yesim Altas Tahirovic, Decatur, GA (US); Lawrence Wilson, Chamblee, GA (US); Stephen Pelly, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/040,026

(22) PCT Filed: Mar. 19, 2019

(86) PCT No.: PCT/US2019/023022
§ 371 (c)(1),
(2) Date: Sep. 21, 2020

(87) PCT Pub. No.: WO2019/183133
PCT Pub. Date: Sep. 26, 2019

(65) Prior Publication Data
US 2021/0017178 A1   Jan. 21, 2021

Related U.S. Application Data

(60) Provisional application No. 62/644,982, filed on Mar. 19, 2018.

(51) Int. Cl.
| | | |
|---|---|---|
| *C07D 403/12* | (2006.01) | |
| *A61K 31/496* | (2006.01) | |
| *C07D 471/08* | (2006.01) | |
| *C07D 401/04* | (2006.01) | |
| *C07D 401/14* | (2006.01) | |
| *C07D 405/14* | (2006.01) | |

(52) U.S. Cl.
CPC ......... *C07D 471/08* (2013.01); *C07D 401/04* (2013.01); *C07D 401/14* (2013.01); *C07D 405/14* (2013.01)

(58) Field of Classification Search
CPC .. C07D 403/12; C07D 401/12; C07D 241/38; A61K 31/496; A61K 31/4995; A61P 31/18; A61P 35/00
USPC ....... 544/363, 360, 349; 514/253.06, 253.01, 514/249
See application file for complete search history.

(56) References Cited

U.S. PATENT DOCUMENTS

| | | |
|---|---|---|
| 7,354,934 B2 | 4/2008 | Bridger |
| 7,863,293 B2 | 1/2011 | Bridger et al. |
| 8,008,312 B2 | 8/2011 | Shim |
| 8,969,381 B2 * | 3/2015 | Wilson ............ A61K 31/4709 514/312 |
| 9,545,403 B2 | 1/2017 | Wilson |
| 10,016,408 B2 | 2/2018 | Wilson |
| 2010/0280010 A1 | 11/2010 | Gudmundsson et al. |
| 2011/0274651 A1 | 11/2011 | Acuff |

FOREIGN PATENT DOCUMENTS

| | | |
|---|---|---|
| CN | 102675305 | 11/2014 |
| CN | 103570683 | 4/2018 |
| WO | 2003084954 | 10/2003 |

(Continued)

OTHER PUBLICATIONS

Åhman, et al., Process Research and Scale-up of a Commercialisable Route to Maraviroc (UK-427,857), a CCR-5 Receptor Antagonist, Org Proc Res Dev, 2008, 12(6), 1104-1113.

(Continued)

*Primary Examiner* — Charanjit Aulakh
(74) *Attorney, Agent, or Firm* — Emory Patent Group

(57) ABSTRACT

This disclosure relates to compounds according to Formula (I), salts, prodrugs and pharmaceutical formulation comprising the compound are provided herein for the treatment of CXCR4 and CCR5 related conditions. The conditions may include viral infections, abnormal cellular proliferation, retinal degeneration and inflammatory diseases, or the compounds may be used as immunostimulants or immunosuppressants. Furthermore, the compounds may be used in combination with another active ingredient selected from an antiviral agent or chemotherapeutic agent.

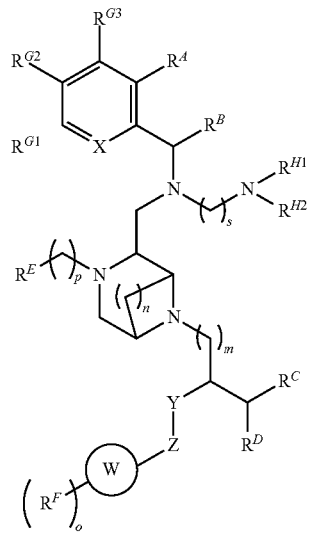

Formula (I)

12 Claims, 2 Drawing Sheets

(56) References Cited

FOREIGN PATENT DOCUMENTS

| WO | 20060020415 | 2/2006 |
|---|---|---|
| WO | 2006023400 | 3/2006 |
| WO | 2006026703 | 3/2006 |
| WO | 2007027999 | 3/2007 |
| WO | 2007087548 | 8/2007 |
| WO | 2007087549 | 8/2007 |
| WO | 2009121063 | 10/2009 |
| WO | 2012075362 | 6/2012 |
| WO | 2017011517 | 1/2017 |
| WO | 2017106291 | 6/2017 |
| WO | 2017223239 | 12/2017 |
| WO | 2017223243 | 12/2017 |
| WO | 2018156595 | 8/2018 |
| WO | 2019060860 | 3/2019 |

OTHER PUBLICATIONS

Armour, et al., The discovery of tropane-derived CCR5 receptor antagonists, Chem Biol Drug Des, 2006, 67(4), 305-308.

Balabanian, et al., CXCR4-tropic HIV-1 envelope glycoprotein functions as a viral chemokine in unstimulated primary CD4+ T lymphocytes, J Immun, 2004, 173(12), 7150-7160.

Briz, et al., HIV entry inhibitors: mechanisms of action and resistance pathways, J Antimicrob Chemother, 2006, 57(4), 619-627.

Cameron, et al., Establishment of HIV-1 latency in resting CD4+ T cells depends on chemokine-induced changes in the actin cytoskeleton, PNAS USA, 2010, 107(39), 16934-16939.

Catalano, et al., Synthesis of a Novel Tricyclic 1,2,3,4,4a,5,6,10b-Octahydro-1,10-Phenanthroline Ring System and CXCR4 Antagonists with Potent Activity Against HIV-1, Bioorg. Med. Chem. Lett., 2010, 20, 2186-2190.

Crane, et al., CXCR4 Receptor Expression on Human Retinal Pigment Epithelial Cells from the Blood-Retina Barrier Leads to Chemokine Secretion and Migration in Response to Stromal Cell-Derived Factor 1α, J. Immunol., 2000, 165, 4372-4278.

Debnath, et al., Small Molecule Inhibitors of CXCR4, Theranostics, 2013, 3(1), 47-75.

Dwinell, et al., Chemokine receptor expression by human intestinal epithelial cells, Gastroenterology, 1999, 117, 359-367.

Gouwy, et al., CXCR4 and CCR5 ligands cooperate in monocyte and lymphocyte migration and in inhibition of dual-tropic (R5/X4) HIV-1 infection, Eur J Immun, 2011, 41(4), 963-973.

Gudmundsson, et al., Amine Substituted N-(1H-Benzimidazol-2ylmethyl)-5,6,7,8-Tetrahydro-8-Quinolinamines as CXCR4 Antagonists with Potent Activity against HIV-1, Bioorg. Med. Chem. Lett., 2009, 19, 5048-5052.

Gudmundsson, et al., Imidazopyridine-5,6,7,8-tetrahydro-8-quinolinamine derivatives with potent activity against HIV-1, Bioorg. Med. Chem. Lett., 2009, 19, 6399-6403.

Gupta, et al., Chemokine receptors in human endothelial cells. Functional expression of CXCR4 and its transcriptional regulation by inflammatory cytokines, J Biol Chem., 1998, 273, 4282-4287.

Haycock-Lewandowski, et al., Development of a Bulk Enabling Route to Maraviroc (UK-427,857), a CCR-5 Receptor Antagonist, Organic Process Research & Development, 2008, 12, 1094-1103.

Jecs, et al., Synthesis of Novel Tetrahydroisoquinoline CXCR4 Antagonists with Rigidified Side-Chains, ACS Med. Chem. Lett., 2018, 9(2), 89-93.

Jenkinson, et al., Blockade of X4-Tropic HIV-1 Cellular Entry by GSK812397, a Potent Noncompetitive CXCR4 Receptor Antagonist, Antimicrob Agents Chemother, 2010, 54(2), 817-824.

Kang, et al., A multigenic program mediating breast cancer metastasis to bone, Cancer Cell, 2003, 3, 537-549.

Li, et al., Design, Synthesis, and Structure-Activity-Relationship of a Novel Series of CXCR4 Antagonists, Eur. J. Med. Chem., 2018, 149, 30-44.

Li, et al., Design, Synthesis, and Evaluation of Pyrrolidine Based CXCR4 Antagonists with in Vivo Anti-Tumor Metastatic Activity, Eur. J. Med. Chem., 2020, 205, 112537.

Lin, et al., Design, Synthesis, and Evaluation of Novel CXCR4 Antagonists Based on an Aminoquinoline Template, Bioorg. Chem., 2020, 99, 103824.

Lin, et al., Design, Synthesis, and Characterization of Novel CXCR4 Antagonists Featuring Cyclic Amines, ChemMedChem, 2020, 15, 1150-1162.

Mellors, et al., In vitro selection and molecular characterization of human immunodeficiency virus-1 resistant to non-nucleoside inhibitors of reverse transcriptase, Mol Pharma, 1992, 41(3), 446-451.

Miller, et al., Novel N-Substituted Benzimidazole CXCR4 Antagonists as Potential Anti-HIV Agents, Bioorg. Med. Chem. Lett., 2010, 20, 2125-2128.

Miller, et al., Synthesis and SAR of Novel Isoquinoline CXCR4 Antagonists with Potent Anti-HIV Activity, Bioorg. Med. Chem. Lett., 2010, 20, 30263030.

Miller, et al., Discovery of Tetrahydroisoquinoline-Containing CXCR4 Antagonists with Improved in Vitro ADMET Properties, J. Med. Chem., 2018, 61, 946-979.

Mitra, et al., CXCR4 mRNA expression in colon, esophageal and gastric cancers and hepatitis C infected liver, Int J Oncol, 1999, 14, 917-925.

Moyle, et al., Proof of activity with AMD11070, an orally bioavailable inhibitor of CXCR4-tropic HIV type 1, Clin Inf Diseases, 2009, 48(6), 798-805.

Muller, et al., Involvement of chemokine receptors in breast cancer metastasis, Nature, 2001, 410, 50-56.

Murdoch, et al., Functional expression of chemokine receptor CXCR4 on human epithelial cells, Immunology, 1998, 98(1), 36-41.

Nguyen, et al., Design, Synthesis, and Pharmacological Evaluation of Second-Generation Tetrahydroisoquinoline-Based CXCR4 Antagonists with Favorable ADME Properties, J. Med. Chem. 2018, 61, 7168-7188.

Peng, et al., The Chemical Diversity and Structure-Based Evolution of Non-Peptide CXCR4 Antagonists with Diverse Therapeutic Potential, Eur. J. Med. Chem., 2018, 149, 148-169.

Rossetti, et al., Virological and Immunological Response to Antiretroviral Regimens Containing Maraviroc in HIV Type 1-Infected Patients in Clinical Practice: Role of Different Tropism Testing Results and of Concomitant Treatments, AIDS Res Human Retroviruses, 2014, 30(1), 17-24.

Skerlj, et al., Synthesis and SAR of Novel CXCR4 Antagonists That Are Potent Inhibitors of T-Tropic (X4) HIV-1 Replication, Bioorg. Med. Chem. Lett., 2011, 21, 1414-1418.

Skerlj, et al., Discovery of Novel Small Molecule Orally Bioavailable C-X-C Chemokine Receptor 4 Antagonists That Are Potent Inhibitors of T-Tropic (X4) HIV-1 Replication, J. Med. Chem., 2010, 53(8), 3376-3388.

Staller, et al., Chemokine receptor CXCR4 downregulated by von Hippel-Lindau tumour suppressor pVHL, Nature, 2003, 425, 307-311.

Tagat, et al., Piperazine-Based CCR5 Antagonists as HIV-1 Inhibitors. IV. Discovery of 1-[(4,6-Dimethyl-5-pyrimidinyl) carbonyl]-4-[4-{2-methoxy-1(R)-4-(Lifluoromethyl)phenyl}ethyl-3(S)-methyl-1-piperazinyl]-4-methylpiperidine (Sch-417690/Sch-D), a Potent, Highly Selective, and Orally Bioavailable CCR5 Antagonist, J Med Chem, 2004, 47(10), 2405-2408.

Tahirovic, et al., Discovery of N-Alkyl Piperazine Side Chain Based CXCR4 Antagonists with Improved Drug-like Properties, ACS Med. Chem. Lett., 2018, 9, 446-451.

Tahirovic, et al., Small Molecule and Peptide-Based CXCR4 Modulators as Therapeutic Agents. A Patent Review for the Period from 2010 to 2018, Expert Opin. Ther. Pat., 2020, 30(2), 87-101.

Truax, et al., Discovery of Tetrahydroisoquinoline-Based CXCR4 Antagonists, ACS Med. Chem. Lett., 2013, 4, 1025-1030.

Volin, et al., Chemokine Receptor CXCR4 Expression in Endothelium, Biochem Biophys Res Commnun, 1998, 242, 46-53.

Wald, et al., Involvement of the CXCL12/CXCR4 pathway in the advanced liver disease that is associated with hepatitis C virus or hepatitis B virus, Eur J Immun, 2004, 34(4), 1164-1174.

Wilson, et al., Synthesis and SAR of 1,2,3,4-Tetrahydroisoquinoline-Based CXCR4 Antagonists, ACS Med. Chem. Lett., 2018, 9, 17-22.

Wu, et al., Chemokine Coreceptor Signaling in HIV-1 Infection and Pathogenesis, PLoS Pathogens, 2009, 5(12).

(56) References Cited

OTHER PUBLICATIONS

Zhang, et al., Discovery of non-peptide small molecular CXCR4 antagonists as anti-HIV agents: Recent advances and future opportunities, European Journal of Medicinal Chemistry, 114, 2016, 65-78.

Zhao, et al., Discovery of Novel N-Aryl Piperazine CXCR4 Antagonists, Bioorg. Med. Chem. Lett., 2015, 25, 4950-4955.

Zhu, et al., Structural Optimization of Aminopyrimidine-Based CXCR4 Antagonists, Eur. J. Med. Chem., 2020, 187, 111914.

* cited by examiner

PAN-TROPIC ENTRY INHIBITORS

CROSS REFERENCE TO RELATED APPLICATIONS

This application is the National Stage of International Application No. PCT/US2019/023022, which claims the benefit of U.S. Provisional Application No. 62/644,982 filed Mar. 19, 2018. The entirety of each of these applications is hereby incorporated by reference for all purposes.

TECHNICAL FIELD

The present disclosure relates to pan-tropic entry inhibitors, and in particular, to chemokine CXCR4 and CCR5 receptor modulators and uses related thereto. In certain embodiments, the disclosure relates to pharmaceutical compositions comprising compounds disclosed herein, derivatives, or pharmaceutically acceptable salts or prodrugs thereof. In certain embodiments, the compositions disclosed herein are used for managing CXCR4 and CCR5 related conditions, typically prevention or treatment of viral infections such as HIV or for managing cancer.

BACKGROUND

As of July 2017, approximately 21 million of the estimated 37 million people worldwide living with HIV/AIDS have access to antiretroviral therapy (ART). While this represents a significant improvement from 2010, when only 7.5 million individuals had access to ART, it still means that over 40% of HIV-positive individuals around the world remain without access to therapy. Moreover, in many parts of the world, economic considerations preclude the use of the more effective current generation of HIV therapeutics, which are clearly superior to early generation drugs. Thus, a need exists for new anti-HIV agents that can: (i) simplify dosing schedules, (ii) reduce pill burden and (iii) expand the utility of existing drugs through new combinations that significantly delay the onset of resistance. In vitro resistance studies conducted with entry inhibitors TAK-779 (a CCR5 antagonist) and AMD3100 required significantly more passages to develop resistance (41 and 63, respectively) when compared to the anti-HIV agents, AZT and nevirapine (11 and 2 passages, respectively), both of which target HIV reverse transcriptase (RT) (Balabanian et al., *J Immun*, 2004, 173(12); Cameron et al., *PNAS USA*, 2010, 107 (39); Mellors et al., *Mol Pharma*, 1992, 41(3); Wu et al., *PLoS Pathogens*, 2009, 5(12)).

Gouwy et al. first demonstrated a synergistic effect with CCL5 and CXCL12 (the cognate ligands of CCR5 and CXCR4, respectively) against viral replication in cell cultures infected with dual-tropic HIV. The study also showed that a combination of the CXCR4 antagonist, AMD3100 and the CCR5 antagonist, Maraviroc synergistically enhanced potency against dual-tropic strains. Since the chemokine entry inhibitor, Maraviroc, only blocks entry of the M-tropic virus, its extended use leads to selection of the more virulent dual M/T-tropic and T-tropic strains of the virus (Gouwy et al., *Eur J Immun*, 2011, 41(4); Rossetti et al., *AIDS Res Human Retroviruses*, 2014, 30(1)), followed by a rapid decline in health. Administration of AMD11070 (a CXCR4 antagonist) results in a tropism shift in some mixed-tropic patients (Moyle et al., *Clin Inf Diseases*, 2009, 48(6)) and long-term exposure in animals has been linked to toxicity.

Studies have shown that CXCR4 interactions also regulate the migration of metastatic cells. Hypoxia, a reduction in partial oxygen pressure, is a micro-environmental change that occurs in most solid tumors and is a major inducer of tumor angiogenesis and therapeutic resistance. Hypoxia increases CXCR4 levels (Staller, et al. (2003) *Nature* 425: 307-311). Microarray analysis on a sub-population of cells from a bone metastatic model with elevated metastatic activity showed that one of the genes increased in the metastatic phenotype was CXCR4. Furthermore, over-expression of CXCR4 in isolated cells significantly increased the metastatic activity (Kang, et al. (2003) *Cancer Cell* 3: 537-549). In samples collected from various breast cancer patients, Muller et al. (Muller, et al. (2001) *Nature* 410: 50-56) found that CXCR4 expression levels are higher in primary tumors relative to normal mammary gland or epithelial cells. These results suggest that the expression of CXCR4 on cancer cell surfaces may direct the cancer cells to sites that express high levels of SDF-1. Consistent with this hypothesis, SDF-1 is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs.

In addition to regulating migration of cancer cells, CXCR4-SDF-1 interactions may regulate vascularization necessary for metastasis. Blocking either CXCR4/SDF-1 interaction or the major G-protein of CXCR4/SDF-1 signaling pathway ($G_{\alpha i}$) inhibits VEGF-dependent neovascularization. These results indicate that SDF-1/CXCR4 controls VEGF signaling systems that are regulators of endothelial cell morphogenesis and angiogenesis. Numerous studies have shown that VEGF and MMPs actively contribute to cancer progression and metastasis.

Thus, there is a need to identify CXCR4 and/or CCR5 antagonists for therapeutic applications in treating or preventing cancer and a need for new entry inhibitors to alleviate some of the abovementioned problems, to some extent at least.

SUMMARY

According to a first embodiment of the present disclosure there is provided a compound according to Formula (I) or salt thereof,

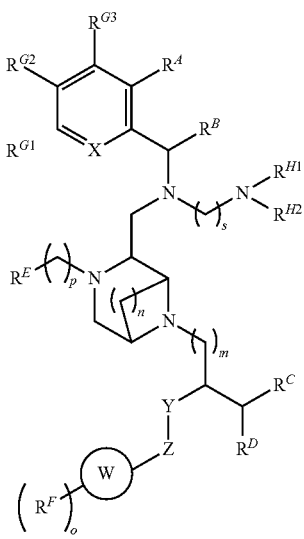

Formula (I)

wherein $R^A$, $R^B$, $R^C$ and $R^D$ are individually and independently H, aryl or a C1 to C4 alkyl which may be straight, branched, saturated or unsaturated, or $R^A$ and $R^B$, together with the atoms to which they are attached, or $R^C$ and $R^D$, together with the atoms to which they are attached, may be connected to form a carbocyle, heterocarbocyle aryl or heteroaryl, and $R^A$, $R^B$, $R^C$ and $R^D$ may be individually and independently optionally substituted with R; $R^E$, $R^{G1}$, $R^{G2}$, $R^{G3}$, $R^{H1}$ and $R^{H2}$ are each individually and independently selected from an H, alkyl, carbocycle, heterocarbocycle, aryl or heteroaryl, each of which may be optionally substituted with Rx; Ring W is a carbocyle, heterocarbocyle aryl or heteroaryl which is substituted with one or more RF groups, where o is 0, 1, 2, 3 or 4 or ring W is absent; RF is a chloro, fluoro, bromo, iodo, C1 to C3 alkyl, trifluoromethyl, O; X is a N or a CH; Y is NH when Z is CO and Y is CO when Z is NH or Y and Z are absent; n, m and p are each independently 0, 1 or 2; s is 1, 2, 3, 4 or 5; and Rx is a halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Further features provide for the compounds of Formula (I) to be Formula (IA) or salts thereof, Formula (IA)

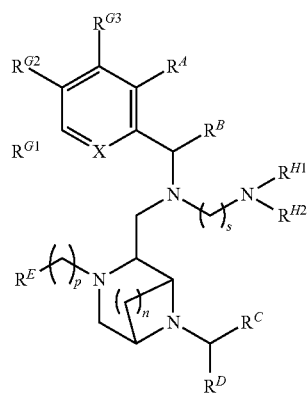

wherein $R^A$, $R^B$, $R^C$, $R^D$, $R^E$, $R^{G1}$, $R^{G2}$, $R^{G3}$, $R^{H1}$ and $R^{H2}$, X, p, n and s are as defined above is an H, alkyl, carbocycle, heterocarbocycle, aryl or heteroaryl, each of which may be optionally substituted with Rx.

Some exemplary compounds of Formula (I) are selected from the following list:

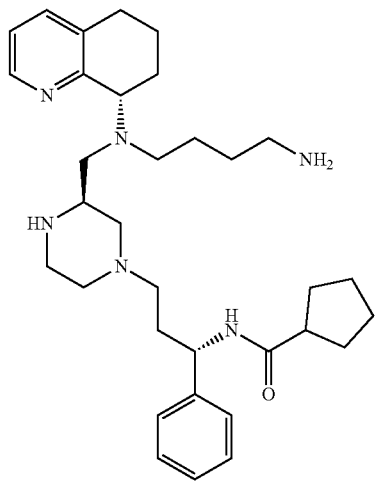

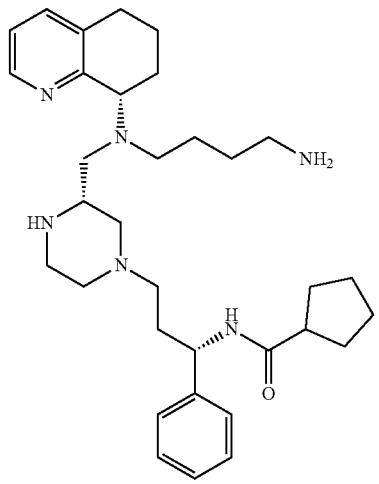

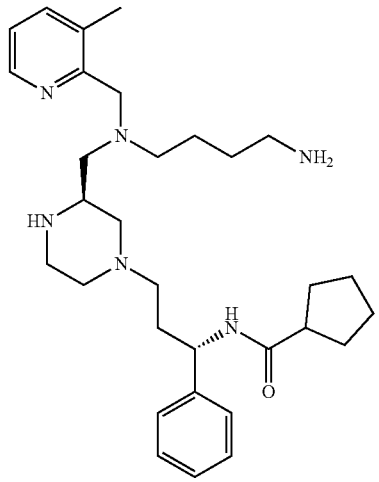

5
-continued
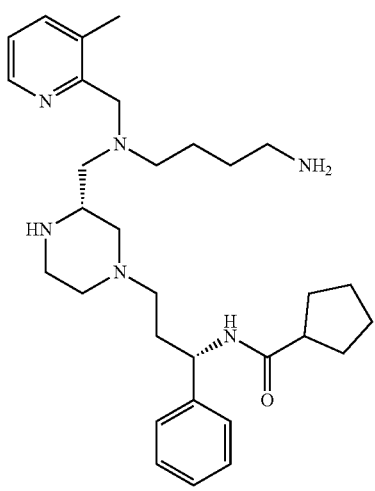
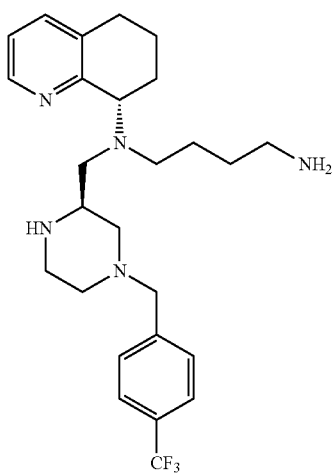
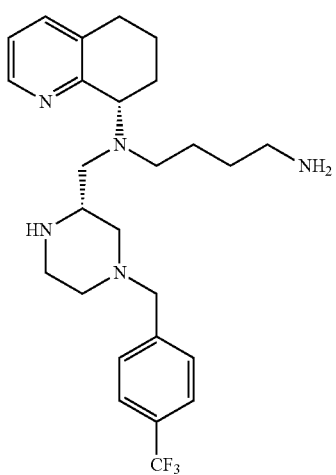
6
-continued
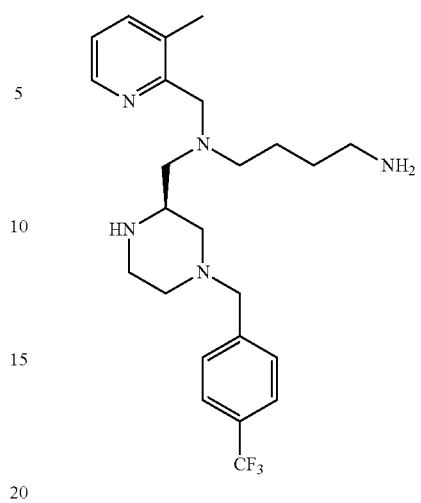
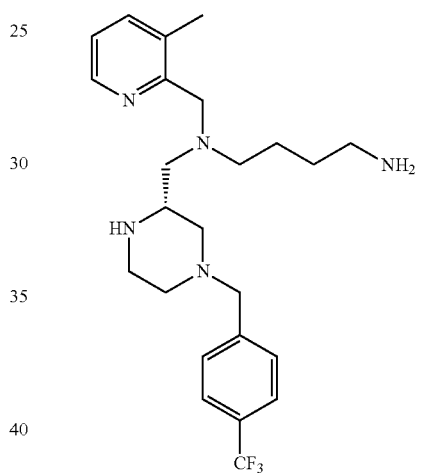
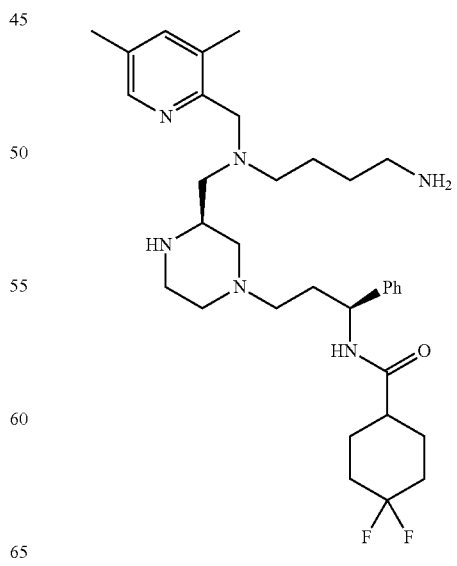

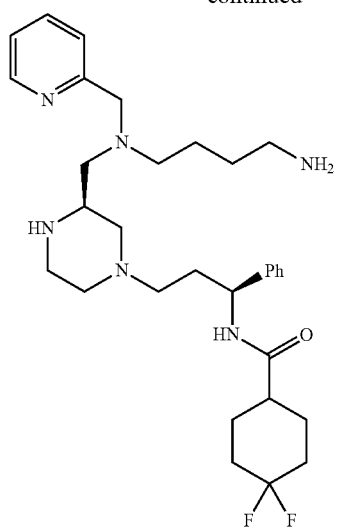
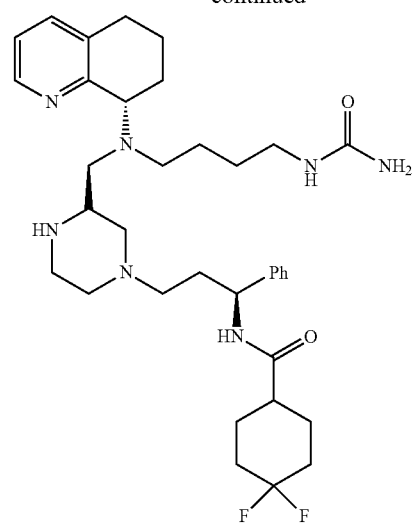
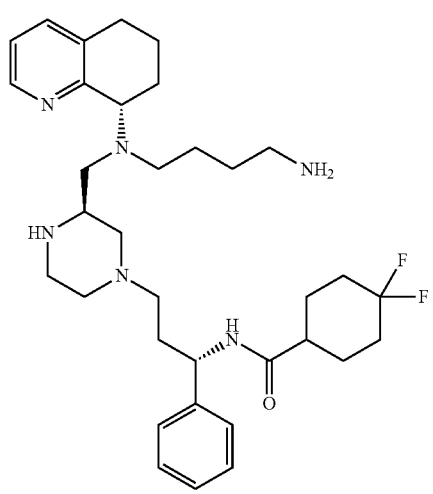
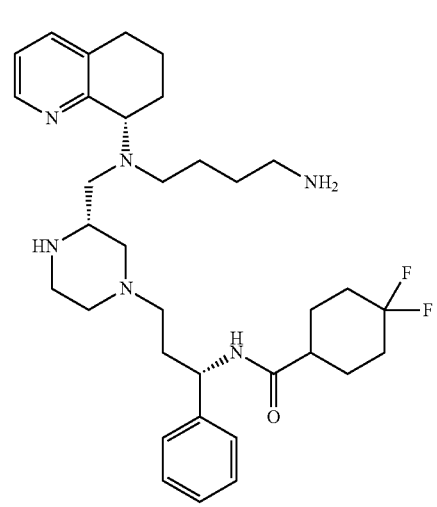
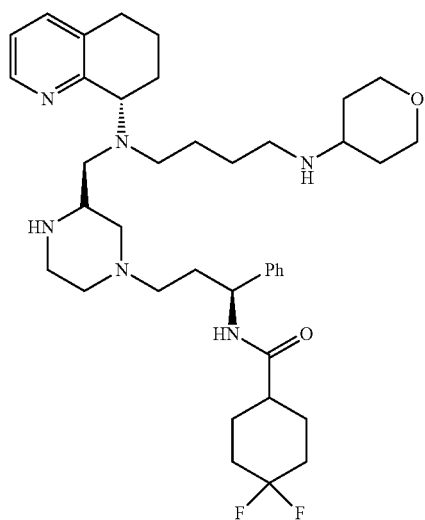
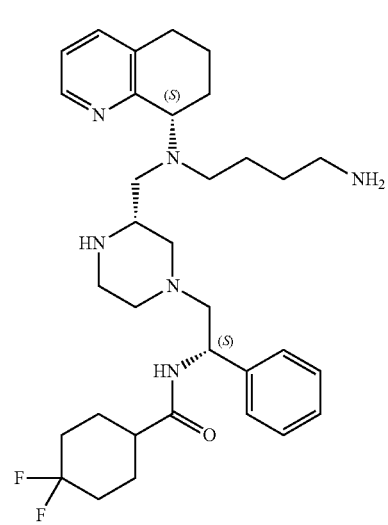

9
-continued
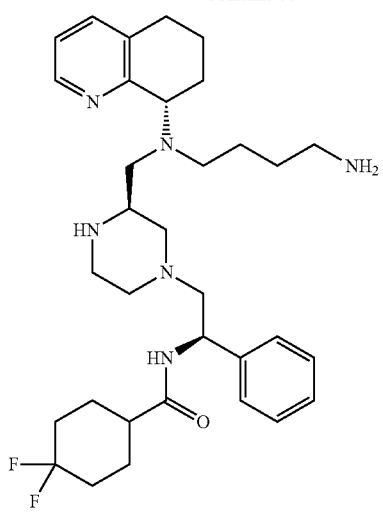
10
-continued
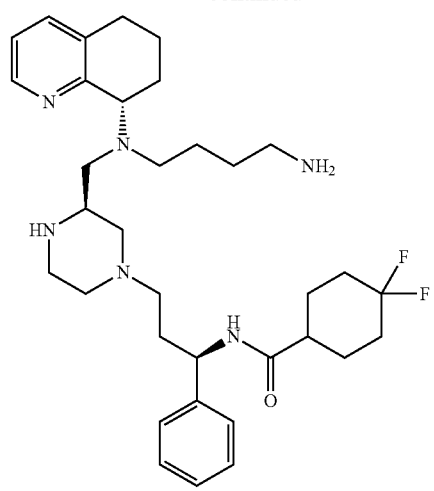
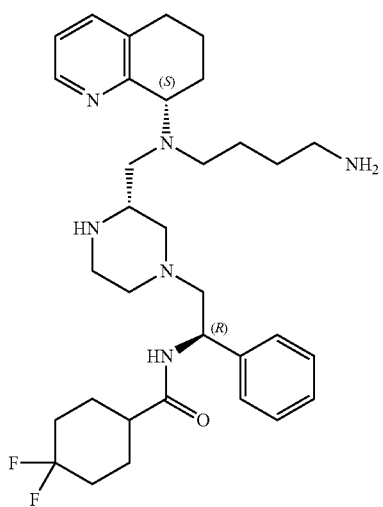
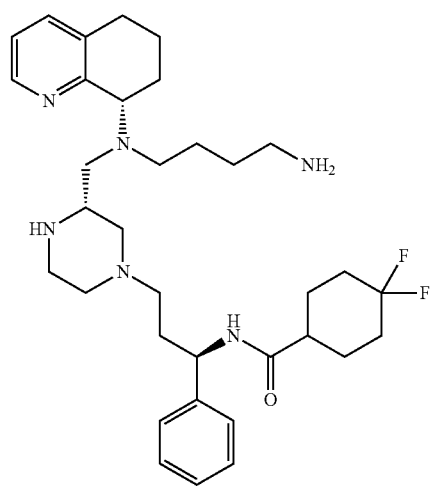
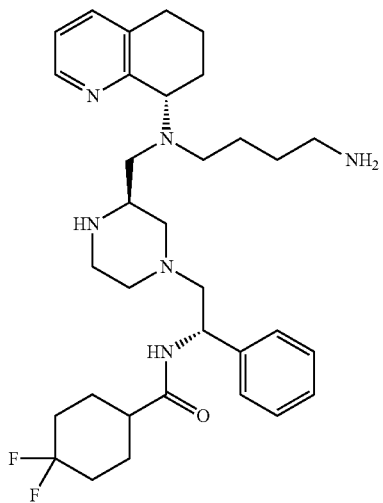

11
-continued
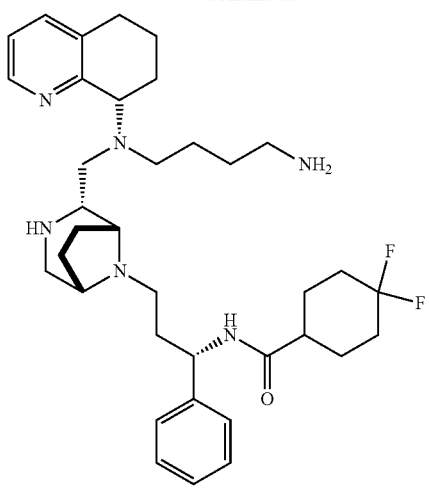
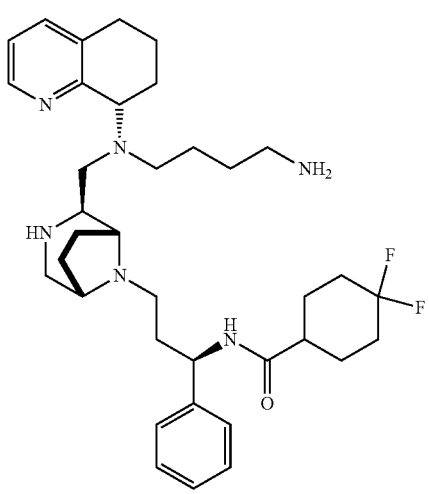
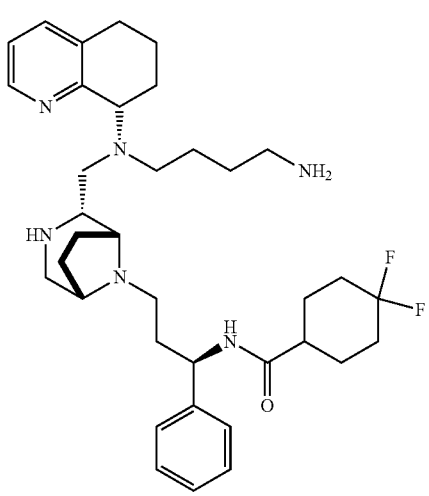
12
-continued
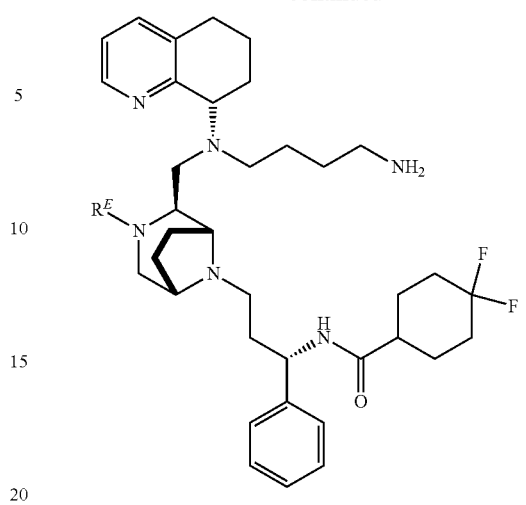
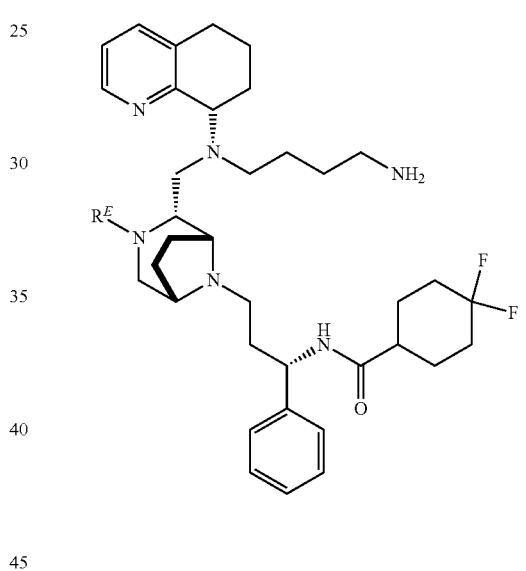
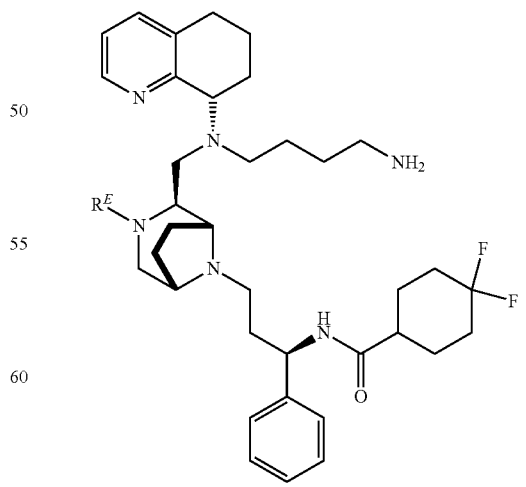

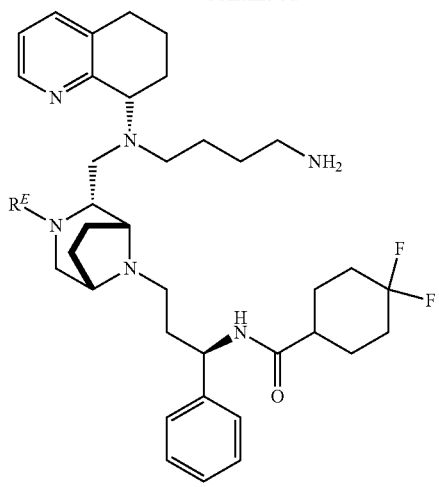
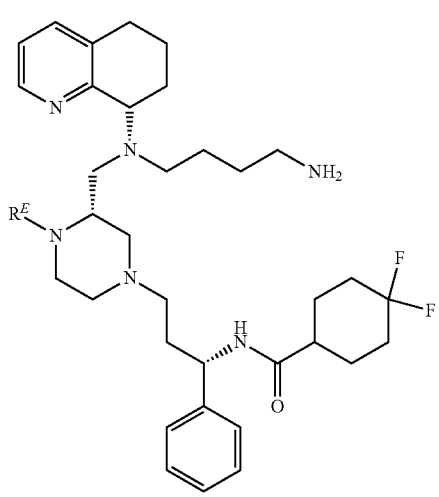
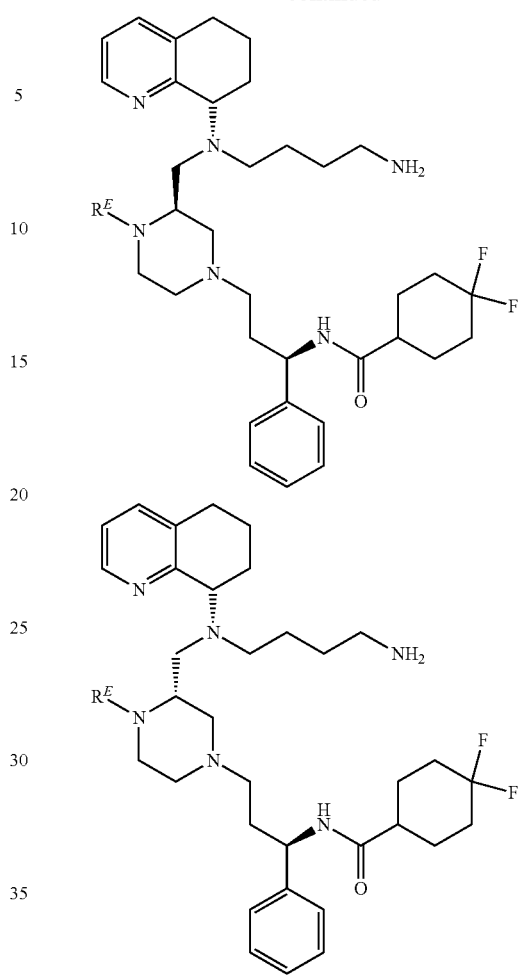
wherein $R^E$ is an optionally substituted alkyl, carbocycle, heterocarbocycle, aryl, or heteroaryl such as:
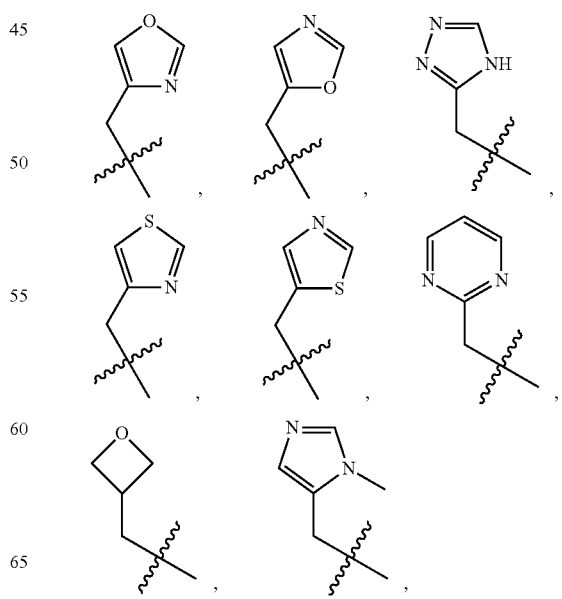

-continued

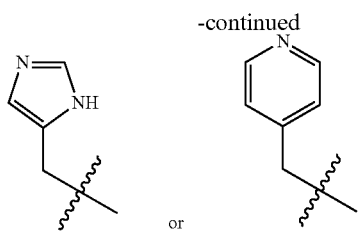

or

In certain embodiments, the disclosure relates to isolated compositions comprising compounds disclosed herein in substantially pure form.

In certain embodiments, the disclosure relates to a pharmaceutical formulation comprising a compound as described herein including salts and prodrugs thereof and a pharmaceutically acceptable excipient, diluent, or carrier. In certain embodiments, the pharmaceutical composition is in the form of a tablet, pill, capsule, gel, or aqueous buffered solution.

In certain embodiments, the disclosure relates to uses of compounds disclosed herein in the production of a medicament for the treatment of CXCR4 and CCR5 related conditions, such as, viral infections, abnormal cellular proliferation, retinal degeneration, inflammatory diseases, or as an immunostimulant or immunosuppressant.

In certain embodiments, the disclosure relates to pharmaceutical compositions comprising a compound as described herein and another active ingredient such as an antiviral agent or chemotherapeutic agent.

In certain embodiments, the disclosure relates to methods of treating or preventing a viral infection, the method comprising administering pharmaceutical composition comprising a compound as described herein optionally in combination with another active ingredient to a subject in need thereof. In further embodiments, the subject is at risk of, exhibiting symptoms of, or diagnosed with a viral infection.

In certain embodiments, the disclosure relates to uses of a compound as described herein in the production of a medicament for the treatment of a viral infection. In a typically embodiment, the viral infection is an IV infection.

In certain embodiments, the disclosure relates to methods of treating or preventing cancer, the method comprising administering a pharmaceutical composition comprising a compound as described herein optionally in combination with another active ingredient to a subject in need thereof. In further embodiments, the subject is at risk of, exhibiting symptoms of, or diagnosed with cancer.

In certain embodiments, the disclosure relates to methods of making compounds disclosed herein comprising mixing starting materials and reagents under conditions such that the product is formed.

DETAILED DESCRIPTION

Figure 1:
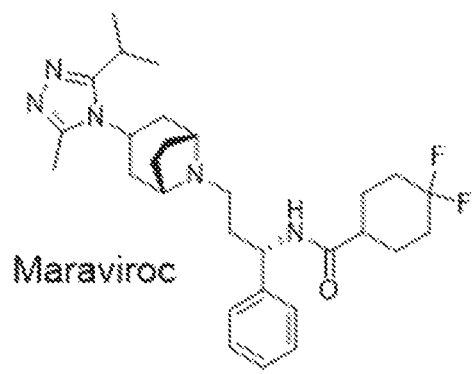
FIG. 1 shows the structure of Maraviroc.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated C1-4alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl- 1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or "heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge.

Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge.

An example of an alkylamino is methylamino, (i.e., —NH—$CH_3$).

"Aminoalkyl" refers to an amino group attached through an alkyl bridge as defined above (i.e., $NH_2$-alkyl-).

"Alkanoyl" refers to an alkyl as defined above attached through a carbonyl bride (i.e., —C(=O)alkyl).

"Alkylsulfonyl" refers to an alkyl as defined above attached through a sulfonyl bridge (i.e., —S(=O)$_2$alkyl) such as mesyl and the like, and "arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —NHS(=O)$_2$alkyl), and an "Arylsulfamoyl" refers to an alkyl attached through a sulfamoyl bridge (i.e., —NHS(=O)$_2$aryl).

"Alkylsulfinyl" refers to an alkyl as defined above attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aS_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2R_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

Methods of Use

In certain embodiments, the compounds described herein are useful for the treatment of viral infections where the virus utilizes CXCR4 and/or CCR5 to infect cells.

In one embodiment, the disclosure relates to a method of treating or preventing HIV infection or reduction of symptoms associated with AIDS is provided including administering a compound disclosed herein to a subject. In certain embodiments, the compound can be provided to a subject before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a subject at high risk of suffering from HIV infections.

Subjects, including humans suffering from, or at risk for, HIV infection can be treated by administering an effective amount of the active compound or a pharmaceutically acceptable prodrug or salt thereof in the presence of a pharmaceutically acceptable carrier or diluent.

The administration can be prophylactically for the prevention of HIV infection or reduction of symptoms associated with AIDS. The active materials can be administered by any appropriate route, for example, orally, parenterally, intravenously, intradermally, subcutaneously, or topically, in liquid or solid form.

In a separate embodiment, a method for the treatment or prevention of HIV infection or reduction of symptoms associated with AIDS by administering a compound or derivative of the present disclosure, or a pharmaceutically acceptable salt, solvate, prodrug, or ester thereof to a subject in need of treatment is provided. The compounds of the disclosure, or a pharmaceutically acceptable salt, solvate, prodrug, or ester thereof can be administered to a subject in need thereof to reduce the severity of AIDS related disorders. In one embodiment of the disclosure, the subject is a human.

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald et al., (2004) *Eur J Immun;* 34(4): 1164-1174). High levels of CXCR4 and TGFβ have been detected in liver samples obtained from patients infected with HCV. (Mitra et al., (1999) *Int J Oncol* 14: 917-925). In vitro, TGF-β has been shown to up-regulate the expression of CXCR4 on T cells and to increase their migration. The CD69/TGFβ/CXCR4 pathway may be involved in the retention of recently activated lymphocytes in the liver (Wald et al., *Eur J Immun,* 2004; 34(4): 1164-1174).

In another embodiment, the disclosure relates to a method of treating symptoms associated with other infections associated with chemokine receptor activation, for example, liver diseases associated with flavivirus or pestivirus infection, and in particular, HCV or HBV, by contacting a cell with a compound of the present disclosure, or a pharmaceutically acceptable salt, solvate, prodrug, or ester thereof. The cell can be in a subject animal, in particular in a human.

The compounds or derivatives can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma. Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, Nature, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, (1990) *The New England Journal of Medicine*, 322:1277-1289), and to be caused by auto-antibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatie bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and hypothalamic glioma, vulvar cancer, Waldenstrom's macroglobulinemia, Wilm's tumor, and any other hyperproliferative disease located in an organ system listed above.

In certain embodiments, the compound derivatives disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, the disclosure relates to a method for the treatment of, prevention of, or reduced severity of, age-related macular degeneration (ARMD) and other pathogenic states involving macular retinal pigment epithelial (RPE) cells by administering at least one compound or derivative described herein to a subject in need thereof.

CXCR4 plays a role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) *J. Immunol.* 165: 4372-4278). The level of CXCR4 mRNA expression increases upon stimulation with IL-1β or TNFα (Dwinell, et al. (1999) *Gastroenterology.* 117: 359-367). RPE cells also migrated in response to SDF-1α indicating that SDF-1α/CXCR4 interactions may modulate the effects of chronic inflammation and subretinal neovascularization at the RPE site of the blood-retina barrier.

Age-related macular degeneration is characterized by both primary and secondary damage of macular RPE cells.

In a separate embodiment, a method for the treatment of, prevention of, or reduced severity of inflammatory disease states, neovascularization, and wound healing including administering at least one compound or derivative described herein to a subject in need thereof. Vascular endothelial cells express a multitude of chemokine receptors, with CXCR4 being particularly prominent (Gupta, et al. (1998) *J Biol Chem.* 273: 4282; Volin, et al. (1998) *Biochem Biophys Res Commnun.* 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues. (Murdoch, et al. (1998) *Immunology.* 98(1): 36-41). Unlike with endothelial cells, CXCR4 is the only chemokine receptor expressed on epithelial cells. The receptor may have a functional role in epithelial pathology. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis *nodosa*); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs.

In one embodiment, the compounds or derivatives of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBQ 8 count, or who would benefit from elevation of WBC levels using the compounds disclosed herein. Moreover, the disclosure is directed to methods of effecting regeneration of cardiac tissue in a subject in need of such regeneration using the disclosed compounds.

The compounds or derivatives of the disclosure may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

Formulations Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

The compositions described herein can be formulation for modified or controlled release. Examples of controlled release dosage forms include extended release dosage forms, delayed release dosage forms, pulsatile release dosage forms, and combinations thereof.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

In certain embodiments, the disclosure relates to compounds disclosed herein, derivatives, prodrugs, esters, or salts and compositions thereof. Although it is not intended that certain embodiments of the disclosure be limited by any particular mechanism it is believed that these compounds are chemokine CXCR4 and/or CCR5 receptor modulators.

Applicant has identified novel pan-tropic HIV entry inhibitors. Since these compounds inhibit the action of host proteins, they should, in principle, synergize with any HIV drug that targets a viral protein, thereby expanding the number of new combination therapies that could be developed. This could be particularly important in resource-challenged environments where the use of first-line therapies is not economically feasible.

Single agent, pan-tropic chemokine entry inhibitors could:

(i) prevent M-, MIT- and T-tropic viruses from entering and establishing infection in immune cells;

(ii) exhibit a high barrier to the development of resistance; and (iii) synergize with HIV drugs that target viral proteins.

The development of a safe and effective pan-tropic HIV entry inhibitor would greatly expand the patient population that could be treated relative to those being treated with combinations including Maraviroc.

The present disclosure will be described in more detail with reference to the following non-limiting examples. It should be noted that the particular assays used in the examples section are designed to provide an indication of activity.

A replacement of the benzimidazole ring of AMD11070 with a tetrahydroquinoline (THQ) ring and hybridization with a piperazine core, a common component of CCR5 antagonists (Briz et al., *J Antimicrob Chemother*, 2006, 57(4)) resulted in the establishment of the PIP series of the present application, which generally exhibited $EC_{50}$ values <50 nM against the T-tropic (CXCR4) virus and 2-7 µM against the M-tropic (CCR5) virus. Applicant subsequently hypothesized that CCR5 activity could be improved upon in this series by including a difluoro side chain similar to Maraviroc. Six diastereomers of this new series were synthesized and, from these, 1 and 2 proved to be the most potent (see Table 1, below).

TABLE 1

HIV MAGI $EC_{50}$ Values

| Compound No. | 1 | 2 |
| --- | --- | --- |
| $HIV_{IIIB}$: | 0.22 µM | 0.07 µM |
| $HIV_{Ba-L}$: | 2.6 µM | 2.61 µM |
| CYP2D6: | >20 µM | >20 µM |
| CYP3A4: | >20 µM | >20 µM |
| HLM: | 58% @ 10 min | 65% @ 10 min |
| MLM: | 100% @ 10 min | 95% @ 10 min |

Figure 4:
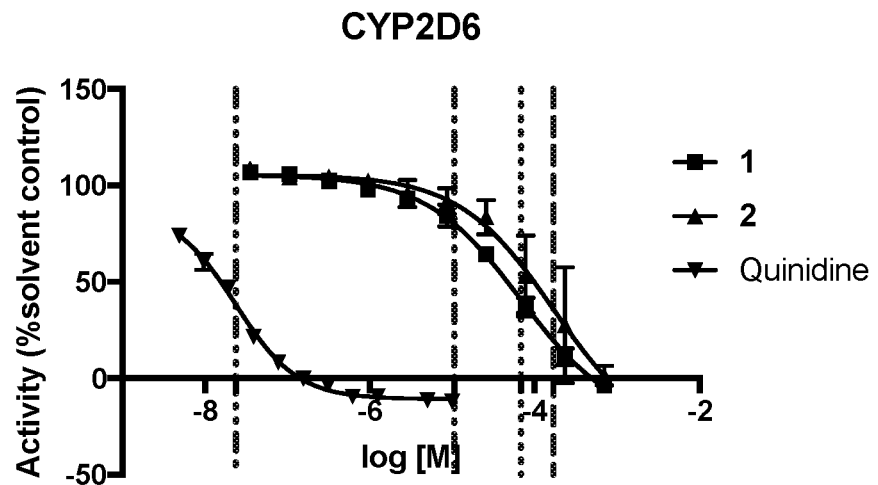
FIG. 4 is a graph showing the calculated $IC_{50}$ values of exemplary compounds on P450 2D6.
Figure 5:
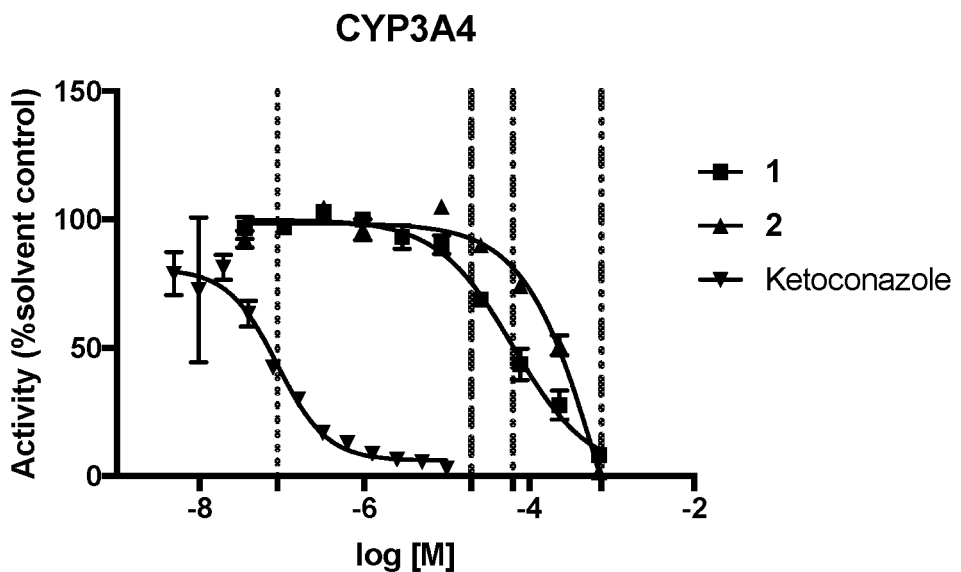
FIG. 5 is a graph showing the calculated $IC_{50}$ values of exemplary compounds on P450 3A4.

Docking studies showed that 2, which binds in a similar pose to Maraviroc (shown in FIG. 1), benefits from an important salt bridge between its piperazine nitrogen and Glu283, similarly to Maraviroc. In the same model, diastereomer 1 was unable to form this salt bridge. Preliminary screening of the ADME properties of 2 was conducted and the data showed that 2 does not inhibit the cytochrome P450 isoforms, 2D6 and 3A4. This is a remarkable improvement over AMD11070, which potently inhibited both isoforms at 1 µM (i.e., 100% (2D6) and 35% (3A4)). In addition, 2 showed good stability in both human and mouse liver microsomes. (See FIGS. 4-5 and Table 2).

While addition of Maraviroc's difluoro side chain markedly improved both the CXCR4 and CCR5 potencies, Applicant believes that the CCR5 activity can be further improved by structural modifications to lead compound 2 that reinforce the active conformation of Maraviroc.

Figure 2:
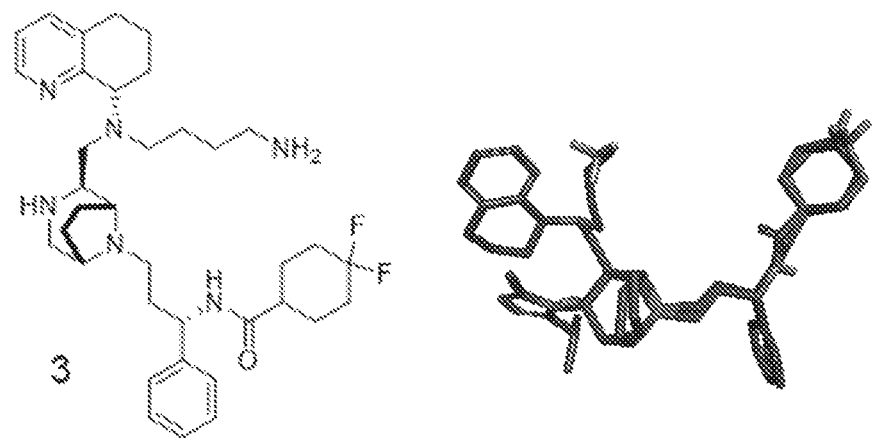
FIG. 2 shows the structure of compound 3 and a modeling picture in which it is overlaid with Maraviroc.
Figure 3:
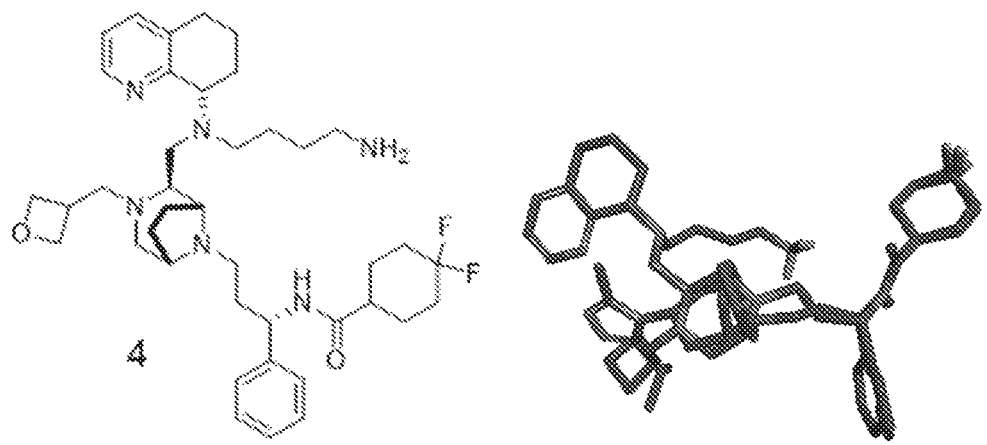
FIG. 3 shows the structure of compound 4 and a modeling picture in which it is overlaid with Maraviroc.

The first modification replaces the core in 2 with a bridged piperazine ring to give compound 3 and based on modeling studies, an overlay of 3 aligns better with the bioactive conformer of Maraviroc (FIG. 2). The inclusion of an oxetane ring at the bridged piperazine nitrogen, to produce 4 is also expected to improve potency (FIG. 3). The space around residue Tyr37 can also be explored by appending heterocycles to piperazines 2 and 3, which will serve as hydrogen bond acceptors to Tyr37.

The piperazine core 5 and 6 were both synthesized using previously developed protocols (Tagat et al., *J Med Chem*, 2004, 47(10); Armour et al., *Chem Biol Drug Des*, 2006, 67(4)), and 2 was prepared via a triacetoxyborohydride-mediated reductive amination reaction of 5 and 6, followed by Boc-deprotection with TFA. The same three-step sequence can be utilized to generate 3. The piperazine moiety of 5 can be exchanged for a bridged piperazine, which can be prepared in 8-steps from 5-methoxy-3,4-dihydro-2H-pyrrole-2-carboxylic acid methyl ester (Åhman et al., *Org Proc Res Dev*, 2008, 12(6)).

A reductive amination reaction between commercially available heterocyclic aldehydes (for example, those depicted as R') and 2' or 3' (i.e., protected versions of 2 and 3) should give 7-10 or their bridged counterparts 7'-10'. A reductive amination reaction of 3' and 3-oxetane carboxaldehyde, followed by deprotection, will produce 4 (shown in FIG. 3).

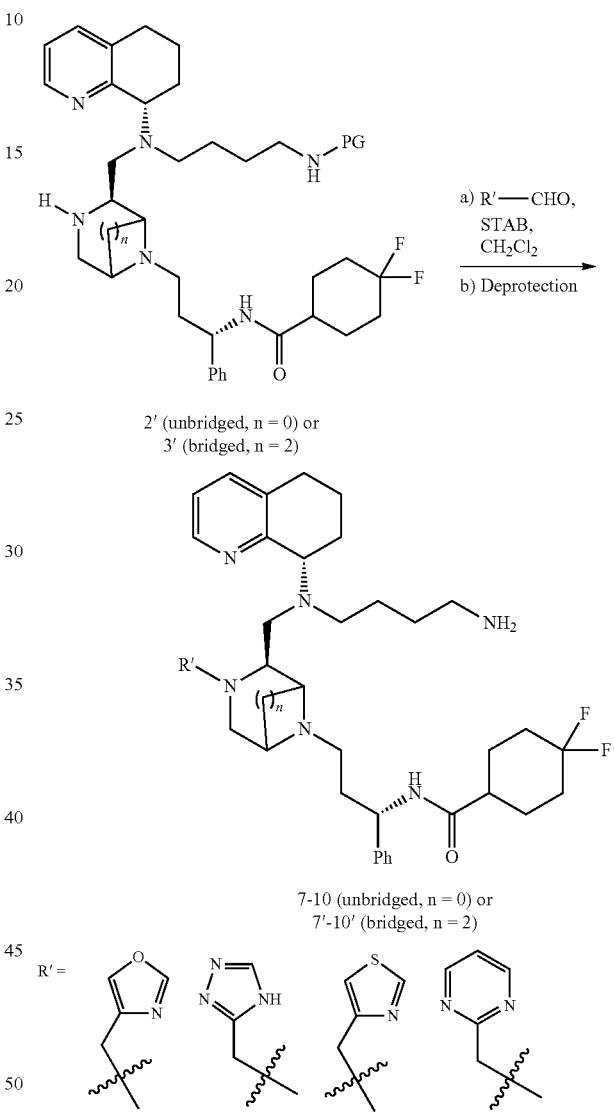

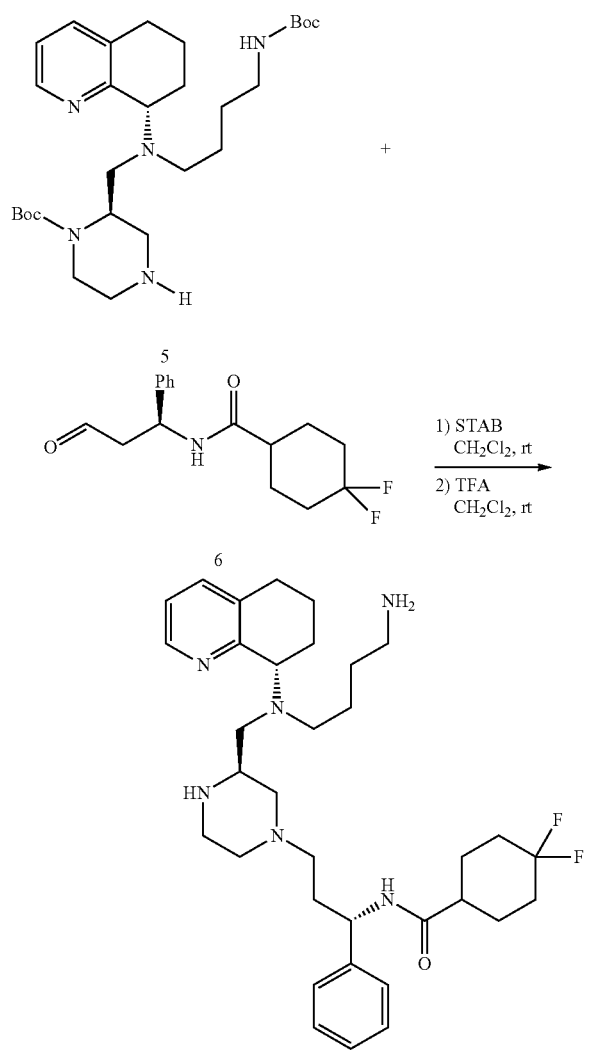

Synthesis of Exemplary Compounds

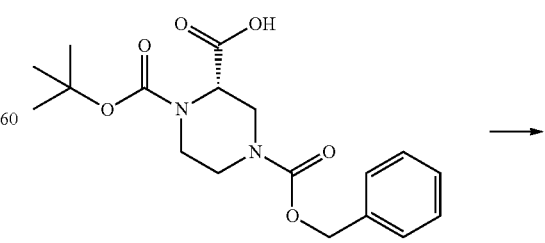

12

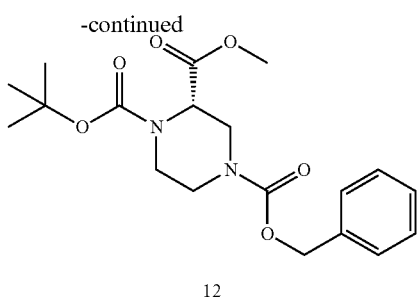

A 500 mL rb flask equipped with a rubber septum and a magnetic stir bar was set under Ar atmosphere and charged with 5 g of acid 11 (13.7 mmol, 1 equiv.), 503 mg of DMAP (4.12 mmol, 0.3 equiv.), 3.16 g of EDCI (16.5 mmol, 1.2 equiv.), 196 mL of $CH_2Cl_2$ and 65 mL of dry MeOH. After stirring at rt for 12 h, the reaction mixture was quenched by addition of sat. $NaHCO_3$ solution, extracted with $CH_2Cl_2$ (3×) and dried over $Na_2SO_4$. The crude product was purified on silica gel column using 0 to 50% EA in hexanes as eluent affording 4.86 g (94%) of the product 12 as a clear oil.

13

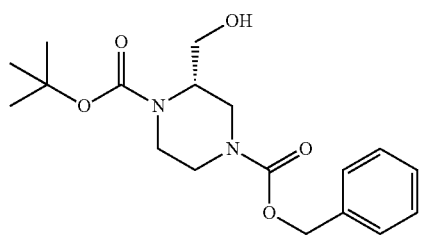

A 250 mL rb flask equipped with a rubber septum and magnetic stir bar was charged with 2.28 g of $CaCl_2$ (20.5 mmol, 1.6 equiv.) followed by 4.86 g of 4-benzyl 1-tert-butyl 2-methyl piperazine-1,2,4-tricarboxylate 12 (12.8 mmol, 1 equiv.) dissolved in 128 mL of 1:1 mixture of THF and EtOH. After stirring at rt for 20 min, the clear solution was cooled to 0° C. and 2.06 g of $NaBH_4$ (54.6 mmol, 4.25 equiv.) was added and the suspension was stirred at 0° C. for 30 min. Then the reaction mixture was allowed to warm to rt and the stirring was continued for 12 h. The reaction was quenched by addition of 1 M HCl till no bubbling is observed (pH paper showed neutral solution) and the product is extracted with diethyl ether (3×), washed with water (2×), brine and dried over $Na_2SO_4$. The crude product was purified on silica gel column using 10 to 30% EA in hexanes as eluent affording 4.20 g (93%) of product 13 as a clear oil.

14

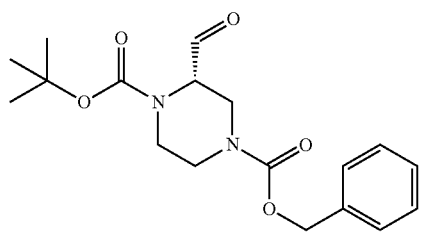

A 250 mL rb flask equipped with a magnetic stir bar and septum was charged with 4.10 g of the alcohol 13 (11.7 mmol, 1 equiv.), 8.64 mL of $Et_3N$ (62.0 mmol, 5.3 equiv.) and 35 mL of $CH_2Cl_2$. After reaction mixture was cooled to 0° C., 7.45 g of $SO_3$*Py (46.8 mmol, 4 equiv.) dissolved in 35 mL of DMSO (dissolve in other flask under Ar) was added dropwise and the reaction mixture was stirred at 0° C. for 3 h. Then the reaction mixture was quenched by addition of sat. $NaHCO_3$ solution, extracted with $CH_2Cl_2$ (3×), washed with water and brine and dried over $Na_2SO_4$. After the organics were concentrated, toluene was added and the organic solvents were removed under vacuum (rotatory evaporator and high vacuum) to remove residual pyridine and $Et_3N$. The aldehyde 14 was used in the next step without further purification.

15

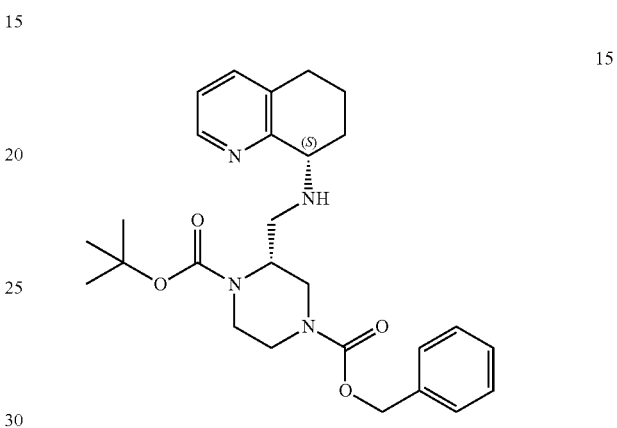

A 250 mL rb flask equipped with a stir bar was charged with 2.60 g of (S)-5,6,7,8-tetrahydroquinolin-8-amine (17.6 mmol, 1.5 equiv.), 4.08 g of the aldehyde 14 (11.7 mmol, 1 equiv.) and 78 mL of DCE. Then 3.97 g of $NaBH(OAc)_3$ (18.7 mmol, 1.6 equiv.) was added. After stirring at rt for 12 h, the reaction mixture was quenched by addition of sat. $Na_2CO_3$ solution and the product was extracted with $CH_2Cl_2$ (3×) and dried over $Na_2SO_4$. The crude product was purified on silica gel column using EA (to separate the SM) followed by 20% MeOH in $CH_2Cl_2$ as eluent affording 5.12 g (91%) of the product 15 as yellowish oil.

16

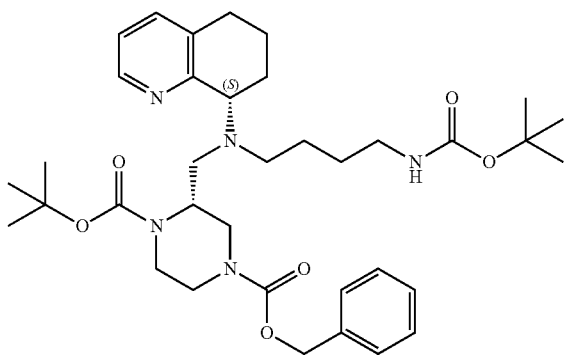

A 250 mL rb flask equipped with a stir bar was charged with 3.04 g of the amine 15 (6.33 mmol, 1 equiv.), 1.78 g of tert-butyl (4-oxobutyl)carbamate (9.49 mmol, 1.5 equiv.) and 31 mL of DCE. Then 2.68 g of $NaBH(OAc)_3$ (12.7 mmol, 2 equiv.) was added. After stirring at rt for 48 h, the reaction was not done. 380 mg of acetic acid (6.33 mmol, 1 equiv.) was added and the stirring was continued for 24 h.

Reaction was still incomplete. Then 1.78 g of tert-butyl (4-oxobutyl)carbamate (9.49 mmol, 1.5 equiv.) was added and the reaction was stirred for 12 h. Then 2.68 g of NaBH(OAc)₃ (12.7 mmol, 2 equiv.) was added. After stirring for 12 h, reaction went to completion. The reaction mixture was quenched by addition of sat. Na₂CO₃ solution and the product was extracted with CH₂Cl₂ (3×) and dried over Na₂SO₄. The crude product was purified on silica gel column using 0-100% EA in hexanes as eluent affording 2.21 g (53%) of the product 16 as a clear oil.

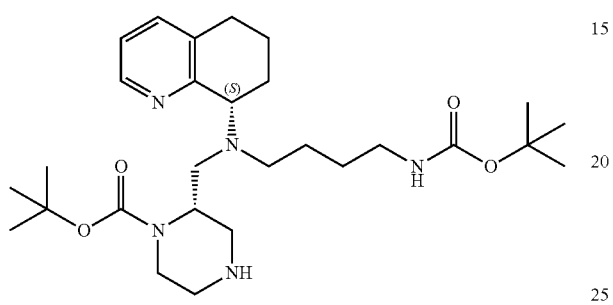

17

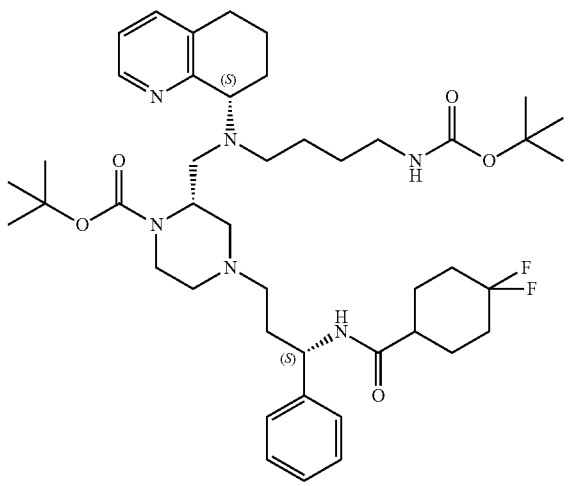

18

A 20 mL vial equipped with a stir bar was charged with 0.171 g of the aldehyde 6 (0.580 mmol, 1.2 equiv.), 0.250 g of the amine 17 (0.483 mmol, 1 equiv.), 28 μL of CH₃COOH (0.483 mmol, 1 equiv.) and 4.8 mL of DCE. Then 0.143 g of NaBH(OAc)₃ (0.676 mmol, 1.4 equiv.) was added and the suspension was stirred at rt for 12 h. The reaction mixture was quenched by the addition of a saturated NaHCO₃ solution, extracted with CH₂Cl₂ (3×) and dried over Na₂SO₄. The crude product is purified on silica gel column using 0 to 100% EA in hexanes as eluent affording 296 mg (77%) of the product 18 as a slightly yellow oil.

A 100 mL rb flask equipped with a stir bar and rubber septum was charged with 1.36 g of the carbamate 16 (2.09 mmol, 1 equiv.), 293 mg of 20 w % of Pd(OH)₂ on carbon (0.417 mmol, 0.2 equiv.) and 25 mL of dry EtOH. Then 526 mg of NH₄OOCH (8.35 mmol, 4 equiv.) was added in one portion. After stirring at rt for 1 h, the reaction mixture was filtered through a celite plug and the celite plug was washed with EtOH. The organics were concentrated in vacuo (rotatory evaporator) affording 1.06 g (98%) of the product 17 as a yellowish oil.

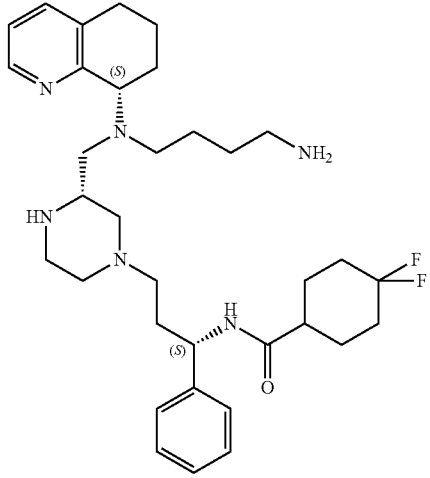

1

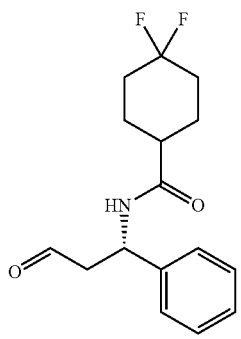

6

According to the reference (*Organic Process Research & Development* 2008, 12, 1094 1103; *Organic Process Research & Development* 2008, 12, 1104-1113), the aldehyde 6 was synthesized from 4,4-difluorocyclohexanecarboxylic acid and 5.00 g of ethyl (S)-3-amino-3-phenylpropanoate hydrochloride in 4 steps and 44% overall yield affording the product 6 as a white solid.

A 20 mL vial equipped with a stir bar was charged with 183 mg of the amine 18 (0.230 mmol, 1 equiv.) dissolved in 2.3 mL of CH₂Cl₂. Then 0.531 mL of CF₃COOH (6.89 mmol, 30 equiv.) was added. After stirring at rt for 12 h, the reaction mixture was quenched by addition of a 2 N NaOH solution, extracted with CH₂Cl₂ (3×) and dried over Na₂SO₄. The crude material was purified on a silica gel column using 0-45% Solvent 2 (Solvent 2=70% CH₂Cl₂, 30% MeOH, 3% NH₄OH) in CH₂Cl₂ as eluent (4 g column) affording 88 mg (64%) of the product 1 as a white foam. ¹H NMR (400 MHz, CDCl₃, ppm) δ: 8.39 (dd, J=4.8, 1.6 Hz, 1H), 8.20 (d, J=7.0 Hz, 1H), 7.30-7.23 (m, 3H), 7.20-7.13 (m, 3H), 6.99 (dd, J=7.7, 4.7 Hz, 1H), 5.02 (q, J=6.0 Hz, 1H), 3.94 (dd, J=9.6, 5.8 Hz, 1H), 3.01 (d, J=11.6 Hz, 1H), 2.87 (d, J=11.2 Hz, 1H), 2.81-1.55 (m, 33H), 1.46-1.31 (m, 4H). $^{13}$C NMR (100 MHz, CDCl$_3$, ppm) δ: 173.21, 158.11, 146.81, 142.11, 136.44, 134.01, 128.34, 126.82, 125.92, 124.98, 122.59 (t, J=240.7 Hz), 121.46, 61.64, 58.53, 57.16, 55.04, 54.80, 53.23, 52.89, 52.25, 45.53, 42.78, 41.81, 32.71 (t, J=24.4 Hz), 31.21, 31.11, 29.20, 26.99, 26.09 (d, J=7.8 Hz), 26.05, 25.87 (d, J=9.4 Hz), 21.54. $^{19}$F NMR (376 MHz, CDCl$_3$, ppm) δ: −94.08 (d, J=236.6 Hz), −101.35 (d, J=236.5 Hz). HRMS (ESI+) calcd for $C_{34}H_{51}ON_6F_2$ ([M+H]$^+$): 597.4087. Found: 597.4080, error −0.7 ppm. LC-MS (ESI-API, 254 nm) 75-95% MeOH in H$_2$O (0.1% HCO$_2$H), 3 min, 1.00 mL/min, C18 (Agilent Zorbax XDB-18, 50 mm×4.6 mm, 3.5 μm), m/z=597.2 (M+H), 299.2 (M/2+H), t=0.628 min.

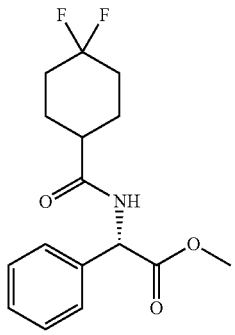

19

A 250 mL rb flask equipped with a magnetic stir bar was charged with 6.89 g of Na$_2$CO$_3$ (65.0 mmol, 2.28 equiv.) dissolved in 49 mL of water at ambient temperature and 5.70 g of methyl (S)-2-amino-2-phenylacetate hydrochloride (28.6 mmol, 1 equiv.), followed by 25 ml of CH$_2$Cl$_2$ and the mixture was cooled in ice bath. Then 4.38 g of 4,4-difluorocyclohexane-1-carbonyl chloride (24.0 mmol, 0.84 equiv.) dissolved in 13 mL of toluene was added. After stirring at rt for 2 h, the reaction mixture was adjusted to pH 9-10 by the addition of 10 M NaOH. The crude product was extracted with CH$_2$Cl$_2$ (3×), washed with 2 M NaOH and water, 2 M HCl solution, water, brine and dried over Na$_2$SO$_4$. The organics were concentrated to 60 mL volume and 6 mL of toluene was added. The organics were concentrated to 24 mL volume and 24 mL of heptane was added. The suspension was cooled and the product was filtered, washed with heptane affording 6.95 g (78%) of the product 19 as a white solid.

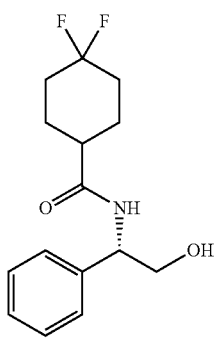

20

A 250 mL rb flask, equipped with magnetic stir bar, reflux condenser and rubber septum, was charged with 3.0 g of the ester 19 (9.63 mmol, 1 equiv.) and 0.729 g of NaBH$_4$ (19.3 mmol, 2 equiv.) and 23 mL of THF. After the mixture was heated to 50° C., 1.97 mL of MeOH (9.64 mmol, 1 equiv.) was added dropwise. Then the reaction mixture was heated to reflux and held for 90 min, then cooled to 20° C. and 3.5 mL of acetone was added. The mixture was stirred for 15 min and 30 mL of CH$_2$Cl$_2$ was added, followed by 16 mL of 2 M NaOH solution. After stirring for 2 h, the product was extracted with CH$_2$Cl$_2$ (3×), washed with brine and dried over Na$_2$SO$_4$. The organics were filtered and concentrated affording 2.39 g (88%) of the product 20 as a white solid.

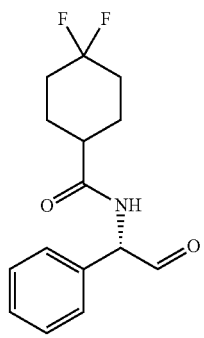

21

Similar to the ref. *Tetrahedron: Asymmetry*, 2002, 13, 2509-2512, a 250 mL rb flask equipped with a magnetic stir bar and rubber septum was charged with 1.80 g of the alcohol 20 (6.35 mmol, 1 equiv.) and 50 mL of CH$_2$Cl$_2$. Then 5.66 g of Dess-Martin periodinane (13.3 mmol, 2.1 equiv.) was added. After stirring at rt for 1 h, 21 mL of ethyl ether was added followed by 27.7 g of Na$_2$S$_2$O$_3$*5H$_2$O dissolved in 23 mL of 80% sat. NaHCO$_3$. Organic layer was separated, and the aqueous phase was extracted with 48 mL of diethyl ether. Organic solution was washed with 32 mL of sat. NaHCO$_3$solution, 32 mL of water (2×) and 32 mL of brine (2×). After drying over MgSO$_4$, the solvents were partially evaporated (water bath below 20° C.). The residue was triturated with hexanes until turbidity and left at rt overnight. Solvents were removed, solid aldehyde product was filtered, washed with a 4:1 hexane-ether mixture and dried under vacuum affording 1.01 g (56%) of the product 21 as a white solid. About 10 mg of the aldehyde 21 was dissolved in 0.5 mL of MeOH and 20 mg of NaBH$_4$ was added. After 10 min, 2 M HCl was added till no bubbling was observed and the product was extracted with CH$_2$Cl$_2$ (2×), washed with water and dried over Na$_2$SO$_4$. The crude product was analyzed on HPLC. HPLC (210, 254 nm) 5% iPrOH in hexanes, 20 min, 0.85 mL/min, (CHIRALCEL OD-H, 250 mm×4.6 mm), t=9.556 min (0.17%), t=12.026 min, (98.78%); The low yield and high enantiopurity of the aldehyde can be explained due to crystallization during last steps of the workup in the synthesis of the aldehyde.

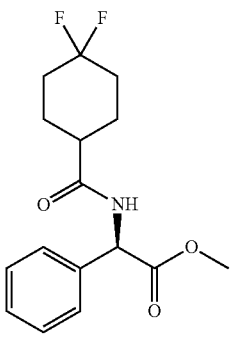

22

A 250 ml rb flask equipped with a magnetic stir bar was charged with 5.31 g of $Na_2CO_3$ (50.1 mmol, 2.28 equiv.) dissolved in 49 mL of water at ambient temperature and 4.39 g of methyl (R)-2-amino-2-phenylacetate hydrochloride (22.0 mmol, 1 equiv.), followed by 25 ml of $CH_2Cl_2$ and the mixture was cooled in ice bath. Then 4.38 g of 4,4-difluorocyclohexane-1-carbonyl chloride (24.0 mmol, 1.1 equiv.) dissolved in 13 mL of toluene was added. After stirring at rt for 2 h, the reaction mixture was adjusted to pH 9-10 by the addition of 10 M NaOH. The crude product was extracted with $CH_2Cl_2$ (3×), washed with 2 M NaOH and water, brine and dried over $Na_2SO_4$. The organics were concentrated to 60 mL volume and 6 mL of toluene was added. The organics were concentrated to 24 mL volume and 24 mL of heptane was added. The suspension was cooled and the product was filtered, washed with heptane affording 6.15 g (90%) of the product 22 as a white solid.

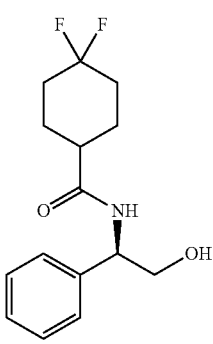

23

A 250 mL rb flask, equipped with magnetic stir bar, reflux condenser and rubber septum, was charged with 3.0 g of the ester 22 (9.63 mmol, 1 equiv.) and 0.729 g of $NaBH_4$ (19.3 mmol, 2 equiv.) and 23 mL of THF. After the mixture was heated to 50° C., 1.97 mL of MeOH (9.64 mmol, 1 equiv.) was added was added dropwise. Then the reaction mixture was heated to reflux and held for 90 min, then cooled to 20° C. and 3.5 mL of acetone was added. The mixture was stirred for 15 min and 30 mL of $CH_2Cl_2$ was added, followed by 16 mL of 2M NaOH solution. After stirring for 2 h, the product was extracted with $CH_2Cl_2$ (3×), washed with brine and dried over $Na_2SO_4$. The organics were filtered and concentrated affording 2.51 g (92%) of the product 23 as a white solid.

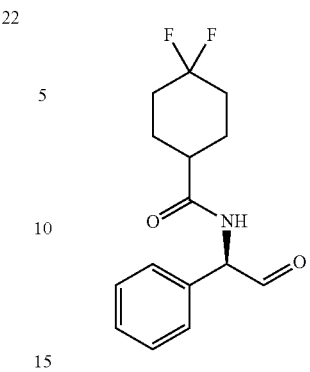

24

Similar to the ref. *Tetrahedron: Asymmetry*, 2002, 13, 2509-2512, a 250 mL rb flask equipped with a magnetic stir bar and rubber septum was charged with 1.80 g of the alcohol 23 (6.35 mmol, 1 equiv.) and 50 mL of $CH_2Cl_2$. Then 5.66 g of Dess-Martin periodinane (13.3 mmol, 2.1 equiv.) was added. After stirring at rt for 1 h, 21 mL of ethyl ether was added followed by 27.7 g of $Na_2S_2O_3 \cdot 5H_2O$ dissolved in 23 mL of 80% sat. $NaHCO_3$. The organic layer was separated, and the aqueous phase was extracted with 48 mL of diethyl ether. The organic solution was washed with 32 mL of sat. $NaHCO_3$ solution, 32 mL of water (2×) and 32 mL of brine (2×). After drying over $MgSO_4$, the solvents were partially evaporated (water bath below 20° C.). The residue was triturated with hexanes until turbidity and left at rt overnight. Solvents were removed, the product was filtered, washed with a 4:1 hexane-ether mixture and dried under vacuum affording 0.910 g (51%) of the product 24 as a white solid. About 10 mg of the aldehyde 24 was dissolved in 0.5 mL of MeOH and 20 mg of $NaBH_4$ was added. After 10 min, 2 M HCl was added till no bubbling was observed and the product was extracted with $CH_2Cl_2$ (2×), washed with water and dried over $Na_2SO_4$. The crude product was analyzed on HPLC. HPLC (210, 254 nm) 5% iPrOH in hexanes, 20 min, 0.85 mL/min, (CHIRALCEL OD-H, 250 mm×4.6 mm), t=9.615 min (94.45%), no other isomer; The low yield and high enantiopurity of the aldehyde can be explained due crystallization during last steps of the workup.

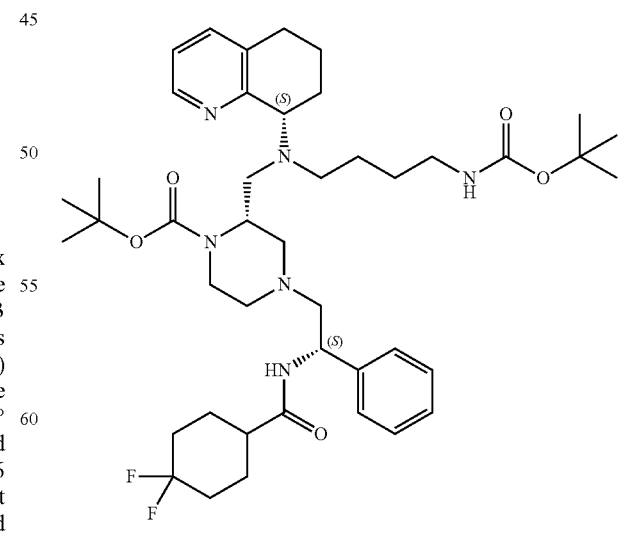

S,S,S-25

A 100 mL rb flask equipped with a stir bar and rubber septum was charged with 0.228 g of the aldehyde 21 (0.811 mmol, 1.2 equiv.), 0.350 g of the amine 17 (0.676 mmol, 1 equiv.) and 20 mL of CH₂Cl₂. Immediately 0.860 g of NaBH(OAc)₃ (4.06 mmol, 6 equiv.) was added and the suspension was stirred at rt for 12 h. During the reaction, an aldol reaction (546 in LC/MS), racemization of the aldehyde, and kinetic resolution proceeded (the amine prefers R aldehyde) affording 1:4 (S/R) of the isomers. The reaction mixture was quenched by addition of sat. NaHCO₃ solution, extracted with CH₂Cl₂ (3×) and dried over Na₂SO₄. The crude product is purified on silica gel column using 0 to 100% EA in hexanes as eluent affording 235 mg of unexpected S,S,R-isomer-25 and 208 mg of a mix of isomers (1:1 ratio). Another separation was performed to obtain 80 mg of the S,S,S-isomer-25 as a white foam.

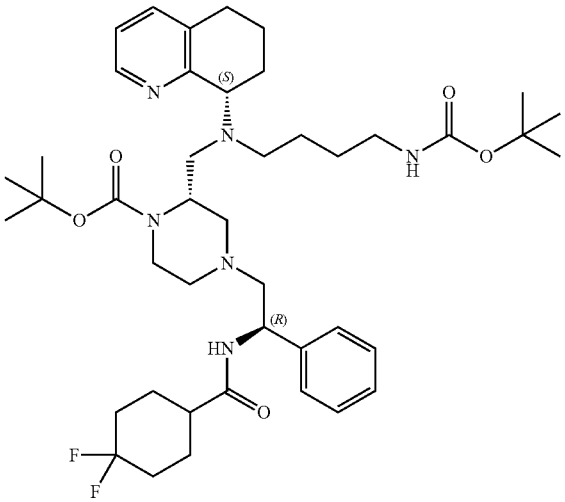

S,S,R-isomer-25

26

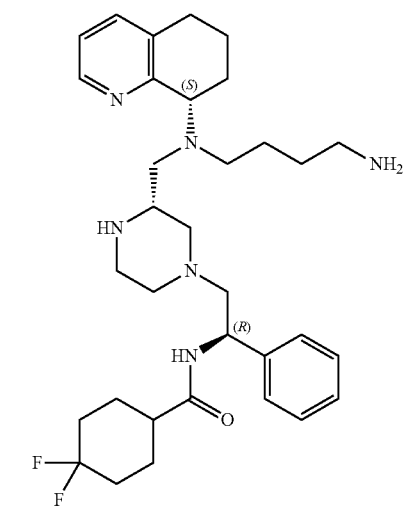

A 2 dram vial equipped with a stir bar was charged with 80 mg of the amine S,S,S-isomer-25 (0.102 mmol, 1 equiv.) dissolved in 1.5 mL of dioxane. Then 0.256 mL of 12 M HCl (3.07 mmol, 30 equiv.) was added. After stirring at rt for 1 h, the reaction mixture was quenched by addition of 2 N NaOH solution, extracted with CH₂Cl₂ (3×) and dried over Na₂SO₄. The crude material was purified on silica gel column using 0-45% of Solvent 2 (Solvent 2=70% CH₂Cl₂, 30% MeOH, 5% NH₄OH) in CH₂Cl₂ as eluent affording 48 mg (81%) of the product 26 as a white foam. $^1$H NMR (400 MHz, CDCl₃, ppm) δ: 8.43 (dd, J=4.7, 1.8 Hz, 1H), 7.34-7.17 (m, 6H), 7.02 (dd, J=7.7, 4.7 Hz, 1H), 6.59 (d, J=4.9 Hz, 1H), 4.84 (dt, J=10.2, 5.2 Hz, 1H), 3.96 (dd, J=9.5, 5.9 Hz, 1H), 2.90 (A of AB, $J_{AB}$=11.4 Hz, 1H), 2.84-1.61 (m, 32H), 1.47-1.33 (m, 4H). $^{19}$F NMR (376 MHz, CDCl₃, ppm) δ: −93.39 (d, J=236.6 Hz), −100.33 (d, J=236.3 Hz).

A 100 mL rb flask equipped with a stir bar and rubber septum was charged with 0.228 g of the aldehyde 24 (0.811 mmol, 1.2 equiv.), 0.350 g of the amine 16 (0.676 mmol, 1 equiv.) and 20 mL of CH₂Cl₂. Immediately 0.860 g of NaBH(OAc)₃ (4.06 mmol, 6 equiv) was added and the suspension was stirred at rt for 12 h. During reaction, an aldol reaction (546 in LC/MS), racemization of the aldehyde, and kinetic resolution proceeded (the amine prefers R aldehyde) affording single R isomer. The reaction mixture was quenched by addition of sat. NaHCO₃ solution, extracted with CH₂Cl₂ (3×) and dried over Na₂SO₄. The crude product is purified on silica gel column using 0 to 100% EA in hexanes as eluent affording of S,S,R-isomer-25 226 mg (pure product) and 200 mg of S,S,R-isomer-25 with some minor impurity.

27

A 2 dram vial equipped with a stir bar was charged with 125 mg of the amine S,S,R-isomer-25 (0.160 mmol, 1 equiv.) dissolved in 1.5 mL of dioxane. Then 0.146 mL of 12 M HCl (4.79 mmol, 30 equiv.) was added. After stirring at rt for 1 h, the reaction mixture was quenched by addition of 2 N NaOH solution, extracted with CH$_2$Cl$_2$ (3×) and dried over Na$_2$SO$_4$. The crude material was purified on silica gel column using 0-45% of Solvent 2 (Solvent 2=70% CH$_2$Cl$_2$, 30% MeOH, 5% NH$_4$OH) in CH$_2$Cl$_2$ as eluent affording 55 mg (59%) of the product 27 as a white foam. $^1$H NMR (400 MHz, CDCl$_3$, ppm) δ: 8.43 (d, J=4.7 Hz, 1H), 7.34-7.18 (m, 6H), 7.02 (dd, J=7.7, 4.6 Hz, 1H), 6.64 (d, J=5.1 Hz, 1H), 4.86 (dt, J=10.4, 5.3 Hz, 1H), 3.96 (dd, J=9.3, 5.7 Hz, 1H), 2.93 (A of AB, J$_{AB}$=11.0 Hz, 1H), 2.81-1.59 (m, 32H), 1.51-1.33 (m, 4H). $^{19}$F NMR (376 MHz, CDCl$_3$, ppm) δ: -94.19 (d, J=236.6 Hz), -101.39 (d, J=235.3 Hz).

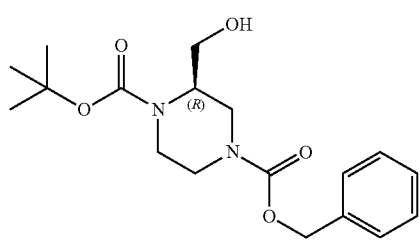

28

(2S)-4-Benzyloxycarbonyl-1-tert-butoxycarbonyl-piperazine-2-carboxylic acid (5.0 g, 13.72 mmol) was dissolved in anhydrous THF (70 mL) and cooled to 0° C. with an ice bath. Borane dimethyl sulfide complex (2.6 mL, 27.44 mmol) was added dropwise at 0° C., slowly. Then the reaction solution was left to warm up to room temperature and stirred overnight. The reaction mixture was then cooled to 0° C. with an ice bath and quenched with water, dropwise, and extracted with EtOAc. The aqueous phase was extracted with DCM (2×). Combined organic layers were dried over anhydrous MgSO$_4$, filtered and evaporated under reduced pressure. It was used without further purification.

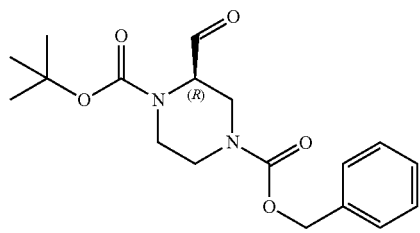

29

Compound 28 (4.74 g, 13.53 mmol) was dissolved in anhydrous DCM (45 mL) and triethylamine (7.54 mL, 54.11 mmol) added and the mixture was cooled to 0° C. A solution of pyridine sulfur trioxide (6.46 g, 40.58 mmol) in DMSO (45 mL) was added at 0° C. and stirred for 1 hour. The reaction was quenched with a saturated NaHCO$_3$ solution and diluted with ether. The aqueous phase was extracted with ether (3×). Combined organic layers were extracted with sodium phosphate dibasic (Na$_2$HPO$_4$), 1M HCl and brine; dried over anhydrous Na$_2$SO$_4$, filtered and evaporated. The crude product was used for the next step without purification.

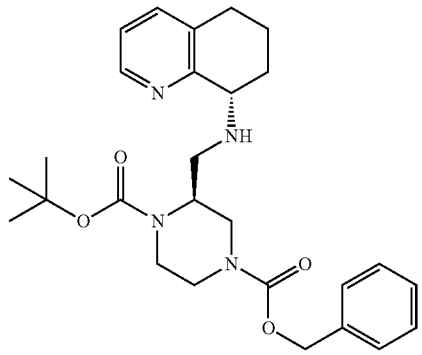

30

(S)-5,6,7,8-Tetrahydroquinolin-8-amine (2.2 g, 14.84 mmol) was dissolved in DCE (100 mL) and STAB-H (5.72 g, 26.98 mmol) added at room temperature. The reaction mixture was stirred for a few minutes then 29 (4.7 g, 13.49 mmol) was added and the mixture was stirred at room temperature overnight. The reaction mixture was quenched with a saturated NaHCO$_3$ solution. The aqueous phase was extracted with DCM and combined organic layers were dried over anhydrous MgSO$_4$, filtered and evaporated. The desired product was purified with column chromatography using DCM:MeOH:NH$_3$ (9:1:0.2) giving 5.74 g (86% yield).

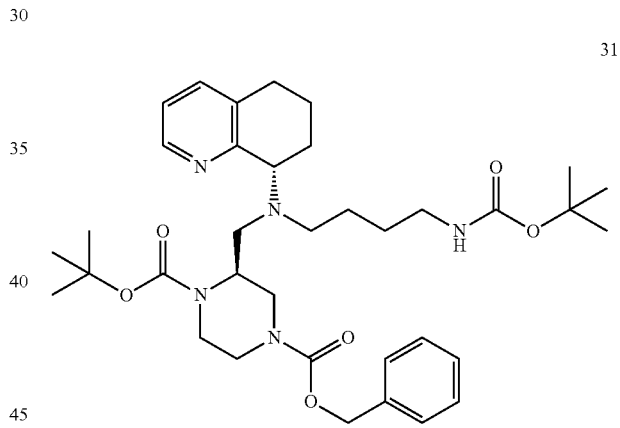

31

Compound 30 (3.04 g, 6.33 mmol), 1.78 g of tert-butyl (4-oxobutyl)carbamate (1.78 g, 9.49 mmol) and DCE (30 ml). Then NaBH(OAc)$_3$ (2.68 g, 12.7 mmol), and acetic acid (0.38 g, 6.33 mmol) were added. After stirring at room temperature for 48 h, the reaction mixture was quenched by addition of a sat. NaHCO$_3$ solution and the product was extracted with DCM (3×) and dried over anhydrous MgSO$_4$. The crude product was purified on silica gel column using 0-100% EA in hexanes as eluent affording 2.21 g (53%) as a clear oil.

Compound 31 (1.2 g, 1.84 mmol) was dissolved in ethanol (30.682 mL) and ammonium formate (0.46 g, 7.36 mmol) and palladium hydroxide on carbon (0.26 g, 0.3700 mmol) were added at room temperature. The reaction mixture was stirred at room temperature for 1 hour and then filtered over celite and evaporated. The crude product 5 was used for the next step without purification.

32

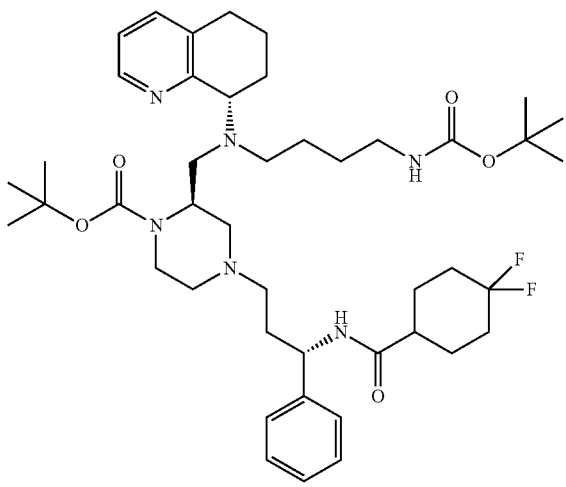

Compound 5 (0.41 g, 0.79 mmol) and STAB-H (0.34 g, 1.58 mmol) were suspended in DCM (20 ml) and stirred for a few minutes at room temperature and then 4,4-difluoro-N-[(1S)-3-oxo-1-phenyl-propyl]cyclohexanecarboxamide 6 (0.23 g, 0.7900 mmol) was added and the reaction mixture was stirred overnight. It was quenched with a saturated NaHCO$_3$ solution. The aqueous phase was extracted with DCM and combined organic layers were dried over anhydrous Na$_2$SO$_4$, filtered and evaporated. The crude product was purified with column chromatography starting with DCM and increased the polarity with DCM:MeOH:NH$_3$ (9:1:0.2) slowly to 50% as eluent affording 0.37 g (59% over two steps) of 32 as clear oil.

2

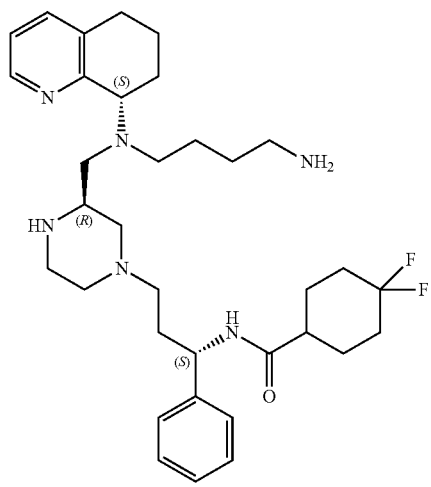

Compound 32 (0.19 g, 0.2300 mmol) was dissolved in DCM (5 mL) and TFA (0.36 mL, 4.65 mmol) was added at room temperature. The reaction mixture was stirred overnight and then basified with 1 N NaOH to pH>12. The organic layer was separated and the aqueous layer was extracted with DCM (3×). The combined organic layers were dried over anhydrous MgSO$_4$, filtered and evaporated. The product was purified with column chromatography starting with DCM and increased the polarity slowly to DCM:MeOH:NH$_3$ (8:2:0.6) as eluent affording 85 mg (61% yield) as a colorless foam. $^1$H NMR (500 MHz, Chloroform-d) δ 8.41 (dd, J=4.8, 1.8 Hz, 1H), 8.26 (d, J=7.0 Hz, 1H), 7.31 (dd, J=7.8, 1.7 Hz, 1H), 7.26 (d, J=7.6 Hz, 1H), 7.19 (d, J=7.4 Hz, 3H), 7.01 (dd, J=7.6, 4.7 Hz, 1H), 4.99 (q, J=6.2 Hz, 1H), 4.01 (dd, J=10.2, 6.3 Hz, 1H), 3.05-2.98 (m, 2H), 2.88-2.83 (m, 2H), 2.71 (td, J=11.3, 9.3, 3.8 Hz, 6H), 2.51 (dt, J=12.9, 6.3 Hz, 1H), 2.32-2.18 (m, 3H), 2.16-1.98 (m, 6H), 1.99-1.88 (m, 4H), 1.85-1.59 (m, 9H), 1.57-1.35 (m, 6H).

33

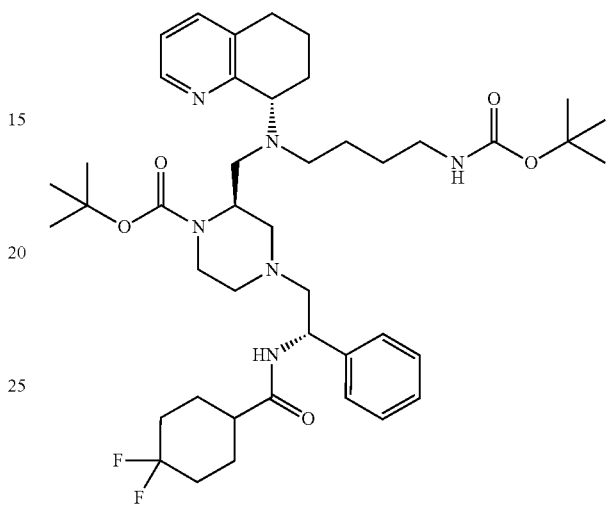

Compound 5 (0.43 g, 0.8300 mmol) and STAB-H (0.35 g, 1.66 mmol) were suspended in DCM and stirred at room temperature for a few minutes. Then the aldehyde 21 (0.23 g, 0.8300 mmol) was added. The reaction mixture was stirred at room temperature overnight. During the reaction, an aldol reaction (546 in LC/MS), racemization of the aldehyde, and kinetic resolution proceeded (the amine prefers S aldehyde) affording 1:3 (R/S) of the isomers. The reaction mixture was quenched by addition of sat. NaHCO$_3$ solution, extracted with DCM (3×) and dried over Na$_2$SO$_4$. The crude product was purified on silica gel column using 0 to 100% EA in hexanes as eluent affording 185 mg (29% yield) of desired isomer 33 as a white foam.

34

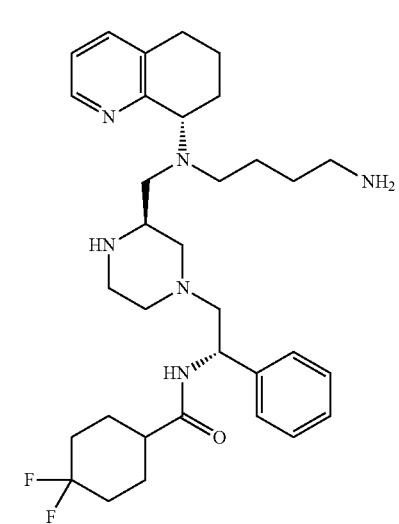

Compound 33 (0.185 g, 0.24 mmol) was dissolved in DCM (5 mL) and TFA (0.23 mL, 4.73 mmol) was added at room temperature. The reaction mixture was stirred overnight and was then basified with 1 N NaOH to pH>12. The organic layer was separated and the aqueous layer was extracted with DCM (3×). Combined organic layers were dried over anhydrous MgSO$_4$, filtered and evaporated. The crude product was purified with column chromatography starting with DCM and increasing the polarity slowly to DCM:MeOH:NH$_3$ (8:2:0.6) as eluent affording 52 mg (38% yield) of compound 34 as a white foam. $^1$H NMR (500 MHz, Chloroform-d) δ 8.44 (d, J=4.7 Hz, 1H), 7.32 (d, J=7.8 Hz, 1H), 7.27 (d, J=4.2 Hz, 4H), 7.19 (hept, J=4.2 Hz, 1H), 7.07 (s, 1H), 7.00 (dd, J=7.7, 4.7 Hz, 1H), 4.91 (dt, J=10.8, 5.1 Hz, 1H), 4.04 (dd, J=9.9, 6.3 Hz, 3H), 2.97 (dt, J=11.7, 2.6 Hz, 1H), 2.89-2.74 (m, 2H), 2.80-2.72 (m, 3H), 2.66 (ddt, J=27.2, 15.5, 7.5 Hz, 7H), 2.52 (dd, J=13.4, 5.2 Hz, 1H), 2.42-2.30 (m, 2H), 2.25 (dd, J=13.3, 7.5 Hz, 1H), 2.18-2.01 (m, 4H), 2.01-1.86 (m, 4H), 1.76-1.50 (m, 9H).

reaction was stirred at room temperature overnight. During reaction, an aldol reaction (546 in LC/MS), racemization of the aldehyde, and kinetic resolution proceeded (the amine prefers S aldehyde) affording 1:3 (RS) of the isomers. The reaction mixture was quenched by addition of a sat. NaHCO$_3$ solution, extracted with DCM (3×) and dried over Na$_2$SO$_4$. The crude product was purified on silica gel column using 0 to 100% EA in hexanes as eluent affording 40 mg (7% yield) of desired isomer 35 as a white foam.

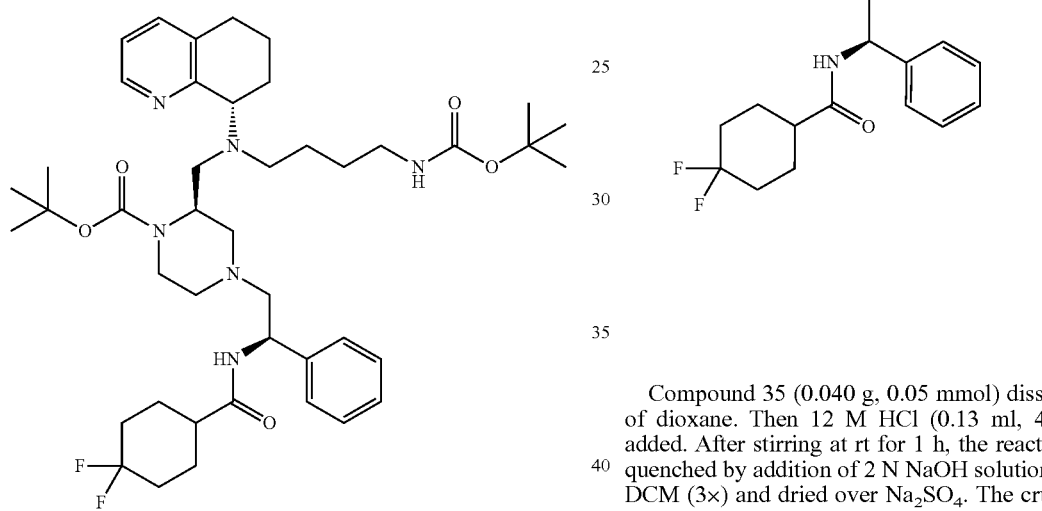

Compound 5 (0.41 g, 0.7900 mmol) was dissolved in DCM and STAB-H (0.34 g, 1.58 mmol) was added to the solution. After stirring for a few minutes the aldehyde 24 (0.22 g, 0.7900 mmol) was added to the mixture. The Compound 35 (0.040 g, 0.05 mmol) dissolved in 1.5 mL of dioxane. Then 12 M HCl (0.13 ml, 4.79 mmol) was added. After stirring at rt for 1 h, the reaction mixture was quenched by addition of 2 N NaOH solution, extracted with DCM (3×) and dried over Na$_2$SO$_4$. The crude product was purified with column chromatography starting with DCM and increasing the polarity slowly to DCM:MeOH:NH$_3$ (8:2:0.6) as eluent affording 3 mg (10% yield) of compound 36 as a colorless foam. $^1$H NMR (600 MHz, Chloroform-d) δ 8.32 (d, J=4.6 Hz, 1H), 7.30-7.27 (m, 2H), 7.24 (t, J=7.6 Hz, 2H), 7.15 (t, J=7.4 Hz, 2H), 7.03-6.95 (m, 1H), 6.36 (s, 1H), 4.83 (s, 1H), 3.97 (dd, J=10.0, 6.2 Hz, 1H), 3.00 (s, 1H), 2.78-2.66 (m, 5H), 2.64-2.58 (m, 1H), 2.58-2.44 (m, 4H), 2.25-2.15 (m, 1H), 2.13-2.02 (m, 2H), 2.00-1.95 (m, 1H), 1.94-1.82 (m, 4H), 1.79-1.69 (m, 4H), 1.25-1.13 (m, 7H), 0.97 (t, J=7.2 Hz, 3H), 0.85-0.73 (m, 2H).

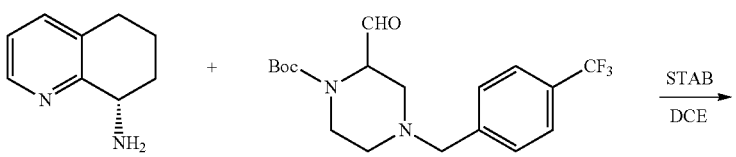

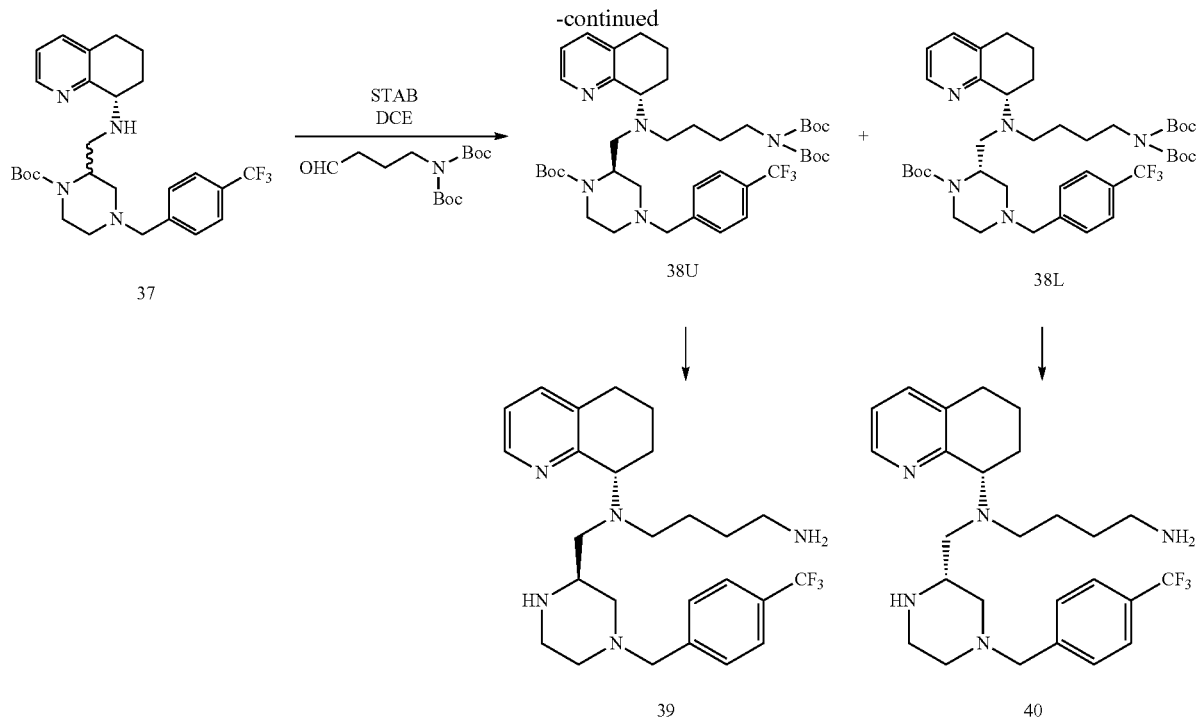

37: (S)-5,6,7,8-tetrahydroquinolin-8-amine (0.647 g, 4.36 mmol) and tert-butyl 2-formyl-4-(4-(trifluoromethyl)benzyl)piperazine-1-carboxylate (1.3 g, 3.49 mmol) were dissolved in 1,2-DCE and stirred for a few minutes. Then STAB (1.110 g, 5.24 mmol) was added and the reaction was stirred overnight at room temperature. The reaction mixture was quenched with saturated $NaHCO_3$ solution and extracted with DCM (3×). Combined organic layers were washed with water then brine; dried over anhydrous $MgSO_4$, filtered off and evaporated. The crude product was purified with column chromatography starting with DCM and increasing the polarity with $DCM:MeOH:NH_4OH$ (9:1:0.1) to 50% as eluent affording 1.25 g (71%) of the product 37 as a white foam.

38U and 38L: Compound 37 (1.25 g, 2.477 mmol) was dissolved in 1,2-DCE and N,N-diboc butyraldehyde (0.890 g, 3.10 mmol) was added and the reaction was stirred for few minutes. Then STAB (0.788 g, 3.72 mmol) was added and the reaction mixture was stirred overnight. The reaction was quenched with saturated $NaHCO_3$ solution and extracted with DCM, combined organic layers were washed with water, then brine and dried over anhydrous $MgSO_4$; then filtered off and evaporated. The diasteromers were separated using column chromatography starting with Hexanes and increasing the polarity with EtOAc.

39: Compound 38U (0.340 g, 0.44 mmol) was dissolved in 4 ml DCM and TFA (1.0 ml, 13.15 mmol) added and the mixture stirred overnight at room temperature. The reaction mixture was basified with 3.75 N NaOH solution (pH>12-14). Then extracted with DCM many times. Combined organic phases were dried over anhydrous $MgSO_4$; filtered off and evaporated. The crude product was purified with column chromatography starting with DCM and increased the polarity with $DCM:MeOH:NH_4OH$ (8:2:0.3) as eluent affording 0.15 g (72%) of the product 39 as a white foam.

40: Compound 38L Reactant 1 (0.5 g, 0.644 mmol) was dissolved in 5 ml DCM and TFA (1.5 ml, 19.33 mmol) added and the reaction stirred overnight at room temperature. The reaction mixture was basified with 3.75 N NaOH solution and extracted with DCM many times. Combined organic layers were dried over anhydrous $MgSO_4$; filtered off and evaporated. The crude product was purified with column chromatography starting with DCM and increasing the polarity with $DCM:MeOH:NH_4OH$ (8:2:0.3) as eluent affording 0.22 g (72%) of the product 40 as a white foam.

A 50 mL rb flask equipped with an air condenser, rubber septum and a magnetic stir bar was set under Ar atmosphere and charged with 500 mg of 1-(tert-butoxycarbonyl)piperazine-2-carboxylic acid (2.17 mmol, 1 equiv.), 80.0 mg of DMAP (0.651 mmol, 0.3 equiv.), 500 mg of EDCI (2.61 mmol, 1.2 equiv.), 10 mL of $CH_2Cl_2$ and 3 mL of dry methanol. The reaction mixture was stirred at 40° C. for 1.5 h and then the reaction was allowed to cool to rt. After stirring for 20 h, the reaction mixture was concentrated and the residue was dissolved in $CH_2Cl_2$. The $CH_2Cl_2$ solution was washed with water (3×). The water solutions were combined and the product was back-extracted with $CH_2Cl_2$ (3×). Then the combined organics were washed with sat. $NaHCO_3$ solution, brine and dried over $Na_2SO_4$. The crude product (661 mg) was purified on silica gel column using 0 to 5% MeOH in $CH_2Cl_2$ as eluent affording 419 mg (79%) of the product 41 as a colorless oil.

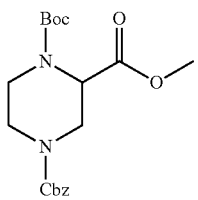

42

A 25 mL rb flask equipped with a rubber septum and a magnetic stir bar was set under an Ar atmosphere and charged with 840 mg of 1-tert-butyl 2-methyl piperazine-1,2-dicarboxylate 42 (3.44 mmol, 1 equiv.) dissolved in 6.9 mL of CH$_2$Cl$_2$. After the reaction mixture was cooled to 0° C., 0.527 mL of TEA (3.78 mmol, 1.1 equiv.) and 0.515 mL of CbzCl (3.61 mmol, 1.05 equiv.) were added dropwise and the reaction mixture was stirred for 30 min. Then the reaction mixture was allowed to warm to rt and stirring was continued for 2 h. The reaction mixture was quenched by addition of sat. NH$_4$Cl solution, extracted with CH$_2$Cl$_2$ (2×), washed with sat. NaHCO$_3$ solution (2×), brine and dried over Na$_2$SO$_4$. The crude product was purified on silica gel column using 30% EA in hexanes as eluent affording 986 mg (76%) of the product 42 as a colorless oil.

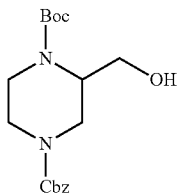

43

A 50 mL rb flask equipped with a rubber septum and magnetic stir bar was charged with 460 mg of CaCl$_2$ (4.14 mmol, 1.6 equiv.) followed by 980 mg of 4-benzyl 1-tert-butyl 2-methyl piperazine-1,2,4-tricarboxylate (2.59 mmol, 1 equiv.) dissolved in 26 mL of 1:1 mixture of THF and EtOH. After stirring at rt for 20 min, the clear solution was cooled to 0° C. and 416 mg of NaBH$_4$ (11.0 mmol, 4.25 equiv.) was added and the suspension was stirred at 0° C. for 30 min. Then the reaction mixture was allowed to warm to rt and the stirring was continued for 12 h. The reaction was quenched by addition of 1 M HCl till no bubbling was observed (pH paper showed neutral solution) and the product was extracted with diethyl ether (3×), washed with water (2×), brine and dried over Na$_2$SO$_4$. The crude product was purified on silica gel column using 10 to 30% EA in hexanes as eluent affording 891 mg (98%) of product 43 as a clear oil.

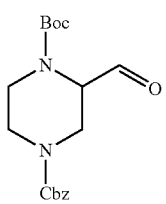

44

A 100 mL rb flask equipped with a rubber septum and magnetic stir bar was charged with 28 mL of CH$_2$Cl$_2$ and 0.497 mL of oxalyl chloride (5.68 mmol, 2.25 equiv.) and the solution was cooled to −78° C. Then 0.807 mL of DMSO (11.4 mmol, 4.5 equiv.) was added dropwise. After stirring for 30 min, 0.885 g of 4-benzyl 1-tert-butyl 2-(hydroxymethyl)piperazine-1,4-dicarboxylate 43 (2.53 mmol, 1 equiv.) dissolved in 13 mL of CH$_2$Cl$_2$ was added dropwise and the reaction mixture was stirred for 1 h. Then 1.58 mL of NEt$_3$ (11.4 mmol, 4.5 equiv.) was added dropwise. After stirring at −78° C. for 20 min, the reaction mixture was allowed to warm to 0° C. and the stirring was continued for 1 h. The reaction was quenched by addition of sat. NaHCO$_3$ solution and the product was extracted with CH$_2$Cl$_2$ (3×), washed with water, brine and dried over Na$_2$SO$_4$. The solution was concentrated and filtered through a silica gel plug using 50% EA in hexanes as eluent. The crude product was purified on silica gel column using CH$_2$Cl$_2$, then 10% EA in CH$_2$Cl$_2$ as eluent affording 773 mg (88%) of the product 44 as a slightly yellow oil.

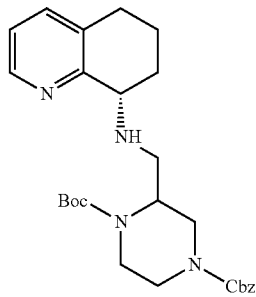

45

To a 20 mL vial equipped with a rubber septum and stir bar was added 323 mg of the aldehyde 44 (0.927 mmol, 1 equiv.) and 206 mg of (S)-5,6,7,8-tetrahydroquinolin-8-amine (1.39 mmol, 1.5 equiv.) dissolved in 6.2 mL DCE. After stirring at rt for 2.5 h, 331 mg of NaBH(OAc)$_3$ (1.48 mmol, 1.6 equiv.) was added in one portion and the suspension was stirred at rt for 2 h. Then the reaction mixture was quenched by addition of 1N K$_2$CO$_3$ solution and the product was extracted with CH$_2$Cl$_2$ (3×), washed with 1N K$_2$CO$_3$ solution, brine and dried over Na$_2$SO$_4$. The crude product was purified on silica gel column using CH$_2$Cl$_2$, then 3% MeOH in CH$_2$Cl$_2$ as eluent affording 444 mg (100%) of the product 45 as a slightly yellow oil.

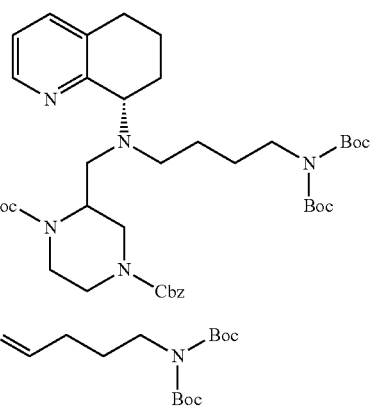

46

47

A 20 mL vial was charged with 440 mg of the amine 45 (0.916 mmol, 1 equiv.) and 526 mg of the aldehyde 47 (1.83 mmol, 2 equiv.), followed by addition of 126 µL of AcOH (2.11 mmol, 2.3 equiv.) and the mixture was stirred at rt for 2 h. Then 408 mg of NaBH(OAc)$_3$ (1.83 mmol, 2 equiv.) was added. After stirring at rt for 1.5 h, the reaction mixture was washed with 1N K$_2$CO$_3$ (3×). The combined aq. layer was extracted with CH$_2$Cl$_2$ (3×) and the combined organics were washed with brine and dried over Na$_2$SO$_4$. The crude product (1.06 g) was purified on silica gel column using 10-60% EA in hexanes, then 10% MeOH in CH$_2$Cl$_2$ as eluent affording 327 mg (48%) of URf (R,S) isomer of 46U and 333 mg (48%) of LRf (S,S) isomer of 46L as clear oils.

48

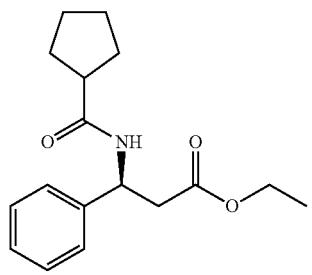

A 10 mL rb flask equipped with a stir bar and septum was charged with 300 mg of ethyl (S)-3-amino-3-phenylpropanoate hydrochloride (1.31 mmol, 1 equiv.), 16.0 mg of DMAP (0.131 mmol, 0.1 equiv.) and 419 µL of NEt$_3$ (3.00 mmol, 2.3 equiv.) dissolved in 1.1 mL of CH$_2$Cl$_2$ at 0° C. Then 175 µL of cyclopentanecarbonyl chloride (1.44 mmol, 1.1 equiv.) was added dropwise. After stirring at 0° C. for 2 h, the reaction mixture was quenched by addition of sat. NH$_4$Cl solution, extracted with Et$_2$O (3×) and dried over Na$_2$SO$_4$. The crude product was purified on silica gel column using 10-20% EA in hexanes as eluent affording 364 mg (96%) of the product 48 as a clear oil which crystallizes to white solid.

49

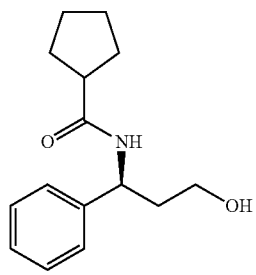

A 100 mL rb flask equipped with a rubber septum and magnetic stir bar was charged with 141 mg of LiAlH$_4$ (3.71 mmol, 1 equiv.) and 27 mL THF and the reaction mixture was cooled to 0° C. Then 1.07 g of the ester 48 (3.71 mmol, 1 equiv.) dissolved in 10 mL of THF was added. After stirring at 0° C. for 15 min, the suspension was quenched by addition of water and the product was extracted with diethyl ether (3×), washed with water, brine and dried over Na$_2$SO$_4$. The crude product (1.19 g) was purified on silica gel column using 50% EA in hexanes, then 5% MeOH in CH$_2$Cl$_2$ as eluent affording 809 mg (88%) of product 49 as a white solid.

50

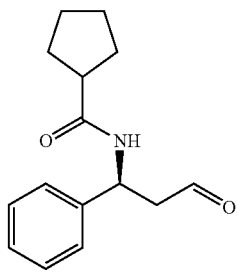

A 50 mL rb flask equipped with a rubber septum and magnetic stir bar was charged with 9.8 mL of CH$_2$Cl$_2$ and 0.427 mL of oxalyl chloride (4.91 mmol, 1.5 equiv.) and the solution was cooled to −78° C. Then 0.696 mL of DMSO (9.81 mmol, 3 equiv.) was added dropwise. After stirring for 20 min, 0.908 g of the alcohol 49 (3.27 mmol, 1 equiv.) dissolved in 10.9 mL of CH$_2$Cl$_2$ was added dropwise and the reaction mixture was stirred for 15 min. Then 1.82 mL of NEt$_3$ (13.1 mmol, 4 equiv.) was added dropwise. After stirring at −78° C. for 5 min, the reaction mixture was allowed to warm to 0° C. The reaction mixture was quenched by addition of sat. NH$_4$Cl solution and the product was extracted with CH$_2$Cl$_2$ (3×), washed with brine and dried over Na$_2$SO$_4$. The crude product was purified on silica gel column using 30-50% EA in hexanes as eluent affording 429 mg (48%) of the product 50 as a white solid.

51L

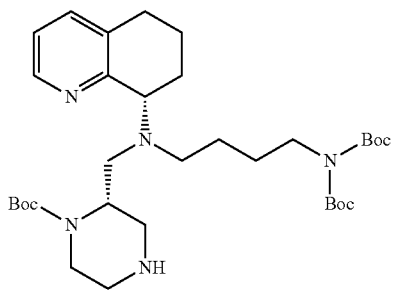

A 20 mL vial equipped with a stir bar and septum was charged with 102 mg of the amine 46L (0.136 mmol, 1 equiv.), 24.0 mg of PdCl$_2$ (0.136 mmol, 1 equiv.), 38 µL of triethylamine (0.271 mmol, 2 equiv.) and 1.0 mL of CH$_2$Cl$_2$. Then 50 µL of triethylsilane (0.312 mmol, 2.3 equiv.) was added dropwise and the solution turned to black suspension. After stirring at rt for 12 h, the reaction mixture was quenched by addition of saturated NH$_4$Cl aq. solution, extracted with diethyl ether (3×), washed with sat. NH$_4$Cl aq. solution, brine and dried over Na$_2$SO$_4$. The crude product was purified on silica gel column using 0-20% MeOH in CH$_2$Cl$_2$, then 20% MeOH and 2% NH$_4$OH in CH$_2$Cl$_2$ as eluent affording 74 mg (88%) of the product 51L as a clear oil.

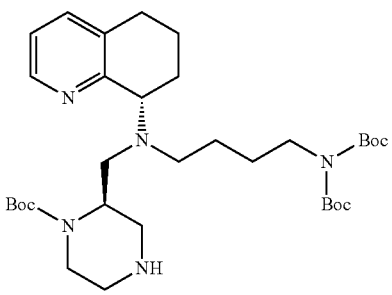

51U

A 3 mL vial equipped with a stir bar and septum was charged with 168 mg of the amine 46U (0.223 mmol, 1 equiv.), 40 mg of PdCl$_2$ (0.223 mmol, 1 equiv.) and 62 µL of triethylamine (0.447 mmol, 2 equiv.). Then 1.07 mL of triethylsilane (6.70 mmol, 30 equiv.) was added dropwise and the solution turned into a black suspension. After stirring at rt for 30 min, the reaction mixture was quenched by addition of saturated NH$_4$Cl solution. After stirring for 30 min, sat. Na$_2$CO$_3$ solution was added, extracted with CH$_2$Cl$_2$ (3×), washed with brine and dried over Na$_2$SO$_4$. The crude product was purified on silica gel column using 0-10% MeOH in CH$_2$Cl$_2$, then 20% MeOH and 1% NH$_4$OH in CH$_2$Cl$_2$ as eluent affording 137 mg (100%) of the product 51U as a clear oil.

52U

To a 20 mL vial equipped with a septum and stir bar was added 48 mg of the aldehyde 50 (0.198 mmol, 1.1 equiv.) and 111 mg of amine 51U (0.180 mmol, 1 equiv.) dissolved in 1.8 mL CH$_2$Cl$_2$. After adding 13 µL of acetic acid (0.234 mmol. 1.3 equiv.) and stirring at rt for 2 h, 48 mg of NaBH(OAc)$_3$ (0.225 mmol, 1.25 equiv.) was added in one portion and the suspension was stirred at rt for 1.5 h. Then the reaction mixture was quenched by addition of sat. Na$_2$CO$_3$ solution and the product was extracted with CH$_2$Cl$_2$ (3×) and dried over Na$_2$SO$_4$. The crude product was purified on silica gel column using 50-100% EA in hexanes, then 1% NH$_4$OH in EA as eluent affording 107 mg (70%) of the product 52U as a clear oil.

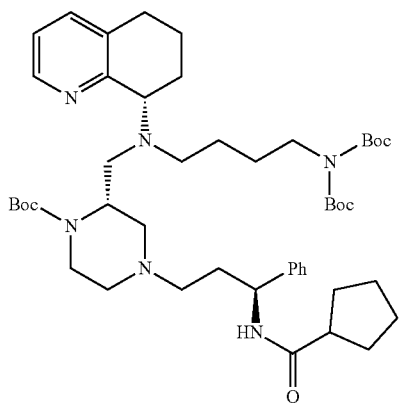

52L

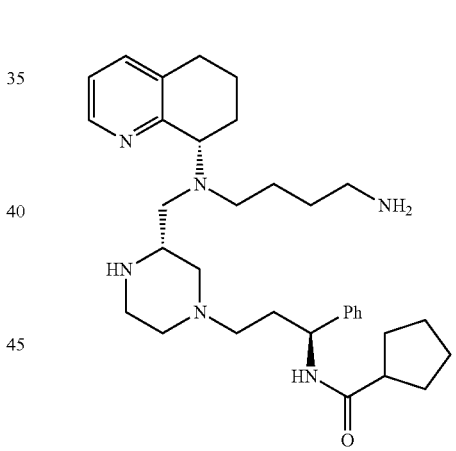

53L

To a 20 mL vial equipped with a septum and stir bar was added 57 mg of the aldehyde 50 (0.233 mmol, 1.2 equiv.), and 120 mg of amine 51L (0.194 mmol, 1 equiv.) dissolved in 1.9 mL CH$_2$Cl$_2$. After adding 16 µL of acetic acid (0.272 mmol. 1.4 equiv.) and stirring at rt for 2 h, 54 mg of NaBH(OAc)$_3$ (0.253 mmol, 1.3 equiv.) was added in one portion and the suspension was stirred at rt for 12 h. Then the reaction mixture was quenched by addition of 1 N K$_2$CO$_3$ solution and the product was extracted with CH$_2$Cl$_2$ (2×), washed with 1 N K$_2$CO$_3$ solution, brine and dried over Na$_2$SO$_4$. The crude product was purified on silica gel column using 30-100% EA in hexanes, then 0.5-1% NH$_4$OH in EA as eluent affording 124 mg (75%) of the product 52L as a clear oil.

To a 20 mL vial equipped with a septum and stir bar was added 59 mg of the amine 52L (0.070 mmol, 1 equiv.) and 1.4 mL CH$_2$Cl$_2$. After adding 161 µL of CF$_3$COOH (2.09 mmol, 30 equiv.) and stirring at rt for 12 h, the reaction mixture was quenched by addition of 2 N NaOH solution and the product was extracted with CH$_2$Cl$_2$ (3×), and dried over Na$_2$SO$_4$. The crude product was purified on silica gel column using 0-10% MeOH in CH$_2$Cl$_2$, then 30% MeOH in CH$_2$Cl$_2$ with 1-2% NH$_4$OH as eluent affording 28 mg (74%) of the product 53L as a slightly yellow glassy oil. (after scratching a powder is obtained). $^1$H NMR (400 MHz, CDCl$_3$, ppm) δ: 8.44 (dd, J=4.7, 1.7 Hz, 1H), 7.95 (d, J=7.2 Hz, 1H), 7.36-7.17 (m, 6H), 7.03 (dd, J=7.7, 4.6 Hz, 1H), 5.09 (q, J=6.0 Hz, 1H), 3.98 (dd, J=9.5, 5.7 Hz, 1H), 3.03 (dt, J=11.5, 2.8 Hz, 1H), 2.90 (d, J=11.2 Hz, 1H), 2.85-2.45 (m, 14H), 2.36 (ddd, J=13.7, 9.2, 4.8 Hz, 1H), 2.25 (dt, J=12.8, 5.1 Hz, 1H), 2.14-1.35 (m, 21H).

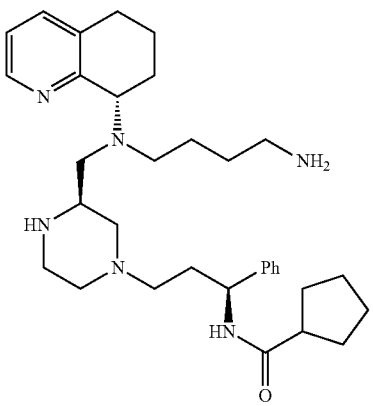

53U

The same procedure as for the synthesis of 53L. Starting with 63 mg of the 52U, 41 mg (100%) of the product 53U as slightly yellow glassy oil (after scratching a powder was obtained). $^1$H NMR (400 MHz, CDCl$_3$, ppm) δ: 8.42 (dd, J=4.8, 1.7 Hz, 1H), 7.89 (d, J=7.4 Hz, 1H), 7.36-7.14 (m, 6H), 7.02 (dd, J=7.7, 4.7 Hz, 1H), 5.01 (q, J=6.4 Hz, 1H), 4.01 (dd, J=10.0, 6.2 Hz, 1H), 3.10-2.46 (m, 15H), 2.38-2.26 (m, 2H), 2.22 (dt, J=12.4, 5.6 Hz, 1H), 2.09-1.37 (m, 21H).

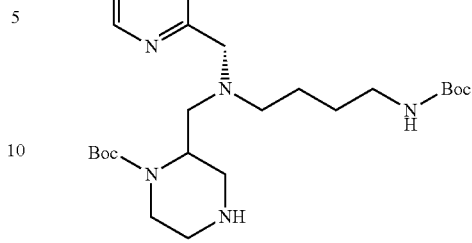

54

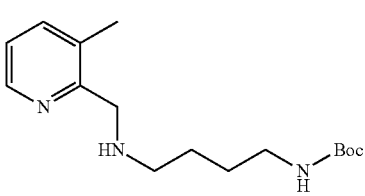

To a 20 mL vial equipped with a septum and stir bar was added 190 mg of the aldehyde 44 (0.545 mmol, 1 equiv.), 176 mg of amine 55 (0.600 mmol, 1.1 equiv.) dissolved in 5.4 mL DCE and 139 mg of NaBH(OAc)$_3$ (0.654 mmol, 1.2 equiv.) was added in one portion and the suspension was stirred at rt for 1.5 h. Then the reaction mixture was quenched by addition of sat. NaHCO$_3$ solution and the product was extracted with CH$_2$Cl$_2$ (3×), washed with brine and dried over Na$_2$SO$_4$. The crude product (439 mg) was purified on silica gel column using EA as eluent affording 289 mg (85%) of the product 54 as a slightly yellow oil.

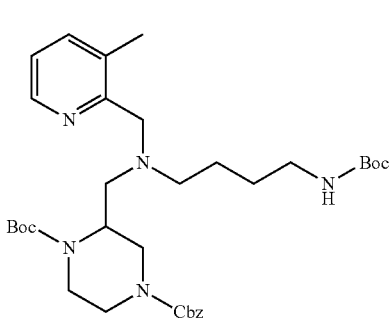

56

A 20 mL vial equipped with a stir bar and septum was charged with 227 mg of the amine 54 (0.363 mmol, 1 equiv.), 32 mg of PdCl$_2$ (0.181 mmol, 0.5 equiv.) and 101 μL of NEt$_3$ (0.725 mmol, 2 equiv.). Then 0.290 μL of triethylsilane (1.81 mmol, 5 equiv.) was added dropwise and the solution turned to black suspension. After stirring at rt for 30 min, the reaction mixture was quenched by addition of 1 N K$_2$CO$_3$ solution, extracted with CH$_2$Cl$_2$ (3×), washed with brine, dried over Na$_2$SO$_4$. The crude product was purified on silica gel column using 0-10% MeOH in CH$_2$Cl$_2$, then 20% MeOH and 1% NH$_4$OH in CH$_2$Cl$_2$ as eluent affording 138 mg (77%) of the product 56 as a clear oil.

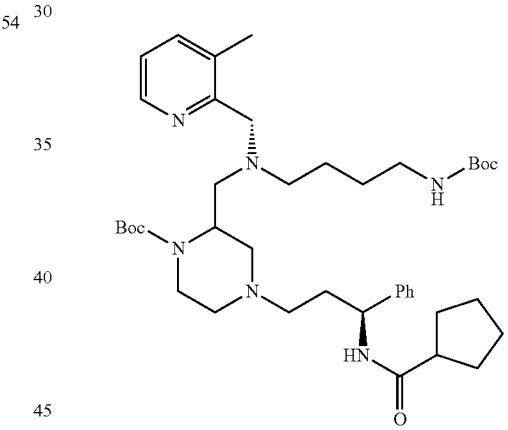

57

To a 20 mL vial equipped with a septum and stir bar was added 76 mg of the aldehyde 50 (0.309 mmol, 1.1 equiv.), 132 mg of amine 56 (0.281 mmol, 1 equiv.) dissolved in 2.8 mL CH$_2$Cl$_2$. After adding 21 μL of acetic acid (0.365 mmol. 1.3 equiv.) and stirring at rt for 1.5 h, 74 mg of NaBH(OAc)$_3$ (0.351 mmol, 1.25 equiv.) was added in one portion and the suspension was stirred at rt for 12 h. Then the reaction mixture was quenched by addition of sat. NH$_4$Cl solution and the product was extracted with CH$_2$Cl$_2$ (3×), washed with saturated NaHCO$_3$ solution, brine and dried over Na$_2$SO$_4$. The crude product was purified on silica gel column using 50-100% EA in hexanes, then 2% NH$_4$OH in EA as eluent affording 201 mg (100%) of the product 57 as a slightly yellow oil.

57

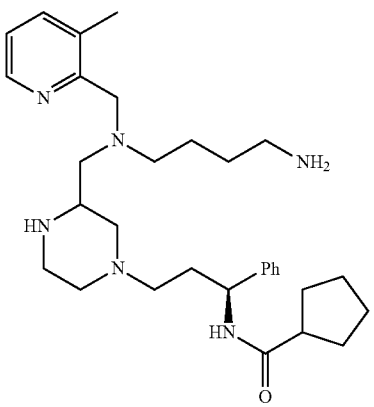

58

To a 20 mL vial equipped with a septum and stir bar was added 105 mg of the amine 57 (0.146 mmol, 1 equiv.) and 3.0 mL CH$_2$Cl$_2$. After adding 337 µL of TFA (4.37 mmol, 30 equiv.) and stirring at rt for 3 h, the reaction mixture was quenched by addition of water, then sat. Na$_2$CO$_3$ solution and 2 N NaOH solution and the product was extracted with EA (3×), and dried over Na$_2$SO$_4$. The crude product was purified on silica gel column using 0-10% MeOH in CH$_2$Cl$_2$, then 30% MeOH in CH$_2$Cl$_2$ with 3% NH$_4$OH as eluent affording 40 mg of the product 58 as a slightly yellow glassy oil. (after scratching a powder was obtained). $^1$H NMR (400 MHz, CDCl$_3$, ppm) δ: 8.36 (s, 0.5H), 8.35 (s, 0.5H), 7.80-7.73 (m, 1H), 7.44-7.39 (m, 1H), 7.33-7.26 (m, 2H), 7.24-7.18 (m, 3H), 7.11 (dd, J=4.9, 1.3 Hz, 0.5H), 7.09 (dd, J=4.9, 1.4 Hz, 0.5H), 5.08 (q, J=7.4 Hz, 1H), 3.80 (A of AB, J$_{AB}$=13.8 Hz, 1H), 3.70 (B of AB, J$_{AB}$=12.9 Hz, 0.5H), 3.67 (B of AB, J$_{AB}$=12.8 Hz, 1H), 3.01-2.95 (m, 1H), 2.91-2.42 (m, 13H), 2.40 (s, 1.5H), 2.39 (s, 1.5H), 2.40-2.26 (m, 1H), 2.27-2.15 (m, 1H), 2.08-1.92 (m, 2H), 1.90-1.27 (m, 15H).

59

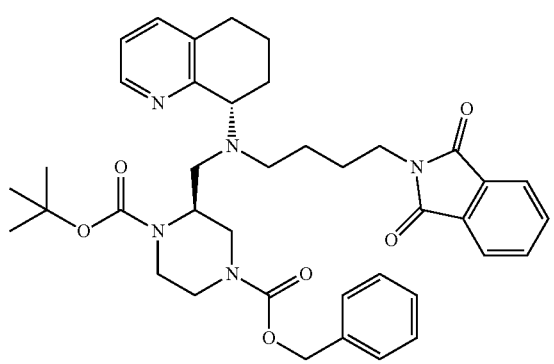

4-Benzyl 1-(tert-butyl) (R)-2-((((S)-5,6,7,8-tetrahydroquinolin-8-yl)amino)methyl)piperazine-1,4-dicarboxylate 30 (4.9 g, 10.2 mmol) was dissolved in DCE (50 mL) and sodium triacetoxyborohydride (5.57 g, 25.49 mmol) added. The reaction was stirred at room temperature for few minutes then 4-(1,3-dioxoisoindolin-2-yl)butanal (2.44 g, 11.22 mmol) was added and then the reaction was stirred at room temperature overnight. The reaction mixture was quenched with saturated NaHCO$_3$ solution and aqueous phase was extracted with DCM 3 times. Combined organic layer was dried over anhydrous MgSO$_4$, filtered off and evaporated.

The desired product 59 was purified with column chromatography using DCM:MeOH:NH$_3$ (9:1:0.2) giving 6.96 g (100% yield).

60

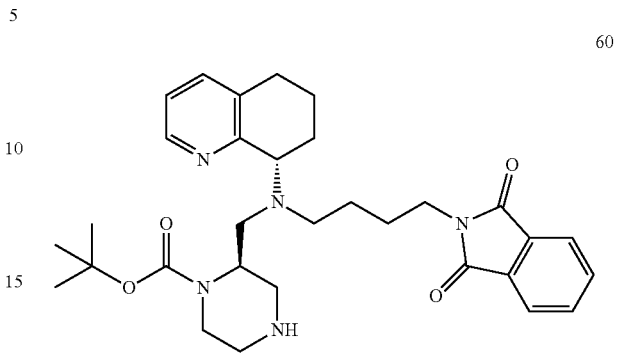

A 500 mL rb flask equipped with a stir bar and rubber septum was charged with 6.96 g of the carbamate 59 (10.2 mmol, 1 equiv.), 1.43 g of 20 w % of Pd(OH)$_2$ on carbon (2.04 mmol, 0.2 equiv.) and 100 mL of dry MeOH (degassed by bubbling Ar for 1 h). Then 2.57 g of NH$_4$O$_2$CH (40.8 mmol, 4 equiv.) was added in one portion. After stirring at rt for 36 h, the reaction mixture was filtered through a celite plug and the celite plug was washed with MeOH. The organics were concentrated in vacuo (rotatory evaporator). Pd catalyst was still present. The crude product was dissolved in CH$_2$Cl$_2$ and washed with 2 N NaOH solution, back-extracted with CH$_2$Cl$_2$ (3×) and dried over Na$_2$SO$_4$. The crude product was purified by silica gel column (120 g) using 0-30% of solvent 2 (solvent 2=30% MeOH in CH$_2$Cl$_{2+3}$% NH$_4$OH) in CH$_2$Cl$_2$ affording 2.70 g (48%) of the product 60 as a yellowish foam.

61

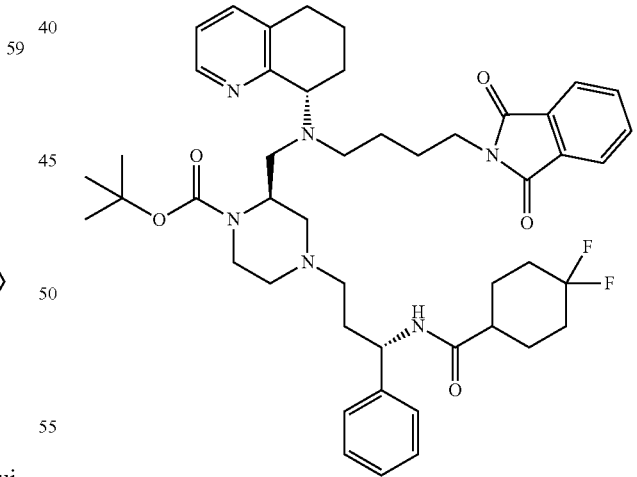

A 250 mL rb flask equipped with a stir bar and septum was charged with 2.70 g of the amine 60 (4.93 mmol, 1 equiv.), 1.75 g of (S)-4,4-difluoro-N-(3-oxo-1-phenylpropyl)cyclohexane-1-carboxamide 6 (5.92 mmol, 1.2 equiv.), 0.056 mL of CH$_3$COOH (0.990 mmol, 0.2 equiv.) and 50 mL of CH$_2$Cl$_2$. Then 1.78 g of NaBH(OAc)$_3$ (8.38 mmol, 1.7 equiv.) was added. After stirring at rt for 12 h, the reaction was not done. 0.440 g of the aldehyde 6 (1.49 mmol, 0.3 equiv.) and the stirring was continued for 12 h. The reaction mixture was quenched by addition of sat. NaHCO₃ solution and sat. Na₂CO₃ sol., and the product was extracted with CH₂Cl₂ (3×) and dried over Na₂SO₄. The crude product was purified on silica gel column (120 g) using 0-100% EA in hexanes as eluent affording 3.35 g (82%) of the product 61 as a yellowish foam.

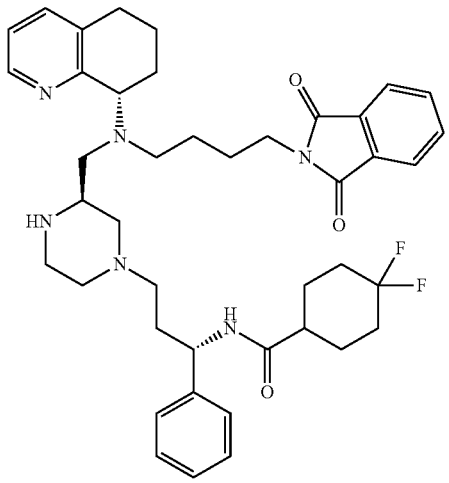

A 250 mL rb flask equipped with a stir bar and septum was charged with 3.12 g of the amine 61 (3.77 mmol, 1 equiv.) dissolved in 38 mL of CH₂Cl₂. Then 8.72 mL of CF₃COOH (113 mmol, 30 equiv.) was added. After stirring at rt for 5 h, the reaction mixture was quenched by addition of sat. Na₂CO₃ solution, extracted with CH₂Cl₂ (3×) and dried over Na₂SO₄. The crude material was purified on silica gel column (80 g) using 0 to 25% of Solvent 2 (solvent 2=70% CH₂Cl₂, 30% MeOH, 3% NH₄OH) in CH₂Cl₂ as eluent affording 1.73 g of the product 62 as a yellowish foam and 0.841 g of the other fraction of the product (broad peaks in NMR) which after re-purification gave 0.760 g of the product (still broad peaks in NMR).

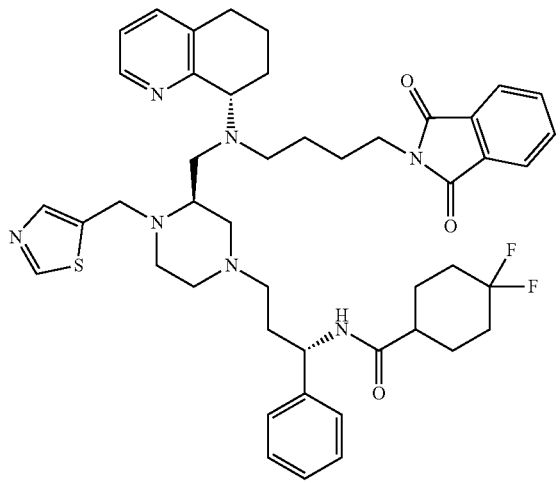

The N-[(1S)-3-[(3R)-3-[[4-(1,3-dioxoisoindolin-2-yl)butyl-[(8S)-5,6,7,8-tetrahydroquinolin-8-yl]amino]methyl]piper-azin-1-yl]-1-phenyl-propyl]-4,4-difluoro-cyclohexanecar-boxamide 62 (250 mg, 0.34 mmol) was dissolved in DCM (5 ml) and added thiazole-5-carbaldehyde (0.04 ml, 0.4100 mmol), acetic acid (0.02 ml, 0.3400 mmol) and then sodium triacetoxyborohydride (116.63 mg, 0.55 mmol) and stirred overnight at room temperature. The reaction mixture was quenched with 1N NaOH solution and aqueous phase was extracted with DCM three times. Combined organic layer was dried over anhydrous MgSO₄, filtered off and evaporated. The desired product 63 was purified with column chromatography using 0-20% MeOH in EtOAc.

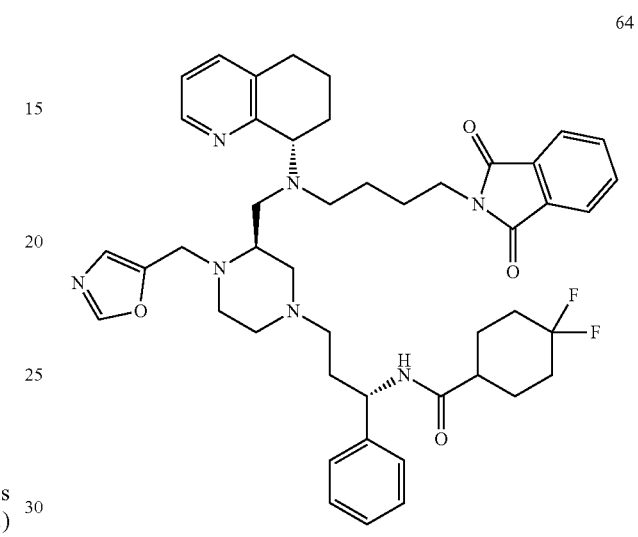

The N-[(1S)-3-[(3R)-3-[[4-(1,3-dioxoisoindolin-2-yl)butyl-[(8S)-5,6,7,8-tetrahydroquinolin-8-yl]amino]methyl]piper-azin-1-yl]-1-phenyl-propyl]-4,4-difluoro-cyclohexanecar-boxamide 62 (0.250 g, 0.34 mmol) was dissolved in DCM (5 ml) and added oxazole-5-carbaldehyde (0.070 g, 0.69 mmol), acetic acid (0.02 ml, 0.3400 mmol) and then sodium triacetoxyborohydride (0.150 g, 0.69 mmol) and stirred overnight at room temperature. The reaction mixture was quenched with 1N NaOH solution and aqueous phase was extracted with DCM three times. Combined organic layer was dried over anhydrous MgSO₄, filtered off and evaporated. The desired product 64 was purified with column chromatography using 0-20% MeOH in EtOAc to get 0.120 g (43% yield).

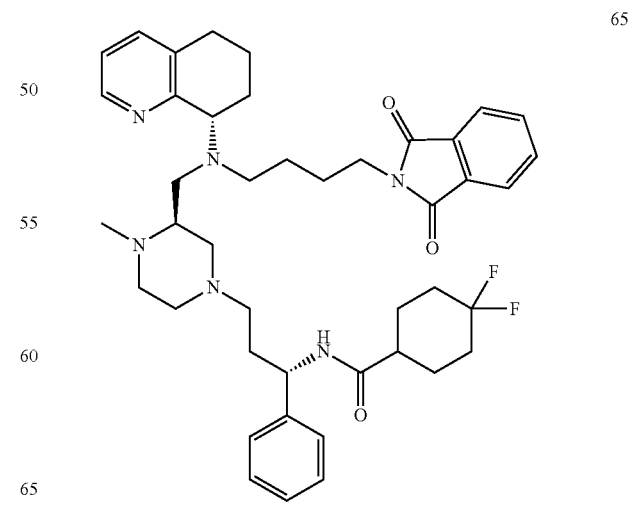

The N-[(1S)-3-[(3R)-3-[[4-(1,3-dioxoisoindolin-2-yl)butyl-[(8S)-5,6,7,8-tetrahydroquinolin-8-yl]amino]methyl]piperazin-1-yl]-1-phenyl-propyl]-4,4-difluoro-cyclohexanecarboxamide 62 (250 mg, 0.34 mmol) was dissolved in DCM (5 ml) and added paraformaldehyde (0.103 g, 3.44 mmol), acetic acid (0.02 ml, 0.34 mmol) and then sodium triacetoxyborohydride (0.150 g, 0.69 mmol) and stirred overnight at room temperature. The reaction mixture was quenched with 1N NaOH solution and aqueous phase was extracted with DCM three times. Combined organic layer was dried over anhydrous $MgSO_4$, filtered off and evaporated. The desired product 65 was purified with column chromatography using 0-20% MeOH in EtOAc to get 0.100 g (39% yield).

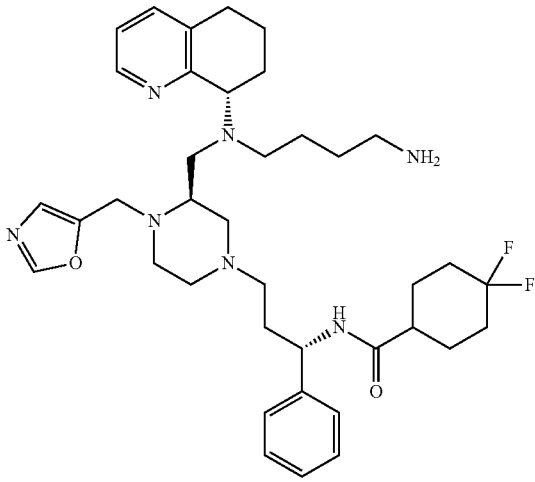

67

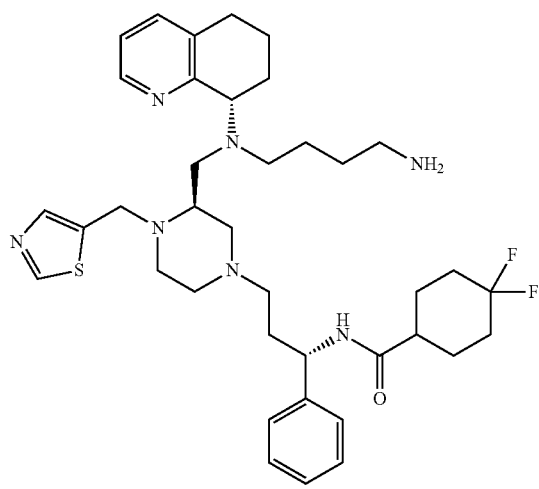

66

N-[(1S)-3-[(3R)-3-[[4-(1,3-dioxoisoindolin-2-yl)butyl-[(8S)-5,6,7,8-tetrahydroquinolin-8-yl]amino]methyl]-4-(oxazol-5-ylmethyl)piperazin-1-yl]-1-phenyl-propyl]-4,4-difluoro-cyclohexanecarboxamide 64 (0.12 g, 0.15 mmol) was dissolved in methanol (2 mL) and then added hydrazine hydrate (0.30 mL, 1.5 mmol) and stirred the reaction overnight. The reaction mixture was quenched with saturated $Na_2CO_3$ solution and extracted with DCM three times. Combined organic layer was dried over anhydrous $MgSO_4$, filtered off and evaporated. The product 67 was purified with DCM:MeOH:$NH_3$ (8:2:0.6) to get 0.071 g (71.5 yield). $^1$H NMR (600 MHz, Chloroform-d) δ 8.49 (d, J=4.6 Hz, 1H), 8.28 (d, J=7.2 Hz, 1H), 7.84 (s, 1H), 7.37 (d, J=7.6 Hz, 1H), 7.29 (d, J=7.2 Hz, 3H), 7.25 (s, 1H), 7.21 (t, J=7.1 Hz, 1H), 7.05 (dd, J=7.6, 4.7 Hz, 1H), 6.95 (s, 1H), 5.01 (q, J=6.6 Hz, 1H), 4.16 (d, J=15.1 Hz, 1H), 4.09 (dd, J=9.3, 6.2 Hz, 1H), 3.60 (d, J=15.1 Hz, 1H), 3.39-3.30 (m, 1H), 2.96 (dd, J=13.2, 3.5 Hz, 1H), 2.84-2.75 (m, 3H), 2.75-2.61 (m, 5H), 2.55 (dt, J=13.3, 6.7 Hz, 2H), 2.48-2.37 (m, 2H), 2.37-2.23 (m, 3H), 2.19-2.05 (m, 5H), 2.05-1.98 (m, 1H), 1.97-1.83 (m, 5H), 1.80-1.64 (m, 4H), 1.62-1.49 (m, 6H).

N-[(1S)-3-[(3R)-3-[[4-(1,3-dioxoisoindolin-2-yl)butyl-[(8S)-5,6,7,8-tetrahydroquinolin-8-yl]amino]methyl]-4-(thiazol-5-ylmethyl)piperazin-1-yl]-1-phenyl-propyl]-4,4-difluoro-cyclohexanecarboxamide 63 (0.17 g, 0.2100 mmol) was dissolved in methanol (2 mL) and then hydrazine hydrate (0.41 mL, 2.06 mmol) was added and the reaction stirred overnight. The reaction mixture was quenched with saturated $Na_2CO_3$ solution and extracted with DCM three times. Combined organic layer was dried over anhydrous $MgSO_4$, filtered off and evaporated. The product 66 was purified with DCM:MeOH:$NH_3$ (8:2:0.6) to get 0.075 g (52.4% yield). $^1$H NMR (600 MHz, Chloroform-d) δ 8.65 (s, 1H), 8.55 (d, J=4.6 Hz, 1H), 8.43 (d, J=7.5 Hz, 1H), 7.61 (s, 1H), 7.31 (d, J=7.7 Hz, 1H), 7.23 (d, J=7.6 Hz, 2H), 7.21-7.18 (m, 2H), 7.11 (t, J=7.2 Hz, 1H), 6.97 (dd, J=7.7, 4.7 Hz, 1H), 4.83 (q, J=7.1 Hz, 1H), 4.20 (d, J=14.5 Hz, 1H), 4.09-4.00 (m, 1H), 3.53 (d, J=14.5 Hz, 1H), 3.05-2.94 (m, 1H), 2.92-2.82 (m, 1H), 2.76-2.63 (m, 6H), 2.55-2.29 (m, 6H), 2.28-2.19 (m, 2H), 2.15 (ddd, J=12.4, 9.1, 5.9 Hz, 1H), 2.07-1.88 (m, 8H), 1.84-1.49 (m, 11H), 1.44 (s, 1H), 1.18 (d, J=7.9 Hz, 1H).

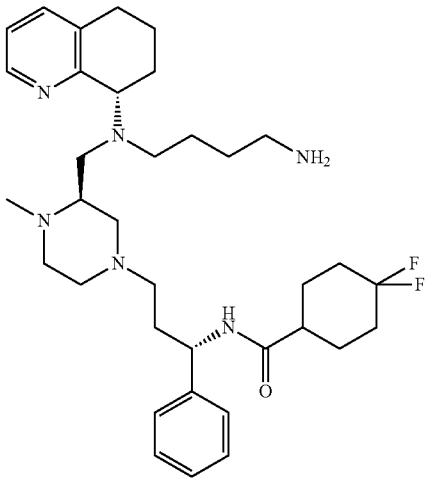

68

N-[(1S)-3-[3-[[4-(1,3-dioxoisoindolin-2-yl)butyl-[(8S)-5,6,7,8-tetrahydroquinolin-8-yl]amino]methyl]-4-methyl-piperazin-1-yl]-1-phenyl-propyl]-4,4-difluoro-cyclohexanecarboxamide 65 (0.1 g, 0.1300 mmol) was dissolved in methanol (2 mL) and hydrazine hydrate (0.27 mL, 1.35 mmol) was added to the solution and stirred the reaction overnight. The reaction mixture was quenched with saturated Na$_2$CO$_3$ solution and extracted with DCM three times. Combined organic layer was dried over anhydrous MgSO$_4$, filtered off and evaporated. The product 68 was purified with DCM:MeOH:NH$_3$ (8:2:0.6) to get 0.043 g (52% yield). $^1$H NMR (600 MHz, Chloroform-d) δ 8.45 (s, 1H), 7.28 (d, J=7.7 Hz, 1H), 7.24-7.16 (m, 5H), 7.13 (t, J=6.9 Hz, 1H), 6.96 (dd, J=7.7, 4.7 Hz, 1H), 4.92 (q, J=6.5 Hz, 1H), 3.99 (dd, J=9.1, 6.2 Hz, 1H), 3.33-3.22 (m, 1H), 2.83-2.54 (m, 10H), 2.52-2.38 (m, 1H), 2.30 (q, J=14.8, 13.7 Hz, 1H), 2.25-2.14 (m, 8H), 2.13-2.02 (m, 3H), 2.02-1.96 (m, 3H), 1.91 (dd, J=9.6, 4.5 Hz, 1H), 1.86-1.64 (m, 6H), 1.59-1.40 (m, 5H), 1.30-1.15 (m, 2H).

69

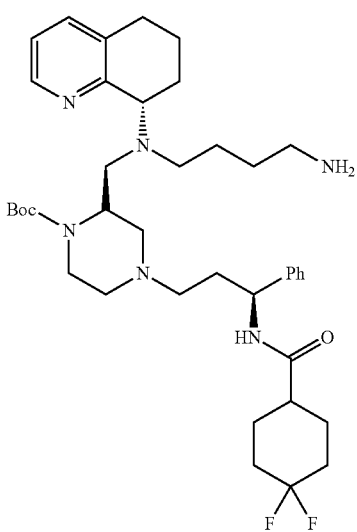

N-[(1S)-3-[(3R)-3-[[4-(1,3-dioxoisoindolin-2-yl)butyl-[(8S)-5,6,7,8-tetrahydroquinolin-8-yl]amino]methyl]-4-(thiazol-5-ylmethyl)piperazin-1-yl]-1-phenyl-propyl]-4,4-difluoro-cyclohexanecarboxamide 61 (0.750 g, 0.91 mmol) was dissolved in methanol (10 mL) and then added hydrazine hydrate (1.80 mL, 9.1 mmol) and stirred the reaction overnight. The reaction mixture was quenched with saturated Na$_2$CO$_3$ solution and extracted with DCM three times. Combined organic layer was dried over anhydrous MgSO$_4$, filtered off and evaporated. The product 69 was purified with DCM:MeOH:NH$_3$ (9:1:0.2). It was yielded 0.495 g (78.3%).

70

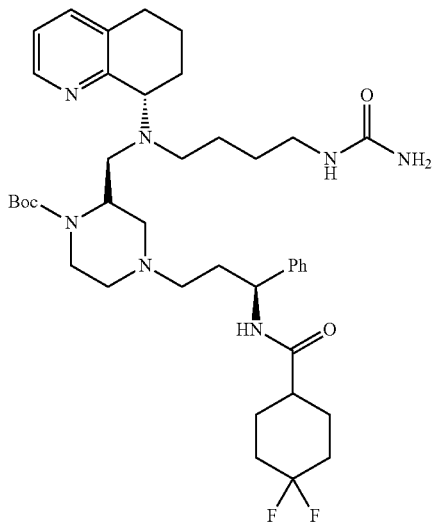

Tert-butyl 2-[[4-aminobutyl-[(8S)-5,6,7,8-tetrahydroquinolin-8-yl]amino]methyl]-4-[(3R)-3-[(4,4-difluorocyclohexanecarbonyl)amino]-3-phenyl-propyl]piperazine-1-carboxylate 69 (0.15 g, 0.2100 mmol) was dissolved in THE (5 mL) at room temperature. Then added N,N-diisopropylethylamine (0.08 mL, 0.4600 mmol) and trimethylsilylisocyanate (0.03 g, 0.2500 mmol) and stirred at room temperature for overnight. The reaction was poured into water and aqueous phase was extracted with DCM. Combined organic layer was dried over anhydrous MgSO$_4$, filtered off and evaporated. Compound 70 was used for the next step without purification.

71

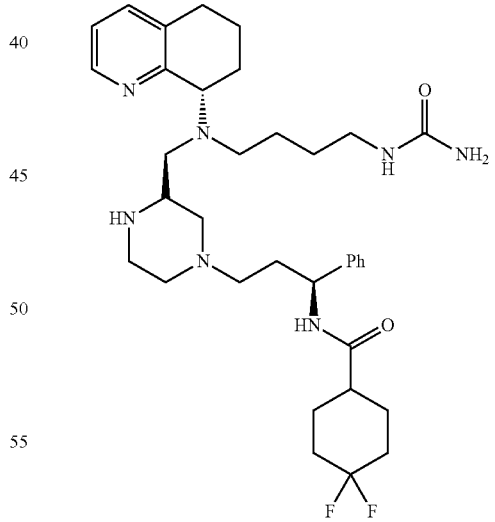

The tert-butyl 4-[(3R)-3-[(4,4-difluorocyclohexanecarbonyl)amino]-3-phenyl-propyl]-2-[[[(8S)-5,6,7,8-tetrahydroquinolin-8-yl]-(4-ureidobutyl)amino]methyl]piperazine-1-carboxylate 70 (0.15 g, 0.2000 mmol) was dissolved in DCM (3 mL) and added trifluoroacetic acid (0.31 mL, 4 mmol) and stirred at room temperature overnight. The reaction was basified with 1N NaOH to pH>10-12 and extracted with DCM three times. combined organic layer was dried over anhydrous MgSO$_4$, filtered off and evaporated. The product 71 was purified with column chromatography starting with DCM and increased the polarity with DCM:MeOH:NH$_3$ (8:2:0.3) to afford 0.100 g (78%) yield $^1$H NMR (600 MHz, Methanol-d4) δ 8.45 (d, J=3.3 Hz, 1H), 7.67 (d, J=8.1 Hz, 1H), 7.39-7.29 (m, 5H), 7.29-7.23 (m, 1H), 5.00 (t, J=7.4 Hz, 1H), 4.16 (dd, J=10.4, 6.0 Hz, 1H), 3.49-3.38 (m, 1H), 3.33 (p, J=1.6 Hz, 2H), 3.30-3.21 (m, 1H), 3.15 (ddt, J=13.2, 6.3, 3.1 Hz, 1H), 3.10-3.05 (m, 1H), 3.04 (s, 1H), 3.01-2.83 (m, 3H), 2.81 (d, J=17.1 Hz, 1H), 2.59 (t, J=7.5 Hz, 2H), 2.54-2.34 (m, 5H), 2.26-2.16 (m, 2H), 2.14-2.05 (m, 4H), 2.01 (q, J=7.2 Hz, 2H), 1.98-1.86 (m, 2H), 1.85-1.65 (m, 7H), 1.40 (dt, J=7.2, 3.9 Hz, 6H).

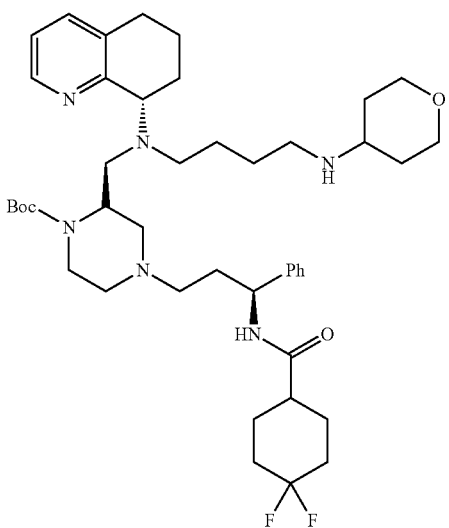

72

The tert-butyl 2-[[4-aminobutyl-[(8S)-5,6,7,8-tetrahydroquinolin-8-yl]amino]methyl]-4-[(3R)-3-[(4,4-difluorocyclohexanecarbonyl)amino]-3-phenyl-propyl]piperazine-1-carboxylate 69 (0.15 g, 0.2200 mmol) was dissolved in DCE (3 mL) and added tetrahydro-4H-pyran-4-one (0.03 mL, 0.2800 mmol) and sodium triacetoxyborohydride (0.07 g, 0.3200 mmol). The reaction mixture was stirred at room temperature for overnight. Then reaction mixture was quenched with Na$_2$CO$_3$ solution and extracted with DCM three times. Combined organic layer was dried over anhydrous MgSO$_4$, filtered off and evaporated. The product 72 was purified with column chromatography starting with DCM and increased the polarity with DCM:MeOH:NH$_3$ (9:1:0.2) (0.15 g 83% yield).

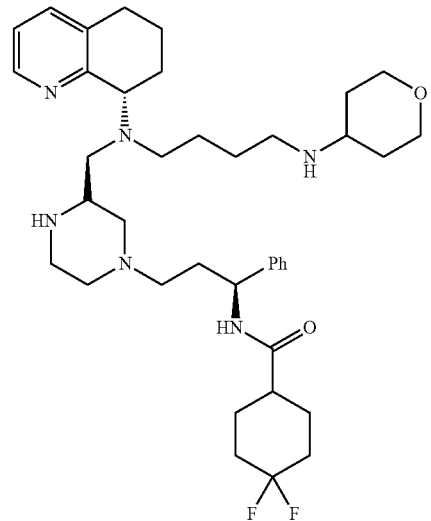

73

The tert-butyl 4-[(3R)-3-[(4,4-difluorocyclohexanecarbonyl)amino]-3-phenyl-propyl]-2-[[4-(tetrahydropyran-4-ylamino)butyl-[(8S)-5,6,7,8-tetrahydroquinolin-8-yl]amino]methyl]piperazine-1-carboxylate 72 (0.15 g, 0.1900 mmol) was dissolved in DCM (5 mL) and trifluoroacetic acid (0.3 mL, 3.84 mmol) was added and stirred at room temperature overnight. The reaction mixture was basified with 1N NaOH to pH>10-12 and extracted with DCM three times. Combined organic layer was dried over anhydrous MgSO$_4$, filtered off and evaporated. The product 73 was purified with column chromatography starting with DCM and increased the polarity with DCM:MeOH:NH$_3$ (8:2:0.6) to afford 0.115 g (88%) yield $^1$H NMR (600 MHz, Methanol-d4) δ 8.45 (d, J=4.7 Hz, 1H), 7.63 (d, J=7.7 Hz, 1H), 7.39-7.31 (m, 4H), 7.31-7.22 (m, 2H), 5.01 (t, J=7.6 Hz, 1H), 4.83 (s, 1H), 4.12 (dd, J=10.6, 6.1 Hz, 1H), 4.07-3.97 (m, 2H), 3.44 (q, J=14.4, 12.0 Hz, 3H), 3.22 (d, J=9.4 Hz, 1H), 3.18-3.10 (m, 2H), 3.08-2.86 (m, 6H), 2.81 (d, J=16.4 Hz, 1H), 2.68-2.58 (m, 2H), 2.57-2.35 (m, 5H), 2.26-2.16 (m, 2H), 2.16-2.04 (m, 3H), 2.04-1.87 (m, 7H), 1.88-1.71 (m, 6H), 1.71-1.49 (m, 7H).

74

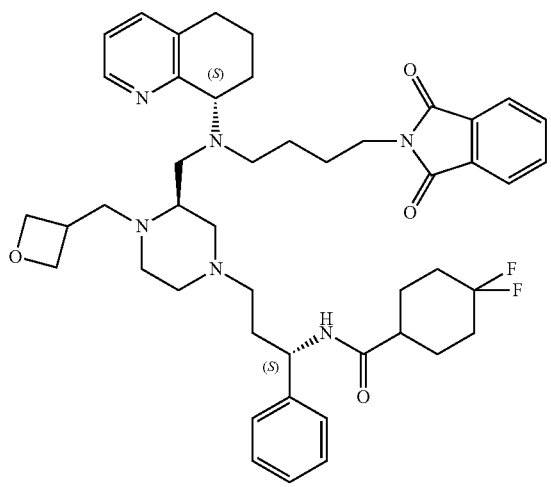

A 20 mL vial equipped with a stir bar was charged with 250 mg of the amine 62 (0.340 mmol, 1 equiv.), 35.6 mg of oxetane-3-carbaldehyde (0.410 mmol, 1.2 equiv.), 0.020 mL of CH₃COOH (0.340 mmol, 1 equiv.) and 3.4 mL of CH₂Cl₂ and the solution was stirred for 30 min. Then 117 mg of NaBH(OAc)₃ (0.550 mmol, 1.6 equiv.) was added. After stirring at rt for 2 days, the reaction was not done. 18.0 mg of oxetane-3-carbaldehyde (0.205 mmol, 0.6 equiv.) and 58.0 mg of NaBH(OAc)₃ (0.275 mmol, 0.8 equiv.) were added and the stirring was continued for 2 h. The reaction mixture was quenched by addition of sat. NaHCO₃solution and sat. Na₂CO₃ sol., and the product was extracted with CH₂Cl₂ (3×) and dried over Na₂SO₄. The crude product was purified on silica gel column (24 g) using 0-30% MeOH in EA as eluent affording 249 mg (91%) of N—((S)-3-((R)-3-(((4-(1,3-dioxoisoindolin-2-yl)butyl)((S)-5,6,7,8-tetrahydroquinolin-8-yl)amino)methyl)-4-(oxetan-3-ylmethyl)piperazin-1-yl)-1-phenylpropyl)-4,4-difluorocyclohexane-1-carboxamide 74 as a white foam.

75

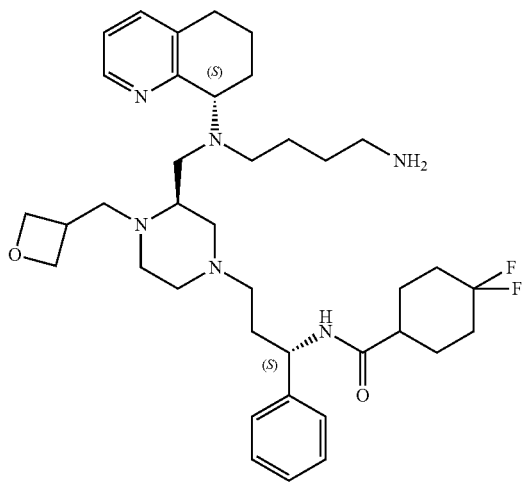

A 20 mL vial equipped with magnetic stir bar was charged with 137 mg of the amine 74 (0.170 mmol, 1 equiv.) and 0.180 mL of the 24% hydrazine solution in water (1.38 mmol, 8 equiv.) dissolved in 2 mL of MeOH. After stirring at rt for 12 h, the reaction mixture was quenched by addition of sat. Na₂CO₃ solution, extracted with CH₂Cl₂ (3×) and dried over Na₂SO₄. The organics were concentrated and the crude product was purified on silica gel column using 0-60% of solvent 2 (solvent 2=30% MeOH in CH₂Cl₂₊₃% NH₄OH) in CH₂Cl₂ affording 92 mg (80%) of N—((S)-3-((R)-3-(((4-aminobutyl)((S)-5,6,7,8-tetrahydroquinolin-8-yl)amino)methyl)-4-(oxetan-3-ylmethyl)piperazin-1-yl)-1-phenylpropyl)-4,4-difluorocyclohexane-1-carboxamide 75 as a white foam. ¹H NMR (400 MHz, CDCl₃, ppm) δ:8.36 (dd, J=4.7, 1.7 Hz, 1H), 8.24 (d, J=6.9 Hz, 1H), 7.29 (dd, J=7.8, 1.7 Hz, 1H), 7.27-7.22 (m, 2H), 7.19-7.14 (m, 3H), 6.98 (dd, J=7.7, 4.6 Hz, 1H), 5.03 (q, J=6.0 Hz, 1H), 4.75 (dd, J=7.8, 6.0 Hz, 1H), 4.71 (dd, J=7.8, 6.0 Hz, 1H), 4.36 (t, J=6.2 Hz, 1H), 4.33 (t, J=6.1 Hz, 1H), 3.98 (dd, J=8.7, 5.6 Hz, 1H), 3.33 (br s, 1H), 3.27 (dd, J=12.7, 7.9 Hz, 1H), 3.13 (sept., J=7.0 Hz, 1H), 2.92 (dd, J=13.2, 3.7 Hz, 1H), 2.79-1.33 (m, 37H). ¹⁹F NMR (376 MHz, CDCl₃, ppm) δ: −93.83 (d, J=236.5 Hz), −101.02 (d, J=236.7 Hz).

76

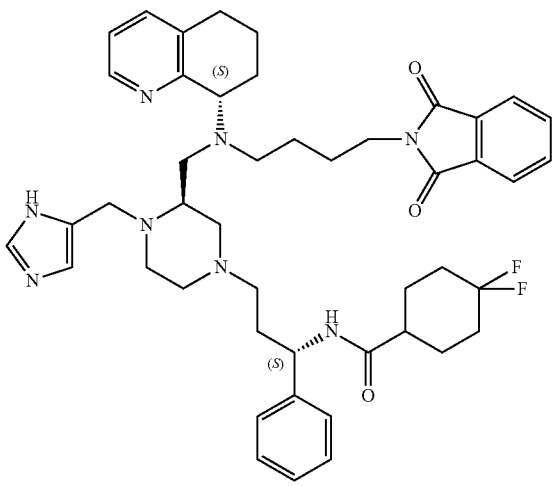

A 20 mL vial equipped with a stir bar was charged with 250 mg of the amine 62 (0.340 mmol, 1 equiv.), 40.0 mg of 1H-imidazole-4-carbaldehyde (0.410 mmol, 1.2 equiv.), 0.020 mL of acetic acid (0.340 mmol, 1 equiv.) and 3.4 mL of CH₂Cl₂ and the solution was stirred for 1 h. Then 117 mg of NaBH(OAc)₃ (0.550 mmol, 1.6 equiv.) was added. After stirring at rt for 2 days, the reaction was not complete. 20.0 mg of 1H-imidazole-4-carbaldehyde (0.205 mmol, 0.6 equiv.) and 58.0 mg of NaBH(OAc)₃ (0.275 mmol, 0.8 equiv.) were added and the stirring was continued for 12 h. The reaction mixture was quenched by addition of sat. NaHCO₃solution and sat. Na₂CO₃ sol., and the product was extracted with CH₂Cl₂ (3×) and dried over Na₂SO₄. The crude product was purified on silica gel column (24 g) using 0-30% MeOH in EA as eluent affording 177 mg (42%) of N—((S)-3-((R)-4-((1H-imidazol-5-yl)methyl)-3-(((4-(1,3-dioxoisoindolin-2-yl)butyl)((S)-5,6,7,8-tetrahydroquinolin-8-yl)amino)methyl)piperazin-1-yl)-1-phenylpropyl)-4,4-difluorocyclohexane-1-carboxamide 76 as a white foam.

77

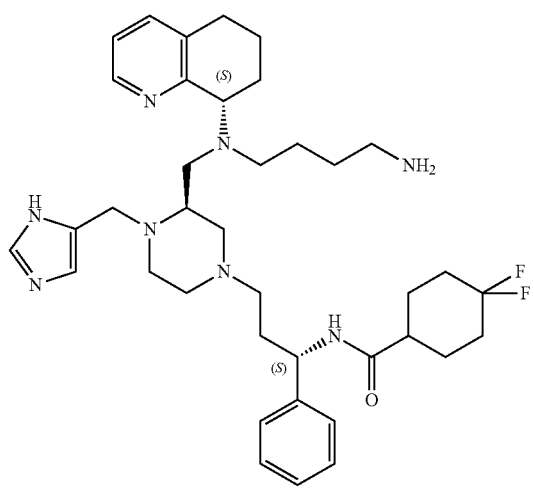

A 20 mL vial equipped with magnetic stir bar was charged with 117 mg of the amine 76 (0.140 mmol, 1 equiv.) and 0.152 mL of the 24% hydrazine solution in water (1.16 mmol, 8 equiv.) dissolved in 2 mL of MeOH. After stirring at rt for 12 h, the reaction mixture was quenched by addition of sat. Na$_2$CO$_3$ solution, extracted with CH$_2$Cl$_2$ (3×) and dried over Na$_2$SO$_4$. The organics were concentrated and the crude product was purified on silica gel column using 0-60% of solvent 2 (solvent 2=30% MeOH in CH$_2$Cl$_{2+3}$% NH$_4$OH) in CH$_2$Cl$_2$ affording 57 mg (58%) of N—((S)-3-((R)-4-((1H-imidazol-5-yl)methyl)-3-(((4-aminobutyl)((S)-5,6,7,8-tetrahydroquinolin-8-yl)amino)methyl)piperazin-1-yl)-1-phenylpropyl)-4,4-difluorocyclohexane-1-carboxamide 77 as a white foam. $^1$H NMR (400 MHz, CDCl$_3$, ppm) δ: 8.39 (dd, J=4.7, 1.6 Hz, 1H), 8.02 (s, 1H), 7.63 (s, 1H), 7.39 (dd, J=7.7, 1.6 Hz, 1H), 7.30-7.24 (m, 2H), 7.22-7.14 (m, 3H), 7.09 (dd, J=7.7, 4.7 Hz, 1H), 6.91 (s, 1H), 4.99 (q, J=6.1 Hz, 1H), 4.17 (dd, J=10.4, 5.7 Hz, 1H), 4.00 (A of AB, J$_{AB}$=14.9 Hz, 1H), 3.87 (B of AB, J$_{AB}$=14.8 Hz, 1H), 3.05 (dd, J=14.7, 5.0 Hz, 1H), 2.93-2.57 (m, 8H), 2.50 (t, J=6.8 Hz, 2H), 2.54-1.49 (m, 21H), 1.37-1.13 (m, 6H). The imidazole N—H can not be seen. $^1$H NMR (600 MHz, CDCl$_3$, ppm) δ:13.82 (br s, 1H), 8.40 (dd, J=4.8, 1.6 Hz, 1H), 7.97 (s, 1H), 7.64 (s, 1H), 7.40 (dd, J=7.7, 1.6 Hz, 1H), 7.31-7.25 (m, 2H), 7.22-7.15 (m, 3H), 7.10 (dd, J=7.7, 4.7 Hz, 1H), 6.92 (s, 1H), 5.00 (q, J=6.2 Hz, 1H), 4.18 (dd, J=10.8, 5.8 Hz, 1H), 4.02 (d, J=15.1 Hz, 1H), 3.87 (d, J=14.9 Hz, 1H), 3.05 (d, J=14.0 Hz, 1H), 2.87-2.60 (m, 8H), 2.51 (d, J=7.1 Hz, 2H), 2.44-1.99 (m, 13H), 1.89-1.53 (m, 8H), 1.36-1.17 (m, 6H). $^{19}$F NMR (376 MHz, CDCl$_3$, ppm) δ: −94.21 (d, J=236.4 Hz), −101.19 (d, J=236.1 Hz).

78

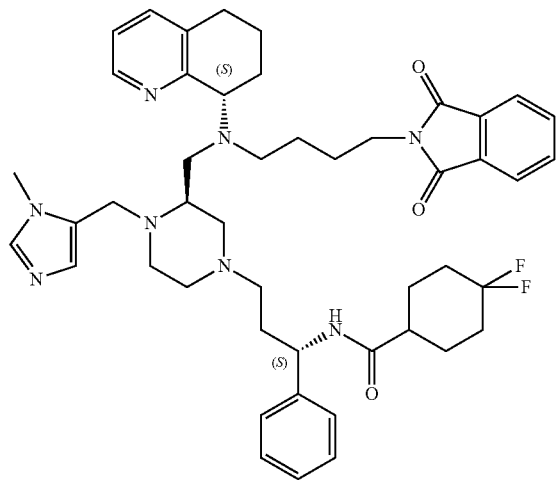

A 20 mL vial equipped with a stir bar was charged with 238 mg of the amine 62 (0.330 mmol, 1 equiv.), 43.3 mg of 1-methyl-1H-imidazole-4-carbaldehyde (0.390 mmol, 1.2 equiv.), 0.019 mL of CH$_3$COOH (0.330 mmol, 1 equiv.) and 3.4 mL of CH$_2$Cl$_2$. Then 111 mg of NaBH(OAc)$_3$ (0.520 mmol, 1.6 equiv.) was added. After stirring at rt for 12 h, more 43.3 mg of 1-methyl-1H-imidazole-4-carbaldehyde (0.390 mmol, 1.2 equiv.) and 56.0 mg of NaBH(OAc)$_3$ (0.260 mmol, 0.8 equiv.) were added and the reaction mixture was stirred for 12 h. Then the reaction mixture was quenched by addition of sat. NaHCO$_3$ solution and sat. Na$_2$CO$_3$ sol., and the product was extracted with CH$_2$Cl$_2$ (3×) and dried over Na$_2$SO$_4$. The reaction did not go to completion and was resubmitted to reaction conditions. A 20 mL vial equipped with a stir bar was charged with the recovered amine 62 and product mixture (0.330 mmol, 1 equiv.), 43.3 mg of 1-methyl-H-imidazole-4-carbaldehyde (0.390 mmol, 1.2 equiv.), 0.019 mL of CH$_3$COOH (0.330 mmol, 1 equiv.) and 3.4 mL of CH$_2$Cl$_2$ and stirred at rt for 3 h. Then 111 mg of NaBH(OAc)$_3$ (0.520 mmol, 1.6 equiv.) was added. After stirring at rt for 12 h, the reaction mixture was quenched by addition of sat. NaHCO$_3$ solution and sat. Na$_2$CO$_3$ sol., and the product was extracted with CH$_2$Cl$_2$ (3×) and dried over Na$_2$SO$_4$. The crude product was purified on silica gel column (12 g) using 0-30% MeOH in EA as eluent affording 116 mg (43%) of N—((S)-3-((R)-3-(((4-(1,3-dioxoisoindolin-2-yl)butyl)((S)-5,6,7,8-tetrahydroquinolin-8-yl)amino)methyl)-4-((1-methyl-1H-imidazol-5-yl)methyl)piperazin-1-yl)-1-phenylpropyl)-4,4-difluorocyclohexane-1-carboxamide 78 as a yellowish foam.

79

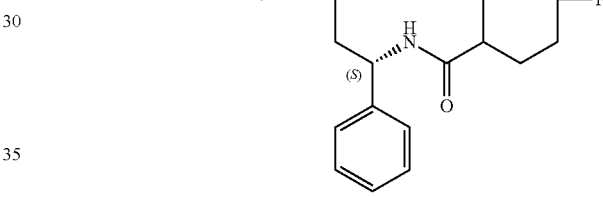

A 20 mL vial equipped with magnetic stir bar was charged with 106 mg of the amine 78 (0.130 mmol, 1 equiv.) and 0.135 mL of the 24% hydrazine solution in water (1.03 mmol, 8 equiv.) dissolved in 1.3 mL of MeOH. After stirring at rt for 12 h, the reaction mixture was quenched by addition of sat. Na$_2$CO$_3$ solution, extracted with CH$_2$Cl$_2$ (3×) and dried over Na$_2$SO$_4$.

The organics were concentrated and the crude product was purified on silica gel column using 0-60% of solvent 2 (solvent 2=30% MeOH in CH$_2$Cl$_{2+3}$% NH$_4$OH) in CH$_2$Cl$_2$ affording 73 mg (82%) of N—((S)-3-((R)-3-(((4-aminobutyl)((S)-5,6,7,8-tetrahydroquinolin-8-yl)amino)methyl)-4-((1-methyl-1H-imidazol-5-yl)methyl)piperazin-1-yl)-1-phenylpropyl)-4,4-difluorocyclohexane-1-carboxamide 79 as a white foam. $^1$H NMR (400 MHz, CDCl$_3$, ppm) δ: 8.37 (d, J=4.6 Hz, 1H), 8.26 (d, J=6.8 Hz, 1H), 7.35 (s, 1H), 7.31 (d, J=7.7 Hz, 1H), 7.31-7.21 (m, 2H), 7.23-7.13 (m, 3H), 7.00 (dd, J=7.7, 4.6 Hz, 1H), 6.84 (s, 1H), 5.04 (q, J=6.0 Hz, 1H), 4.12 (d, J=13.9 Hz, 1H), 4.01 (dd, J=9.1, 5.7 Hz, 1H), 3.58 (s, 3H), 3.14 (d, J=13.1 Hz, 1H), 3.08 (dd, J=13.4, 3.9 Hz, 1H), 2.87-2.62 (m, 4H), 2.59 (t, J=6.4 Hz, 2H), 2.54-1.31 (m, 31H). $^{19}$F NMR (376 MHz, CDCl$_3$, ppm) δ: −93.89 (d, J=236.3 Hz), −100.94 (d, J=235.9 Hz).

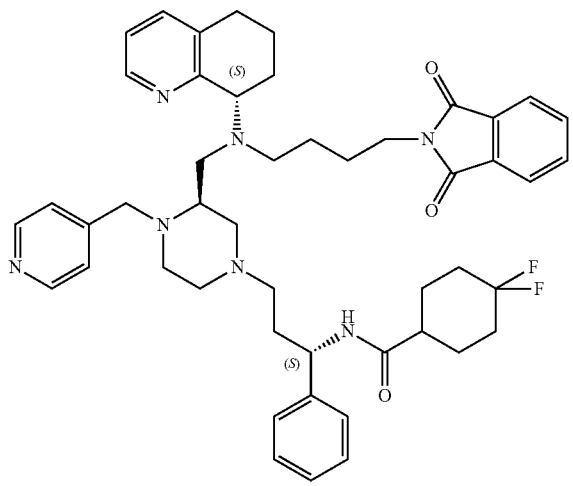

80

A 20 mL vial equipped with a stir bar was charged with 250 mg of the amine 62 (0.340 mmol, 1 equiv.), 55.3 mg of isonicotinaldehyde (0.520 mmol, 1.5 equiv.) and 3.4 mL of DCE and the solution was stirred for 1 h. Then 117 mg of NaBH(OAc)$_3$ (0.550 mmol, 1.6 equiv.) was added. After stirring at rt for 12 h, the reaction was not done. 55.3 mg of isonicotinaldehyde (0.520 mmol, 1.5 equiv.) and the stirring was continued for 2 h. The reaction mixture was quenched by addition of sat. NaHCO$_3$ and sat. Na$_2$CO$_3$ sol., and the product was extracted with CH$_2$Cl$_2$ (3×) and dried over Na$_2$SO$_4$. The crude product was purified on silica gel column (12 g) using 0-30% MeOH in EA as eluent affording 220 mg (78%) of N—((S)-3-((R)-3-(((4-(1,3-dioxoisoindo-lin-2-yl)butyl)((S)-5,6,7,8-tetrahydroquinolin-8-yl)amino) methyl)-4-(pyridin-4-ylmethyl)piperazin-1-yl)-1-phenyl-propyl)-4,4-difluorocyclohexane-1-carboxamide 80 as a slightly yellowish foam.

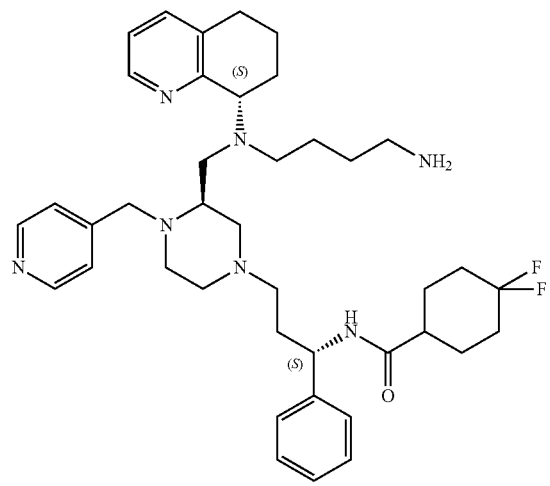

81

A 20 mL vial equipped with magnetic stir bar was charged with 127 mg of the amine 80 (0.160 mmol, 1 equiv.) and 0.203 mL of the 24% hydrazine solution in water (1.55 mmol, 10 equiv.) dissolved in 1.5 mL of MeOH. After stirring at rt for 2 days, the reaction mixture was quenched by addition of sat. Na$_2$CO$_3$ solution, extracted with CH$_2$Cl$_2$ (3×) and dried over Na$_2$SO$_4$. The organics were concentrated and the crude product was purified on silica gel column using 0-60% of solvent 2 (solvent 2=30% MeOH in CH$_2$Cl$_{2+3}$% NH$_4$OH) in CH$_2$Cl$_2$ affording 97 mg (91%) of N—((S)-3-((R)-3-(((4-aminobutyl)((S)-5,6,7,8-tetrahydro-quinolin-8-yl)amino)methyl)-4-(pyridin-4-ylmethyl)piper-azin-1-yl)-1-phenylpropyl)-4,4-difluorocyclohexane-1-car-boxamide 81 as a white foam. $^1$H NMR (400 MHz, CDCl$_3$, ppm) δ: 8.47-8.43 (m, 2H), 8.35 (dd, J=4.8, 1.6 Hz, 1H), 8.29 (d, J=7.0 Hz, 1H), 7.28 (dd, J=7.8, 1.7 Hz, 1H), 7.26-7.13 (m, 7H), 6.98 (dd, J=7.7, 4.7 Hz, 1H), 5.02 (q, J=6.2 Hz, 1H), 4.36 (d, J=14.9 Hz, 1H), 4.00 (dd, J=9.1, 5.8 Hz, 1H), 3.22 (br s, 1H), 3.10 (d, J=14.9 Hz, 1H), 2.85 (dd, J=13.4, 4.1 Hz, 1H), 2.78-1.30 (m, 36H). $^{19}$F NMR (376 MHz, CDCl$_3$, ppm) δ: −93.84 (d, J=236.4 Hz), −100.92 (d, J=236.9 Hz).

Synthesis of Bridged Analogs

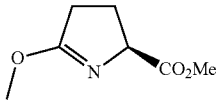

82

A 250 mL rb flask equipped with a stir bar and rubber septum was charged with 40.0 g of methyl (S)-5-oxopyrro-lidine-2-carboxylate (279 mmol, 1 equiv.) and 26.7 mL of dimethylsulfate (279 mmol, 1 equiv.) and the solution was heated at 56° C. for 18 h. Then the solution was cooled and poured into 58.4 mL of NEt$_3$ (419 mmol, 1.5 equiv.) dis-solved in 10 mL of diethyl ether and the emulsion was stirred for 30 min. Then water (100 mL) was added and the product was extracted with diethyl ether (3×), washed with sat. NaHCO$_3$ solution and dried over Na$_2$SO$_4$. The organics were concentrated and toluene was added. The organics were concentrated again (distills off NEt$_3$) affording 28.15 g (84 w % in toluene, 23.6 g, 54%) of methyl (S)-5-methoxy-3,4-dihydro-2H-pyrrole-2-carboxylate 82 as a brownish oil.

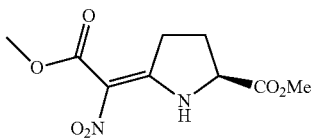

83

A 500 mL rb flask equipped with a rubber septum and a magnetic stir bar was charged with 36.0 g of methyl (S)-5-methoxy-3,4-dihydro-2H-pyrrole-2-carboxylate 82 (229 mmol, 1 equiv.) and 23.0 mL of methyl nitroacetate (250 mmol, 1.09 equiv.) and the reaction mixture was stirred at rt for 24 h. The product was not observed by TLC and the reaction mixture was heated at 60° C. for 40 h. Then solution was cooled and dissolved in CH$_2$Cl$_2$ and hexanes. The seed crystal was added and the formed crystals were filtered and washed with diethyl ether affording 4.95 g of the product as a yellowish solid. The filtrate was washed with water and the product was back extracted with CH$_2$Cl$_2$ (2×). The organics were concentrated and the product was crystallized from CH$_2$Cl$_2$ and diethyl ether using seed crystals to initiate the crystallization affording 4.35 g of the product 83 as a yellow solid. The residue was concentrated and purified on silica gel column (330 g) using 0 to 50% EA in CH$_2$Cl$_2$ as eluent affording a yellow oil which was recrystallized from CH₂Cl₂/diethyl ether affording 12.2 g of methyl (S)-5-(2-methoxy-1-nitro-2-oxoethylidene)pyrrolidine-2-carboxylate 83 as a yellowish solid (total 21.5 g, 38%). 1:1 mixture of E/Z isomers:

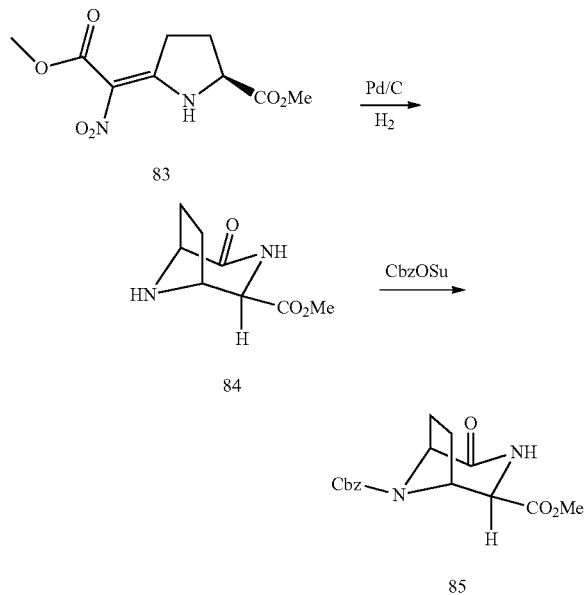

A 500 mL Parr hydrogenator bottle was charged with 12.2 g of the alkene 83 (50.0 mmol, 1 equiv.) and 1.75 g of 20 w % Pd(OH)₂ on carbon (2.50 mmol, 0.05 equiv.) dissolved in 30 mL of dry methanol. The mixture was shaken at 45 psi hydrogen atmosphere for 3 days. The suspension was filtered through celite plug and the plug was washed with ethanol. The solution was concentrated and the reaction was resubmitted to the same reaction conditions and same workup. The crude product 84 was used in the next step without further purification.

A 250 mL rb flask equipped with a stir bar was charge with 9.20 g of methyl (1R,2R,5S)-4-oxo-3,8-diazabicyclo[3.2.1]octane-2-carboxylate 84 (50.0 mmol, 1 equiv.), 11.8 mL of NEt₃ (84.9 mmol, 1.7 equiv.), few crystals of DMAP and 100 mL of CH₂Cl₂. Then 16.2 g of CbzOSu (64.9 mmol, 1.3 equiv.) was added. After stirring at rt for 48 h, the reaction mixture was quenched by addition of sat. NH₄Cl solution, extracted with CH₂Cl₂ (3×) and dried over Na₂SO₄. The crude product was purified on silica gel column (120 g) using 0-100% EA in hexanes as eluent affording 5.67 g of the product as a yellow oil (still some impurity).

The product 85 was repurified on silica gel column (220 g) using 0 to 100% EA in hexanes as eluent affording of 8-benzyl 2-methyl (1R,2R,5S)-4-oxo-3,8-diazabicyclo[3.2.1]octane-2,8-dicarboxylate 85 as a slightly yellow oil. The product was dissolved in toluene and seed crystals were added. The crystallized product was filtered and washed with ether affording 4.15 g of the product as yellowish solid. The filtrate was concentrated and purified again on silica gel column (80 g) using 0 to 100% EA in CH₂Cl₂ as eluent. The product was crystallized from diethyl ether affording 0.537 g of the product as yellowish solid (total 4.69 g, 29%).

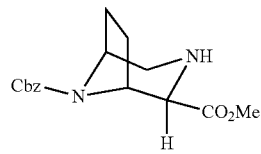

A 500 mL rb flask equipped with a rubber septum and magnetic stir bar was charged with 8.29 g of (C₅H₅)₂ZrHCl (Schwartz reagent) (32.3 mmol, 1.2 equiv.) and 200 mL of THF. Then 8.56 g of the amide 85 (26.9 mmol, 1 equiv.) dissolved in 100 mL of THF was added dropwise via syringe. After stirring the suspension at rt for 30 min, more 2.0 g of the Schwartz reagent (8.07 mmol, 0.3 equiv.). After 10 min stirring, almost clear solution was obtained. The solution was cooled in ice bath and 9.12 g of NaBH(OAc)₃ (43.0 mmol, 1.6 equv) was added in one portion. After stirring at rt for 2 h, the reaction did not go to completion and more 5.70 g of the NaBH(OAc)₃ was added (26.9 mmol, 1 equiv.) and the stirring was continued for 12 h. The reaction mixture was quenched by addition of sat. NaHCO₃ solution, extracted with CH₂Cl₂ (1×), then sat. Na₂CO₃ solution was added to the aqueous phase, extracted with CH₂Cl₂ (2×) and the combined organics were dried over Na₂SO₄. The organics were concentrated and the crude product was dissolved in CH₂Cl₂ and filtered through celite plug. The obtained product (8-benzyl 2-methyl (1R,2R,5S)-3,8-diazabicyclo[3.2.1]octane-2,8-dicarboxylate 86) (yellow oil) was used in the next step without further purification.

A Sample for Characterization was Obtained from Other Experiment:

A 100 mL rb flask equipped with a rubber septum and magnetic stir bar was charged with 650 mg of the Schwartz reagent (2.53 mmol, 1.5 equiv.) and 8 mL of THF. Then 537 mg of the amide (1.69 mmol, 1 equiv.) dissolved in 8 mL of THF was added dropwise via syringe. After stirring the suspension at rt for 30 min, a clear solution was obtained. The solution was cooled in ice bath and 715 mg of NaBH(OAc)₃ (3.37 mmol, 2 equv) was added in one portion. After stirring at rt for 12 h, the reaction did not go to completion and more 715 mg of the NaBH(OAc)₃ was added (3.37, 2 equiv.) and the stirring was continued for 12 h. The reaction mixture was quenched by addition of sat. NaHCO₃ and sat. Na₂CO₃ solutions, extracted with CH₂Cl₂ (3×) and dried over Na₂SO₄. The crude product was purified on silica gel column (12 g) using 0 to 100% EA in hexanes as eluent affording 404 mg (77%) (still some impurity) of product 86 as a yellow oil.

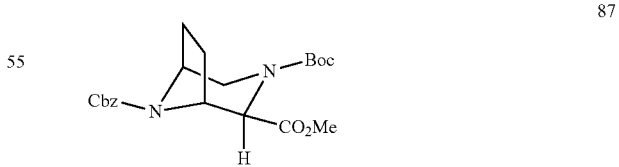

A 250 mL rb flask equipped with a rubber septum and magnetic stir bar was charged with 8.18 g of the amine 86 (26.9 mmol, 1 equiv.), 4.9 mL of NEt₃ (34.9 mmol, 1.3 equiv., 70 mg of DMAP (0.540 mmol, 0.02 equiv.) and 100 mL of CH₂Cl₂. After cooling the reaction mixture in the ice bath, 7.04 g of Boc₂O (32.3 mmol, 1.2 equiv.) was added in one portion. After stirring the solution at rt for 48 h, more 3.52 g of Boc₂O (16.2 mmol, 0.6 equiv.) was added. Then the reaction mixture was quenched by addition of water, extracted with CH₂Cl₂ (3×) and dried over Na₂SO₄. The organics were concentrated and the crude product was purified on silica gel column (120 g) using 0 to 20% EA in CH₂Cl₂ as eluent. The obtained product contained some minor impurities, which were separated on silica gel column (80 g) using 0 to 30% EA in hexanes as eluent affording 4.87 g (45%) of 8-benzyl 3-(tert-butyl) 2-methyl (1R,2R,5S)-3, 8-diazabicyclo[3.2.1]octane-2,3,8-tricarboxylate 87 as an orange brownish oil.

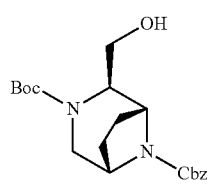

88

A 250 mL rb flask equipped with rubber septum and magnetic stir bar was charged with 3.57 g of the ester 87 (8.83 mmol, 1 equiv.) and 89 mL of ether. The flask was cooled in an ice bath and 13.2 mL of 2M LiBH₄ solution in THF (26.5 mmol, 3 equiv.) was added. After stirring at rt for 20 h, the reaction mixture was quenched by addition of water and 2N HCl solution till the bubbling is done (pH=6), extracted with ethyl ether (3×) and dried over Na₂SO₄. The crude product was purified on silica gel column (40 g) using 0 to 50% EA in hexanes as eluent affording 0.996 g (30%) of 8-benzyl 3-(tert-butyl) (1R,2R,5S)-2-(hydroxymethyl)-3, 8-diazabicyclo[3.2.1]octane-3,8-dicarboxylate 88 as a clear oil, 0.123 g of the mixture of the product and the by-product and 1.563 g (59%) of more polar by-product (benzyl (6S, 9R,9aR)-3-oxohexahydro-1H,3H-6,9-epiminooxazolo[3,4-a]azepine-10-carboxylate).

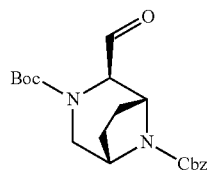

89

A 20 mL vial equipped with a magnetic stir bar and septum was charged with 980 mg of the alcohol 88 (2.60 mmol, 1 equiv.) 25 mL of CH₂Cl₂. Then 1.66 g of Dess-Martin periodinane (3.90 mmol, 1.5 equiv.) was added and the reaction mixture was stirred at rt for 1.5 h. Then the reaction mixture was quenched by addition of sat. NaHCO₃and sat. Na₂S₂O₃ solutions, extracted with diethyl ether (3×), washed with sat. NaHCO₃and sat. Na₂S₂O₃ solutions and dried over Na₂SO₄. After the organics were concentrated and 8-benzyl 3-(tert-butyl) (1R,2R,5S)-2-formyl-3,8-diazabicyclo[3.2.1]octane-3,8-dicarboxylate 89 was used in the next step without further purification.

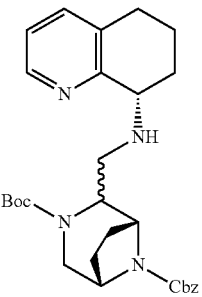

90

A 250 mL rb flask equipped with a stir bar was charged with 626 mg of (S)-5,6,7,8-tetrahydroquinolin-8-amine (3.38 mmol, 1.3 equiv.), 974 mg of the aldehyde 89 (2.60 mmol, 1 equiv.) and 25 mL of DCE. Then 937 mg of NaBH(OAc)₃ (4.42 mmol, 1.7 equiv.) was added and the suspension was stirred at rt for 1 h. Then 300 mg more of NaBH(OAc)₃ (1.41 mmol, 0.54 equiv.) was added. After stirring at rt for 12 h, the reaction mixture was quenched by addition of sat NaHCO₃and sat. Na₂CO₃ solutions and the product was extracted with CH₂Cl₂ (3×) and dried over Na₂SO₄. The crude product was purified on silica gel column (24 g) using 0 to 15% MeOH in CH₂Cl₂ affording 1.02 g (77%) of 8-benzyl 3-(tert-butyl) (1R,5S)-2-((((S)-5, 6,7,8-tetrahydroquinolin-8-yl)amino)methyl)-3,8-diazabicyclo[3.2.1]octane-3,8-dicarboxylate 90 as a yellowish oil.

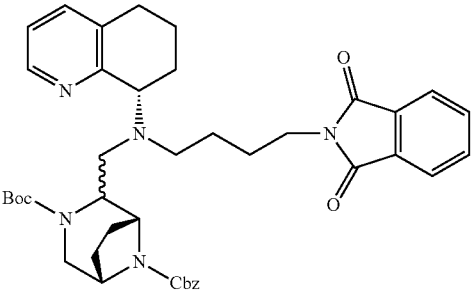

91

A 100 mL rb flask equipped with a stir bar was charge with 1.01 g of the amine 90 (1.98 mmol, 1 equiv.), 0.600 g of 4-(1,3-dioxoisoindolin-2-yl)butanal (2.78 mmol, 1.4 equiv.) and 15 mL of DCE. Then 0.710 g of NaBH(OAc)₃ (3.37 mmol, 1.7 equiv.) was added. After stirring at rt for 12 h, the reaction mixture was quenched by addition of sat. Na₂CO₃ solution and the product was extracted with CH₂Cl₂ (3×) and dried over Na₂SO₄. The crude product was purified on silica gel column (24 g) using 0-100% EA in hexanes as eluent affording 1.35 g (96%) of 8-benzyl 3-(tert-butyl) (1R,5S)-2-(((4-(1,3-dioxoisoindolin-2-yl)butyl)((S)-5,6,7,8-tetrahydroquinolin-8-yl)amino)methyl)-3,8-diazabicyclo [3.2.1]octane-3,8-dicarboxylate 91 as a mixture of the diastereomers as a clear oil. (two diastereomers).

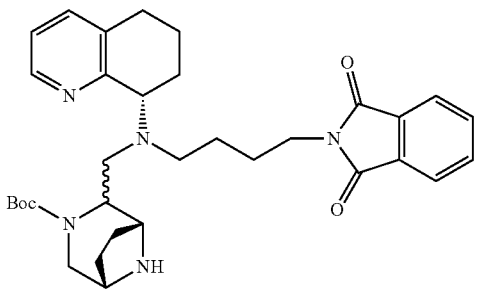

92

A 100 mL rb flask equipped with a stir bar and rubber septum was charged with 1.27 g of the carbamate 91 (1.79 mmol, 1 equiv.), 250 mg of 20 w % of Pd(OH)$_2$ on carbon (0.360 mmol, 0.2 equiv.) and 18 mL of dry methanol. Then 450 mg of NH$_4$OOCH (7.18 mmol, 4 equiv.) was added in one portion. After stirring at rt for 5 h, more 450 mg of NH$_4$OOCH (7.18 mmol, 4 equiv.) was added and the reaction mixture was stirred for 12 h. Then 450 mg more of NH$_4$OOCH (7.18 mmol, 4 equiv.) and 250 mg of 20 w % of Pd(OH)$_2$ on carbon (0.360 mmol, 0.2 equiv.) were added. After stirring at rt for 36 h, the reaction mixture was filtered through a celite plug and the celite plug was washed with ethanol. The organics were concentrated and the reaction was resubmitted at reaction conditions, rt, 12 h. The organics were concentrated in vacuo (rotatory evaporator) and the crude product was dissolved in CH$_2$Cl$_2$ and sat. Na$_2$CO$_3$ solution was added, the product was extracted with CH$_2$Cl$_2$ (3×) and dried over Na$_2$SO$_4$. The crude product was purified on silica gel column (12 g) using EA, then 30% MeOH in CH$_2$Cl$_2$ with 3% of NH$_4$OH as eluent affording 712 mg (69%) of tert-butyl (1R,5S)-2-(((4-(1,3-dioxoisoindolin-2-yl)butyl)((S)-5,6,7,8-tetrahydroquinolin-8-yl)amino) methyl)-3,8-diazabicyclo[3.2.1]octane-3-carboxylate 92 as a LRf isomer 93

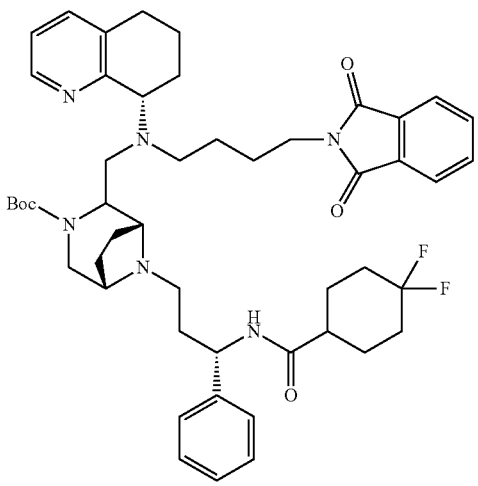

URf isomer 93

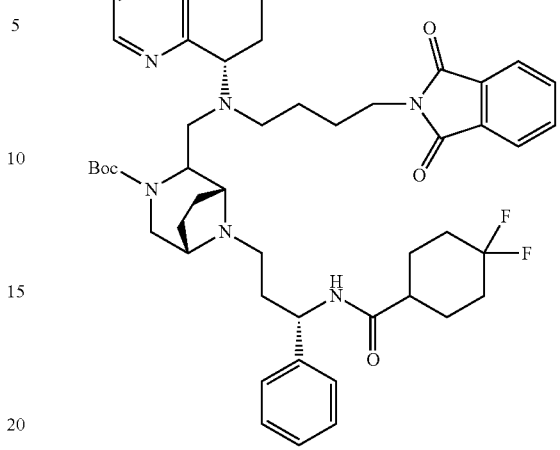

A 20 mL vial equipped with a stir bar was charged with 0.472 g of (S)-4,4-difluoro-N-(3-oxo-1-phenylpropyl)cyclohexane-1-carboxamide (1.60 mmol, 1.3 equiv.), 0.706 g of the amine 92 (1.23 mmol, 1 equiv.), 70 µL of acetic acid (1.23 mmol, 1 equiv.) and 12.3 mL of CH$_2$Cl$_2$. Then 0.443 g of NaBH(OAc)$_3$ (2.09 mmol, 1.7 equiv.) was added and the suspension was stirred at rt for 12 h. The reaction mixture was quenched by addition of sat. NaHCO$_3$ solution, extracted with CH$_2$Cl$_2$ (3×) and dried over Na$_2$SO$_4$. The crude product was purified on silica gel column (80 g) using EA as eluent affording 640 mg (61%) of the 1st isomer (LRf isomer 93, with some impurities) as a white foam (re-purifying on 12 g column using 0 to 100% EA in hexanes as eluent afforded 492 mg of the product as a white foam, still some minor impurities), 80 mg (80%) of the mixture of the isomers and 270 mg (260%) of the 2nd isomer (URf isomer 93) as a white foam. On TLC using 15% MeOH in EA, the 3rd isomer moves little bit faster than 1st isomer.

URf isomer 94

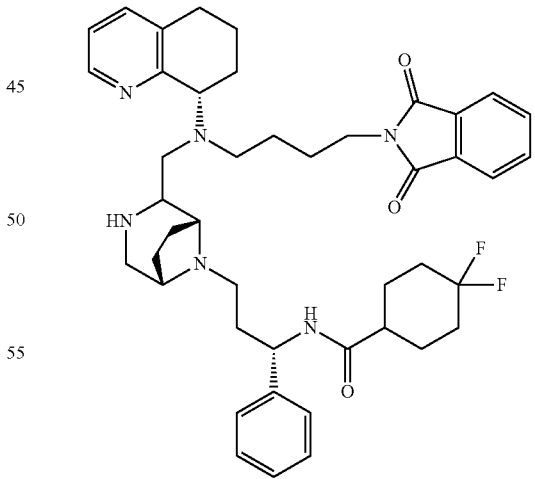

A 20 mL vial equipped with a stir bar was charged with 265 mg of URf isomer 93 (0.310 mmol, 1 equiv.) dissolved in 3.0 mL of dioxane. Then 0.283 mL of 12 M HCl (9.32 mmol, 30 equiv.) was added. After stirring at rt for 12h, the reaction mixture was quenched by addition of sat. Na$_2$CO$_3$ solution, extracted with CH$_2$Cl$_2$ (3×) and dried over Na$_2$SO$_4$. The crude material was purified on silica gel column (12 g) using 0 to 2500 solvent 2 (solvent 2=7000 $CH_2Cl_2$, 3000 MeOH, 30% $NH_4OH$) in $CH_2Cl_2$ as eluent affording 178 mg (76% o) of N-((1S)-3-((1R,5S)-2-(((4-(1,3-dioxoisoindolin-2-yl)butyl)((S)-5,6,7,8-tetrahydroquinolin-8-yl)amino)methyl)-3,8-diazabicyclo[3.2.1]octan-8-yl)-1-phenylpropyl)-4,4-difluorocyclohexane-1-carboxamide (URf isomer 94) as a white foam.

LRf isomer 94

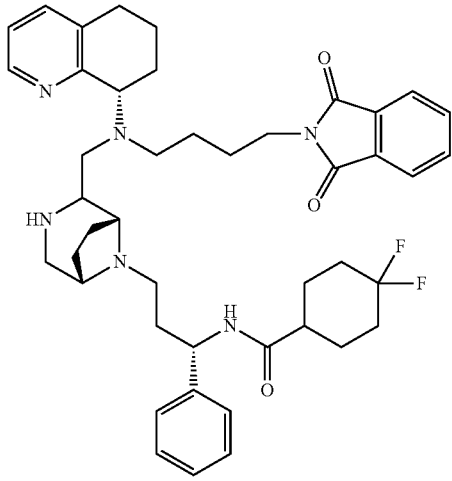

A 20 mL vial equipped with a stir bar was charged with 430 mg of LRf isomer 93 (0.500 mmol, 1 equiv.) dissolved in 5 mL of dioxane. Then 0.459 mL of 12 M HCl (15.1 mmol, 30 equiv.) was added. After stirring at rt for 12 h, the reaction mixture was quenched by addition of sat. $Na_2CO_3$ solution, extracted with $CH_2Cl_2$ (3×) and dried over $Na_2SO_4$. The crude material was purified on silica gel column (12 g) using 0 to 30% solvent 2 (solvent 2=70% $CH_2Cl_2$, 30% MeOH, 3% $NH_4OH$) in $CH_2Cl_2$ as eluent affording 171 mg (some impurities) and 182 mg (minor impurities) of the product. A second purification was performed with combined fractions on silica gel column (24 g) using 0 to 30% solvent 2 (solvent 2=70% $CH_2Cl_2$, 30% MeOH, 3% $NH_4OH$) in $CH_2Cl_2$ as eluent affording 236 mg (62% yield, contains 1% of unknown isomer) of N-((1S)-3-((1R,5S)-2-(((4-(1,3-dioxoisoindolin-2-yl)butyl)((S)-5,6,7,8-tetrahydroquinolin-8-yl)amino)methyl)-3,8-diazabicyclo[3.2.1]octan-8-yl)-1-phenylpropyl)-4,4-difluorocyclohexane-1-carboxamide (LRf isomer 94) as a white foam.

URf isomer 95

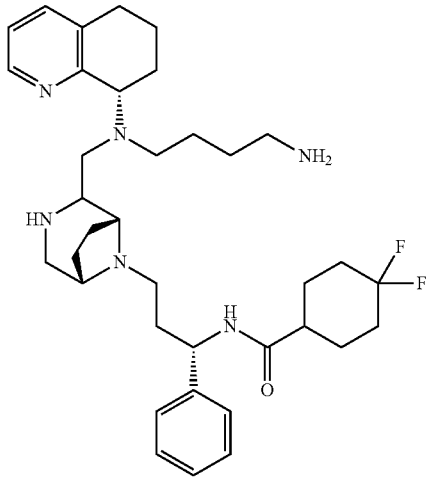

A 20 mL vial equipped with magnetic stir bar was charged with 90.0 mg of URf isomer 94 (0.120 mmol, 1 equiv.) and 0.651 mL of the 24% hydrazine solution in water (1.20 mmol, 10 equiv.) dissolved in 1.2 mL of methanol. After stirring at rt for 12 h, the reaction mixture was quenched by addition of 2M KOH sol., extracted with $CH_2Cl_2$ (3×) and dried over $Na_2SO_4$. The organics were concentrated and the crude product was purified on silica gel column (12 g) using 0-60% of solvent 2 (solvent 2=30% MeOH in $CH_2Cl_2$+3% $NH_4OH$) in $CH_2Cl_2$ affording 63 mg (85%) of N-((1S)-3-((1R,5S)-2-(((4-aminobutyl)((S)-5,6,7,8-tetrahydroquinolin-8-yl)amino)methyl)-3,8-diazabicyclo[3.2.1]octan-8-yl)-1-phenylpropyl)-4,4-difluorocyclohexane-1-carboxamide (URf isomer 95) as a white foam. For URf isomer 95: $^1H$ NMR (400 MHz, $CDCl_3$, ppm) δ: 8.85 (d, J=6.8 Hz, 1H), 8.42 (dd, J=4.7, 1.8 Hz, 1H), 7.34-7.14 (m, 6H), 7.01 (dd, J=7.7, 4.7 Hz, 1H), 5.02 (q, J=6.7 Hz, 1H), 4.02 (dd, J=9.6, 6.2 Hz, 1H), 3.14 (d, J=6.3 Hz, 1H), 3.00 (d, J=6.2 Hz, 1H), 2.96-2.87 (m, 2H), 2.80-1.21 (m, 37H).

LRf isomer 95

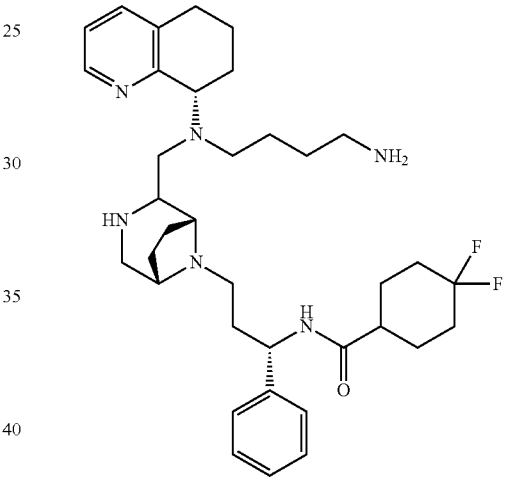

A 20 mL vial equipped with magnetic stir bar was charged with 90.0 mg of LRf isomer 94 (0.120 mmol, 1 equiv.) and 0.651 mL of the 24% hydrazine solution in water (1.20 mmol, 10 equiv.) dissolved in 1.2 mL of methanol. After stirring at rt for 12 h, the reaction mixture was quenched by addition of 2M KOH solution, extracted with $CH_2Cl_2$ (3×) and dried over $Na_2SO_4$. The organics were concentrated and the crude product was purified on silica gel column (12 g) using 0-100% of solvent 2 (solvent 2=30% MeOH in $CH_2Cl_{2+3}$% $NH_4OH$) in $CH_2Cl_2$ as eluent. The product is too polar and the column is too large. All fractions were combined and the purification was repeated on 4 g column affording 45 mg (60%) of N-((1S)-3-((1R,5S)-2-(((4-aminobutyl)((S)-5,6,7,8-tetrahydroquinolin-8-yl)amino)methyl)-3,8-diazabicyclo[3.2.1]octan-8-yl)-1-phenylpropyl)-4,4-difluorocyclohexane-1-carboxamide (LRf isomer 95) as a yellowish foam.

For $LR_f$ isomer 95: $^1H$ NMR (400 MHz, $CDCl_3$, ppm) δ:8.40 (d, J=4.7 Hz, 1H), 7.41 (d, J=7.7 Hz, 1H), 7.31-7.06 (m, 6H), 6.54 (br s, 1H), 5.01 (q, J=7.6 Hz, 1H), 3.92-3.83 (m, 1H), 3.10-2.57 (m, 11H), 2.45 (d, J=13.7 Hz, 1H), 2.38-1.42 (m, 29H).

Synthesis of Opened Top-Piece Analogs

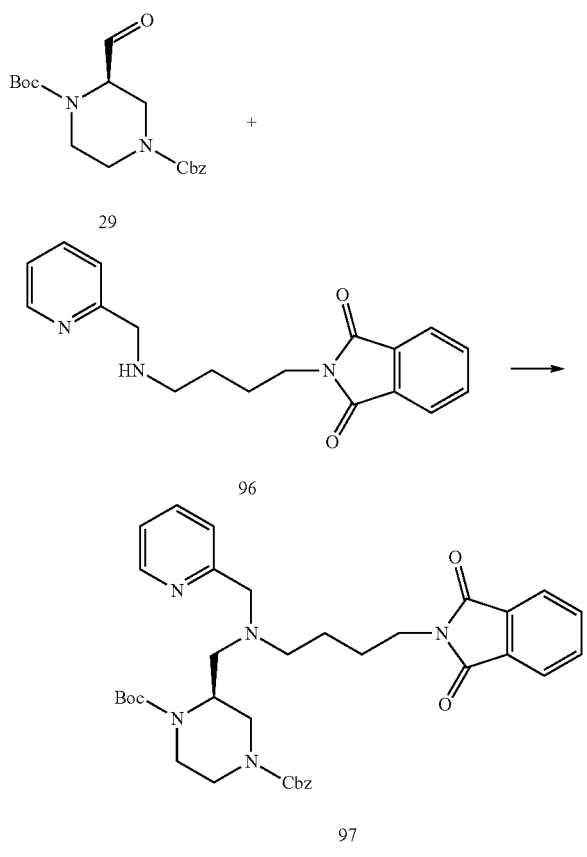

A 100 mL rb flask equipped with a stir bar was charge with 1.31 g of the aldehyde 29 (3.76 mmol, 1 equiv.), 1.34 g of the amine 96 (see synthesis in *ACS Med. Chem. Lett.*, 2018, 9, 17-22) (4.32 mmol, 1.15 equiv.), 1.20 g of NaBH(OAc)$_3$ (5.64 mmol, 1.5 equiv.) and 15 mL of CH$_2$Cl$_2$ and the suspension was stirred at rt for 12 h. Then the reaction mixture was quenched by addition of sat. NaHCO$_3$sol., and the product was extracted with CH$_2$Cl$_2$ (3×) and dried over Na$_2$SO$_4$. The crude product was purified on silica gel column (80 g) using 0-70% EA in hexanes as eluent affording 1.85 g (77%) of 4-benzyl 1-(tert-butyl) (S)-2-(((4-(1,3-dioxoisoindolin-2-yl)butyl)(pyridin-2-ylmethyl)amino)methyl)piperazine-1,4-dicarboxylate 97 as a yellow oil. Later, when the bottom chain is installed, racemization got identified.

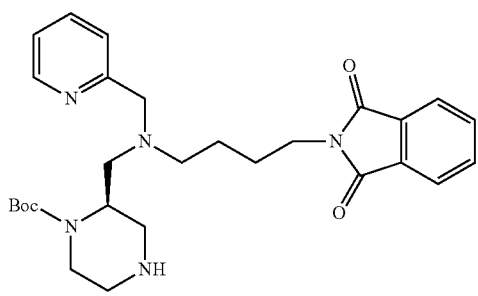

A 100 mL rb flask equipped with a stir bar and rubber septum was charged with 1.80 g of the carbamate 97 (2.80 mmol, 1 equiv.), 390 mg of 20 w % of Pd(OH)$_2$ on carbon (0.560 mmol, 0.2 equiv.) and 20 mL of dry ethanol. Then 710 mg of NH$_4$OOCH (11.2 mmol, 4 equiv.) was added in one portion and heated with heat-gun till bubbling to initiate the catalyst. After stirring at rt for 5 h, more 710 mg of NH$_4$OOCH (11.2 mmol, 4 equiv.) was added and the reaction mixture was stirred for 12 h. Then more 710 mg of NH$_4$OOCH (11.2 mmol, 4 equiv.) was added. After stirring at rt for 24 h, the reaction mixture was filtered through celite plug and the celite plug was washed with ethanol. The organics were concentrated in vacuo (rotatory evaporator) and the crude product was dissolved in CH$_2$Cl$_2$ and sat. Na$_2$CO$_3$ solution was added, the product was extracted with CH$_2$Cl$_2$ (3×) and dried over Na$_2$SO$_4$. The crude product was purified on silica gel column (30 g) using 0 to 30% Solv2 (Solv2=30% MeOH in CH$_2$Cl$_2$ with 3% NH$_4$OH) in CH$_2$Cl$_2$ as eluent affording 841 mg (59%) of tert-butyl (R)-2-(((4-(1,3-dioxoisoindolin-2-yl)butyl)(pyridin-2-ylmethyl)amino)methyl)piperazine-1-carboxylate 98 as a yellow oil. TLC conditions: 20% MeOH in EA.

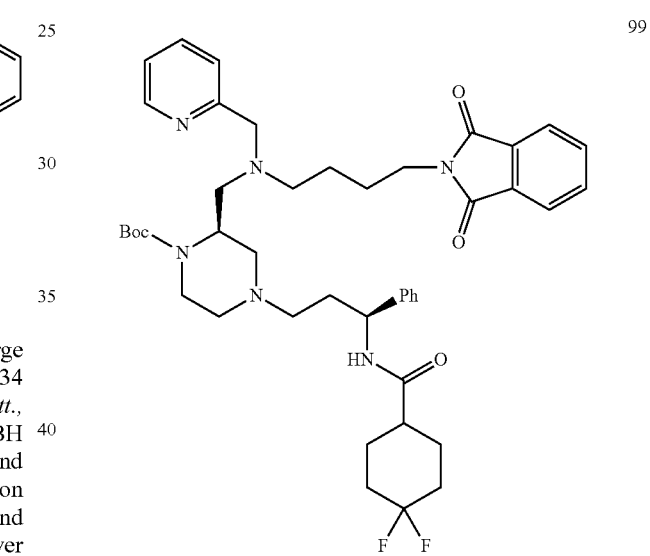

A 100 mL rb flask equipped with a stir bar was charged with 0.610 g of (S)-4,4-difluoro-N-(3-oxo-1-phenylpropyl)cyclohexane-1-carboxamide 6 (2.07 mmol, 1.3 equiv.), 0.810 g of the amine 98 (1.60 mmol, 1 equiv.), 18 µL of acetic acid (0.320 mmol, 0.2 equiv.) and 10 mL of DCE. Then 0.570 g of NaBH(OAc)$_3$ (2.71 mmol, 1.7 equiv.) was added and the suspension was stirred at rt for 5 h. The reaction mixture was quenched by addition of sat. Na$_2$CO$_3$ solution, extracted with CH$_2$Cl$_2$ (3×) and dried over Na$_2$SO$_4$. The crude product is purified on silica gel column (40 g) using 0 to 100% EA in hexanes as eluent affording 0.924 g (74%) of tert-butyl (R)-4-((S)-3-(4,4-difluorocyclohexane-1-carboxamido)-3-phenylpropyl)-2-(((4-(1,3-dioxoisoindolin-2-yl)butyl)(pyridin-2-ylmethyl)amino)methyl)piperazine-1-carboxylate 99 as a white foam. ~3:1 d.r. was noticed by $^{13}$C NMR.

100

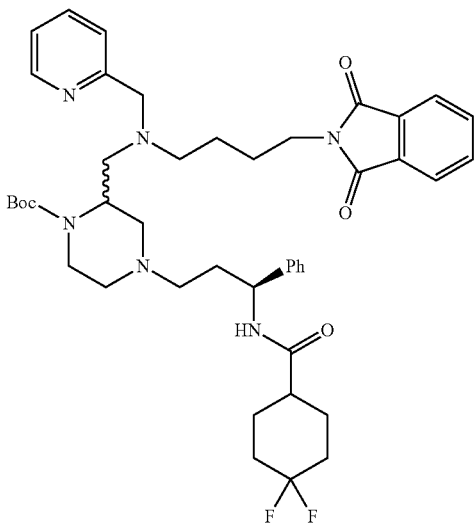

A 20 mL vial equipped with a stir bar was charged with 530 mg of the amine 99 (0.664 mmol, 1 equiv.) dissolved in 6.6 mL of CH$_2$Cl$_2$. Then 1.56 mL of CF$_3$COOH (20.1 mmol, 30 equiv.) was added. After stirring at rt for 5 h, the reaction mixture was cooled in an ice bath and quenched by addition of 2 N NaOH solution till pH=11, extracted with CH$_2$Cl$_2$ (3×) and dried over Na$_2$SO$_4$. The crude material was purified on silica gel column using 0-50% Solvent 2 (solvent 2=70% CH$_2$Cl$_2$, 30% MeOH, 3% NH$_4$OH) in CH$_2$Cl$_2$ as eluent affording 413 mg (89%) of N-((1 S)-3-(3-(((4-(1,3-dioxoisoindolin-2-yl)butyl)(pyridin-2-ylmethyl)amino)methyl)piperazin-1-yl)-1-phenylpropyl)-4,4-difluorocyclohexane-1-carboxamide 100 as a yellowish foam.

101

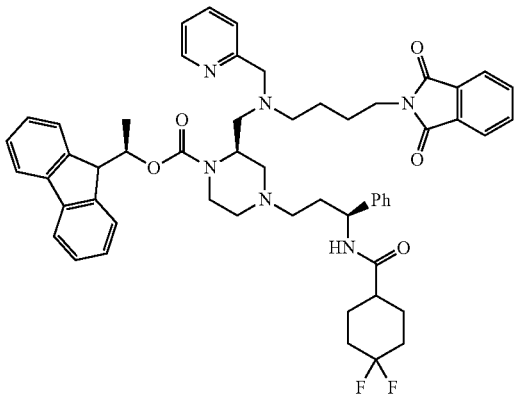

A 20 mL vial equipped with magnetic stir bar was charged with 65.8 mg of triphosgene (0.229 mmol, 0.410 equiv.) and 5.4 mL of CH$_2$Cl$_2$. Then 137 mg of (R)-1-(9H-fluoren-9-yl)ethan-1-ol (0.650 mmol, 1.2 equiv.) was added, followed by 52.0 µL of pyridine (0.650 mmol, 1.2 equiv.) at 0° C. After stirring at rt for 2 h, the reaction mixture was washed with water (3×) and dried over Na$_2$SO$_4$. The organics were concentrated and dissolved in 4.0 mL dry CH$_2$Cl$_2$. Then 373 mg of the amine 100 (0.540 mmol, 1 equiv.) dissolved in 1.4 mL of CH$_2$Cl$_2$ was added at 0° C., followed by 120 µL of NEt(iPr)$_2$ (0.710 mmol, 1.3 equiv.) and the stirring was continued at rt for 12h. The reaction mixture was diluted with CH$_2$Cl$_2$, washed with water, brine and dried over Na$_2$SO$_4$. The crude material was purified on silica gel column (10 g) using 0-100% EA in hexanes as eluent affording 337 mg (10:1 d.r.) and 174 mg (1:1 d.r.) of the product. The first fraction was repurified affording 189 mg (38%) of (R)-1-(9H-fluoren-9-yl)ethyl (R)-4-((S)-3-(4,4-difluorocyclohexane-1-carboxamido)-3-phenylpropyl)-2-(((4-(1,3-dioxoisoindolin-2-yl)butyl)(pyridin-2-ylmethyl)amino)methyl)piperazine-1-carboxylate 101 as a white foam and 79 mg of a mixed fraction.

102

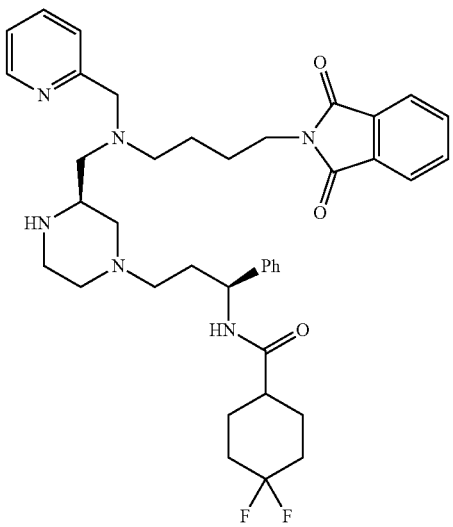

A 20 mL vial equipped with a magnetic stir bar was charged with 250 mg of the amine 101 (0.260 mmol, 1 equiv.) and 2.6 mL of CH$_2$Cl$_2$. Then 520 µL of piperidine (5.26 mmol, 20 equiv.) was added and the solution was stirred at rt for 1 h. The reaction mixture was quenched by the addition of water and the product was extracted with CH$_2$Cl$_2$ (3×), washed with water (2×), and dried over Na$_2$SO$_4$. The LCMS shoved the product and the product and piperidine adduct. Next time shorter reaction time and less equivalents of piperidine should be used. The crude material 102 was submitted to next reaction.

103

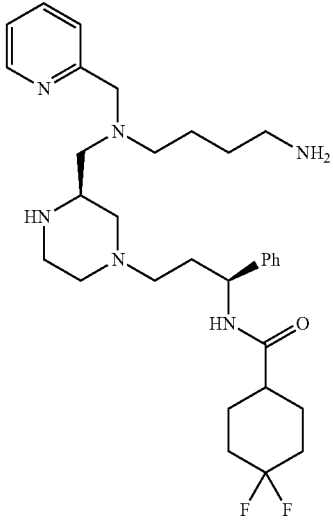

A 20 mL vial equipped with magnetic stir bar was charged with 126 mg of the amine 102 (0.180 mmol, 1 equiv.) and 0.490 mL of the 24% hydrazine solution in water (3.67 mmol, 10 equiv.) dissolved in 6.6 mL of methanol. After stirring at rt for 12 h, the reaction mixture was partially concentrated on rotavap (60° C.), quenched by addition of 2M KOH solution, extracted with $CH_2Cl_2$ (3×) and dried over $Na_2SO_4$. The organics were concentrated and the crude product was purified on silica gel column (30 g) using 0-60% of solvent 2 (solvent 2=30% MeOH in $CH_2Cl_{2+3}$% $NH_4OH$) in $CH_2Cl_2$ as eluent affording 67.0 mg of N—((S)-3-((R)-3-(((4-aminobutyl)(pyridin-2-ylmethyl)amino)methyl)piperazin-1-yl)-1-phenylpropyl)-4,4-difluorocyclohexane-1-carboxamide 103 as a white foam. $^1$H NMR (400 MHz, $CDCl_3$, ppm) δ: 8.54-8.52 (m, 1H), 7.97 (d, J=7.0 Hz, 1H), 7.64 (td, J=7.7, 1.8 Hz, 1H), 7.34 (d, J=7.8 Hz, 1H), 7.31-7.25 (m, 2H), 7.25-7.15 (m, 3H), 7.15 (dd, J=7.6, 4.9 Hz, 1H), 5.04 (q, J=6.1 Hz, 1H), 3.78 (A of AB, $J_{AB}$=14.7 Hz, 1H), 3.66 (B of AB, $J_{AB}$=14.7 Hz, 1H), 3.19 (br s, 3H), 3.06 (dt, J=11.8, 2.8 Hz, 1H), 2.91-2.78 (m, 4H), 2.74 (d, J=11.2 Hz, 1H), 2.68 (t, J=6.6 Hz, 2H), 2.58-1.39 (m, 23H).

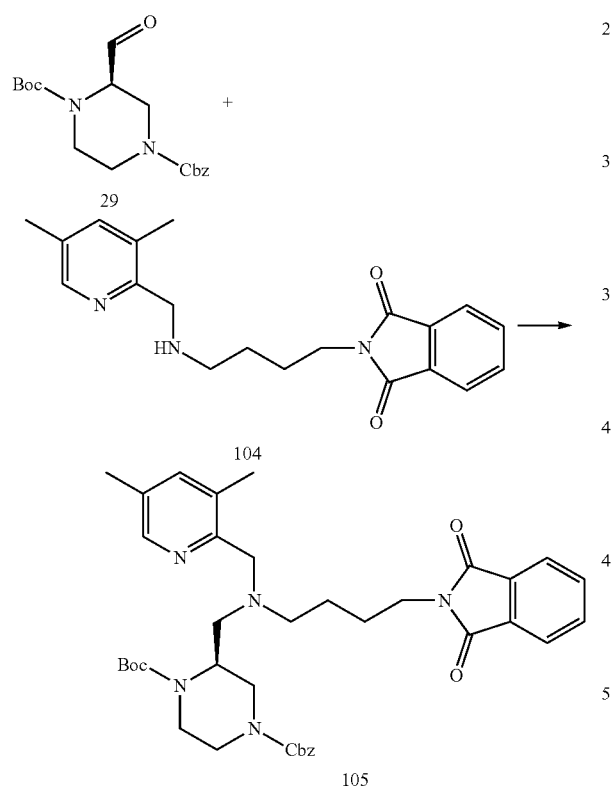

A 100 mL rb flask equipped with a stir bar was charge with 1.92 g of the aldehyde 29 (5.51 mmol, 1 equiv.), 2.14 g of the amine 104 (see synthesis in *ACS Med. Chem. Lett.*, 2018, 9, 17-22) (6.34 mmol, 1.15 equiv.), 1.99 g of NaBH(OAc)$_3$ (9.37 mmol, 1.7 equiv.) and 22 mL of $CH_2Cl_2$ and the suspension was stirred at rt for 12 h. Then the reaction mixture was quenched by addition of sat. $NaHCO_3$ sol., and the product was extracted with $CH_2Cl_2$ (3×) and dried over $Na_2SO_4$. The crude product was purified on silica gel column (80 g) using 0-60% EA in hexanes as eluent affording 2.63 g (71%) of 4-benzyl 1-(tert-butyl) (S)-2-((((3,5-dimethylpyridin-2-yl)methyl)(4-(1,3-dioxoisoindolin-2-yl)butyl)amino)methyl)piperazine-1,4-dicarboxylate 105 as a yellow oil. Later, when the bottom chain is installed, racemization got identified.

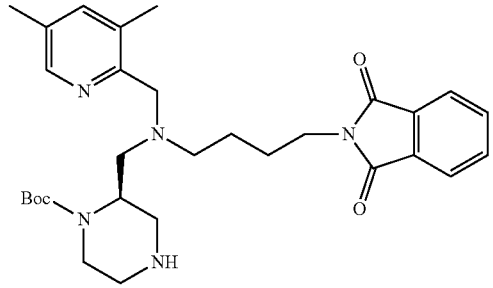

A 100 mL rb flask equipped with a stir bar and rubber septum was charged with 2.60 g of the carbamate 105 (3.88 mmol, 1 equiv.), 550 mg of 20 w % of $Pd(OH)_2$ on carbon (0.780 mmol, 0.2 equiv.), 1.96 g of $NH_4OOCH$ (31.1 mmol, 4 equiv.) and 27 mL of dry ethanol. Then the reaction mixture was heated with a heat-gun till bubbling to initiate the catalyst. After stirring at rt for 48 h, more 1.96 g of $NH_4OOCH$ (31.1 mmol, 4 equiv.) was added and the reaction mixture was stirred for 24 h. The reaction mixture was filtered through celite plug and the celite plug was washed with ethanol. The organics were concentrated under vacuum (rotatory evaporator) and the crude product was dissolved in $CH_2Cl_2$ and sat. $Na_2CO_3$ solution was added, the product was extracted with $CH_2Cl_2$ (3×) and dried over $Na_2SO_4$. The crude product was purified on silica gel column (40 g) using 0 to 30% Solv2 (Solv2=30% MeOH in $CH_2Cl_2$ with 3% $NH_4OH$) in $CH_2Cl_2$ as eluent affording 1.22 g (59%) of tert-butyl (R)-2-((((3,5-dimethylpyridin-2-yl)methyl)(4-(1,3-dioxoisoindolin-2-yl)butyl)amino)methyl)piperazine-1-carboxylate 106 as a yellow oil.

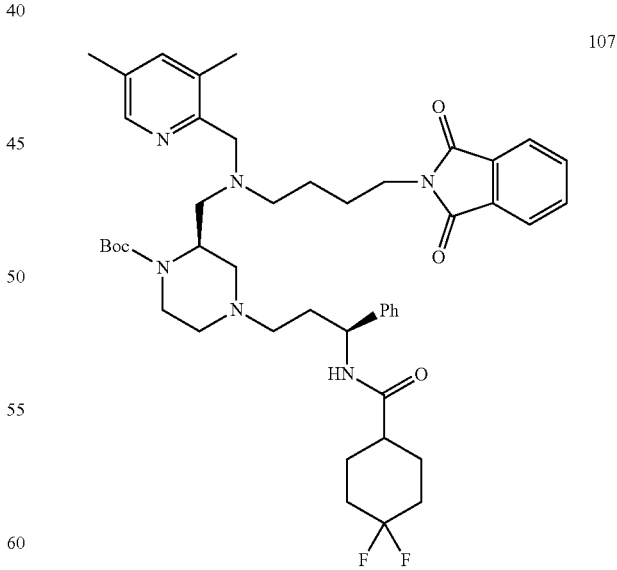

A 100 mL rb flask equipped with a stir bar was charged with 1.11 g of (S)-4,4-difluoro-N-(3-oxo-1-phenylpropyl)cyclohexane-1-carboxamide (3.77 mmol, 1.3 equiv.), 1.56 g of the amine 106 (2.90 mmol, 1 equiv.), 33 μL of acetic acid (0.580 mmol, 0.2 equiv.) and 28 mL of DCE. Then 1.05 g of NaBH(OAc)$_3$ (4.93 mmol, 1.7 equiv.) was added and the suspension was stirred at rt for 12 h. The reaction mixture was quenched by addition of sat. Na$_2$CO$_3$ solution, extracted with CH$_2$Cl$_2$ (3×) and dried over Na$_2$SO$_4$. The crude product was purified on silica gel column (80 g) using 0 to 100% EA in hexanes as eluent affording 2.22 g (94%) of tert-butyl (R)-4-((S)-3-(4,4-difluorocyclohexane-1-carboxamido)-3-phenylpropyl)-2-((((3,5-dimethylpyridin-2-yl)methyl)(4-(1,3-dioxoisoindolin-2-yl)butyl)amino)methyl)piperazine-1-carboxylate 107 as a white foam. ~6:1 d.r. was noticed by $^{13}$C NMR.

108

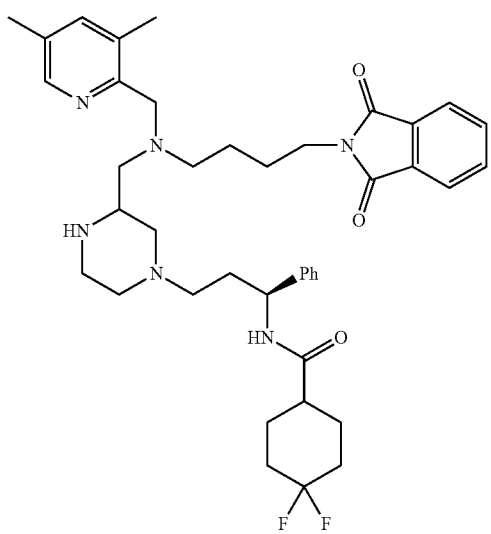

A 100 mL rb flask equipped with a stir bar was charged with 1.91 g of the amine 107 (2.34 mmol, 1 equiv.) dissolved in 22 mL of CH$_2$Cl$_2$. Then 5.42 mL of CF$_3$COOH (70.3 mmol, 30 equiv.) was added. After stirring at rt for 5 h, the reaction mixture was cooled in an ice bath and quenched by addition of 2 N NaOH solution till pH=11, extracted with CH$_2$Cl$_2$ (3×) and dried over Na$_2$SO$_4$. The crude material was purified on silica gel column (30 g) using 0-30% Solvent 2 (solvent 2=70% CH$_2$Cl$_2$, 30% MeOH, 3% NH$_4$OH) in CH$_2$Cl$_2$ as eluent affording 1.51 g (90%) of N-((1S)-3-(3-((((3,5-dimethylpyridin-2-yl)methyl)(4-(1,3-dioxoisoindolin-2-yl)butyl)amino)methyl)piperazin-1-yl)-1-phenylpropyl)-4,4-difluorocyclohexane-1-carboxamide 108 as a yellowish foam.

109

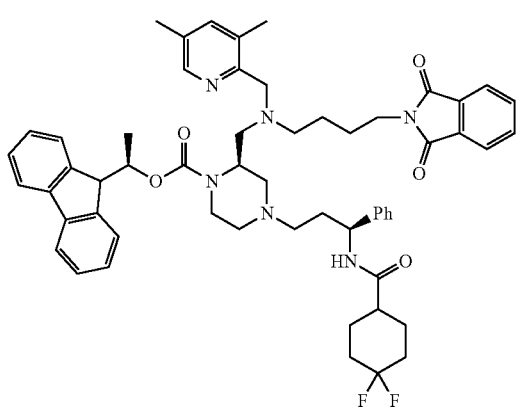

A 100 mL rb flask equipped with a magnetic stir bar was charged with 251 mg of triphosgene (0.840 mmol, 0.410 equiv.) and 20 mL of CH$_2$Cl$_2$. Then 522 mg of (R)-1-(9H-fluoren-9-yl)ethan-1-ol (2.48 mmol, 1.2 equiv.) was added, followed by 200 µL of pyridine (2.48 mmol, 1.2 equiv.) at 0° C. After stirring at rt for 2 h, the reaction mixture was washed with water (3×) and dried over Na$_2$SO$_4$. The organics were concentrated and dissolved in 15 mL dry CH$_2$Cl$_2$. Then 1.480 mg of the amine 108 (2.07 mmol, 1 equiv.) dissolved in 5.0 mL of CH$_2$Cl$_2$ was added at 0° C., followed by 458 µL of NEt(iPr)$_2$ (2.69 mmol, 1.3 equiv.) and the stirring was continued at rt for 2 h. The reaction mixture was diluted with CH$_2$Cl$_2$, washed with water, brine and dried over Na$_2$SO$_4$. The crude material was purified on silica gel column (120 g) using 0-100% EA in hexanes as eluent affording 1.23 g of (R)-1-(9H-fluoren-9-yl)ethyl (R)-4-((S)-3-(4,4-difluorocyclohexane-1-carboxamido)-3-phenylpropyl)-2-((((3,5-dimethylpyridin-2-yl)methyl)(4-(1,3-dioxoisoindolin-2-yl)butyl)amino)methyl)piperazine-1-carboxylate 109 (>99:1 d.r., 62%) as a white foam white foam and 523 mg (3:1 d.r.) of the other fraction of the product.

110

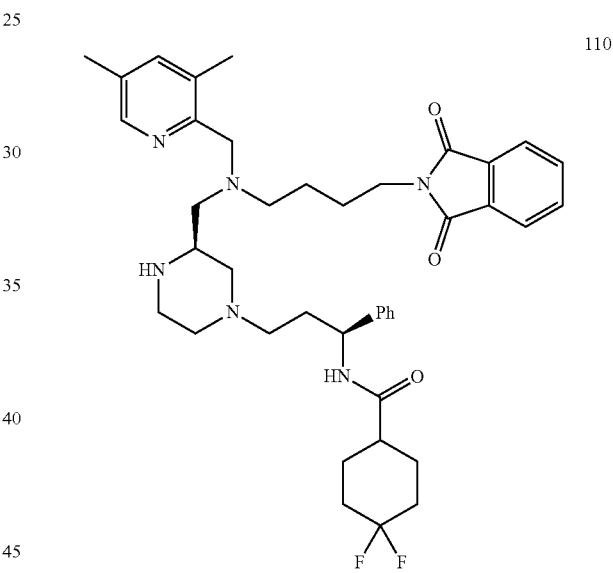

A 20 mL vial equipped with a magnetic stir bar was charged with 170 mg of the amine 109 (0.184 mmol, 1 equiv.) and 1.8 mL of CH$_2$Cl$_2$. Then 55.0 µL of piperidine (0.550 mmol, 3 equiv.) was added and the solution was stirred at rt for 1 h. No reaction was observed. Then 27.8 µL of DBU (0.184 mmol, 1 equiv.) was added and the stirring was continued at rt for 3h. The reaction mixture was diluted by addition of CH$_2$Cl$_2$, washed with water and brine, and dried over Na$_2$SO$_4$. The LCMS shoved the product and the product and piperidine adduct. Next time other nucleophilic amine should be used, like piperazine. The crude material 110 was submitted to next reaction.

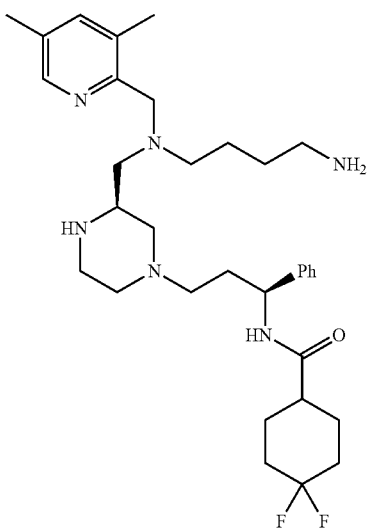

A 20 mL vial equipped with magnetic stir bar was charged with 188 mg of the amine 110 (0.260 mmol, 1 equiv.) and 0.350 mL of the 24% hydrazine solution in water (2.63 mmol, 10 equiv.) dissolved in 2.6 mL of methanol. After stirring at rt for 12 h, more 0.750 mL of the 24% hydrazine (0.520 mmol, 20 equiv.) and 2.6 mL of MeOH was added and the stirring was continued for 12 h. Then the reaction mixture was partially concentrated on rotatory evaporator (60° C.), quenched by addition of 2M KOH solution, extracted with $CH_2Cl_2$ (3×) and dried over $Na_2SO_4$. The organics were concentrated and the crude product was purified on silica gel column (30 g) using 0-60% of solvent 2 (solvent 2=30% MeOH in $CH_2Cl_{2+3}$% $NH_4OH$) in $CH_2Cl_2$ as eluent affording 113 mg of the product as a white foam. Still minor impurity, the product was repurified on silica gel column (10 g) again affording 93 mg (60%) of N—((S)-3-((R)-3-(((4-aminobutyl)((3,5-dimethylpyridin-2-yl)methyl)amino)methyl)piperazin-1-yl)-1-phenylpropyl)-4,4-difluorocyclohexane-1-carboxamide 111 as a white foam. $^1$H NMR (400 MHz, $CDCl_3$, ppm) δ: 8.16 (d, J=2.1 Hz, 1H), 7.94 (d, J=7.1 Hz, 1H), 7.28-7.20 (m, 3H), 7.19-7.13 (m, 3H), 4.98 (q, J=6.3 Hz, 1H), 3.70 (A of AB, $J_{AB}$=16.6 Hz, 5H), 3.68 (br s, 3H), 3.58 (B of AB, $J_{AB}$=13.4 Hz, 1H), 3.00 (d, J=12.0 Hz, 1H), 2.89-1.34 (m, 31H), 2.29 (s, 3H), 2.22 (s, 3H).

Biological Assays

HIV-1 and MAGI Tropism assays can be used to establish activity/cytotoxicity and synergy studies and ADME profiles of compounds are evaluated using in vitro assays such as CYP2D6/3A4 assays and metabolic stability in human and mouse liver microsomes (See Tables 2 and 3).

Human Liver Microsomes: Pooled mixed gender human liver microsomes at a concentration of 20 mg/mL were purchased from XenoTech (Kansas City, Kans.). The vials of microsomes were stored at −80° C. and thawed on ice before each experiment. The microsomes were diluted to 1 mg/mL with 100 mM potassium phosphate buffer (pH 7.4).

Mouse Liver Microsomes: Pooled CD-1 mouse liver microsomes at a concentration of 20 mg/mL were purchased from XenoTech (Kansas City, Kans.). The vials of microsomes were stored at −80° C. and thawed on ice before each experiment. The microsomes were diluted to 1 mg/mL with 100 mM potassium phosphate buffer (pH 7.4).

Experimental Conditions: Test compounds were weighed and dissolved in 100% acetonitrile to make 2 mM stock solutions. Verapamil (human, Sigma Aldrich) and diphenhydramine (mouse, Sigma Aldrich) served as positive controls and were dissolved in 100% acetonitrile to make 2 mM stock solutions. The 2 mM stock solution of test and control compounds were further diluted in sodium phosphate buffer (100 mM, pH 7.4) to 50 μM to ensure the acetonitrile content was <0.2%.

The liver microsome assay was prepared in a 1.5 mL Eppendorf tube (Fisher Scientific) with a final volume of 1100 μL. Each reaction contained sodium phosphate buffer, liver microsomes (1 mg/mL), and test compound resulting in a final concentration of 3 μM. Following a 5 min pre-incubation of drug and microsomes in a 37° C. shaking incubator, the reaction was initiated with NADPH (110 μL). Aliquots (100 μL) were removed in duplicate at 0, 5, 10, 15, and min time intervals and quenched in cold acetonitrile (200 μL). The aliquots were centrifuged at 12,000 g for 5 min and the supernatant removed and placed in an LCMS vial. Positive controls were conducted at a final volume of 600 μL to give each time point in a singlet run. A no NADPH negative control with test and control compound was conducted in singlet (150 μL) at the longest time point. Controls were processed and analyzed like test compounds.

LC/MS Analysis

An Agilent Technologies LCMS system consisting of an Agilent 6120 quadrupole mass spectrometer equipped with an Agilent 1200 binary pump, degasser, and auto sampler (Santa Clara, Calif.). The analytical column used for analysis was an XDB-Eclipse Plus C18 column (4.6 mm×150 mm column; Agilent Technologies). The mobile phase for the HPLC was 50 mM ammonium formate buffer, pH 3.5 (A) and acetonitrile (B). The samples were analyzed using the following 8-minute method: A linear gradient from 10% B to 95% B over for 5 minutes, with a 3 min hold at 95%. An equilibration at 10% B for 5 min was conducted after each run. Sample injection volume was 10 μL and the flow rate was 1.0 mL/min. Single ion monitoring of the mass in positive mode was conducted the molecular weight for each compound. Each time point was assessed on the LCMS and the area, based on the extracted ion, was manually integrated.

Calculations: The depletion of the compound was monitored as a function of time, and the area under the curve was manually integrated. The relative percent remaining was calculated using: Relative % remaining=$Area_{Time}$/$Area_{Time=0}$*100. The relative percentages for the duplicate runs were averaged and the standard deviations were calculated. Metabolism data averaged duplicates.

| Human Liver Microsomes Assay | | |
|---|---|---|
| Compound | 10 min | 30 min |
| 1 | 58 ± 4.9% | 25 ± 0.1% |
| 2 | 65 ± 8.6% | 78 ± 2.2% |
| Verapamil | 26 ± 1.5% | 8.0 ± 3.0% |

| Mouse, Liver Microsomes Assay | | |
|---|---|---|
| Compound | 10 min | 30 min |
| 1 | 116 ± 3.1% | 93 ± 8.9% |
| 2 | 95 ± 7.2% | 96 ± 6.5% |
| Diphenhydramine | 64 ± 3.1% | 25 ± 4.1% |

Recombinant CYP Inhibition Assay: In a drug discovery program, a rapid screening for cyctochrome P450 (CYP450) inhibitors is a part of the existing standard for avoiding the development of drugs likely to give clinical pharmacokinetic drug-drug interactions and associated toxicities. A microtiter plate-based, direct fluorometric assay for the activities of the principal human drug-metabolizing enzymes, CYP2D6 and CYP3A4 can be used and these assays are rapid and compatible with existing high-throughput assay instrumentation.

Fluorometric Enzyme Inhibition Assays: Test compounds were dissolved in 100% organic solvent ($CH_3CN$ or DMSO) to make 30 mM stock solutions. Quinidine (CYP2D6 assay, Sigma Aldrich) and ketoconazole (CYP3A4 assay, Sigma Aldrich) ran as positive controls and were dissolved in 100% acetonitrile to make 1 mM stock solutions. A 100 mM potassium phosphate buffer was prepared and adjusted to pH 7.4. The 30 mM stock solution of test and control compounds (1 mM) were further diluted in phosphate buffer (100 mM, pH 7.4) to ensure the final organic solvent content was <0.2% in the reaction. In a separate falcon tube, a 2× enzyme/substrate (E/S) solution was prepared in phosphate buffer. The final concentration of CYP2D6 (Corning) and AMMC was 10 nM and 4 μM, and CYP3A4 (Corning) and BFC was 20 nM and 40 μM, respectively. In a separate falcon tube, a 2× NADPH regenerating system (NRS) was prepared in phosphate buffer. The final concentration for each component in the assay was as follows:

CYP2D6 assay=0.008 mM NADPH, 3.3 mM glucose 6-phosphate, 0.4 U of glucose-6-phosphate dehydrogenase/mL CYP3A4 assay=2.45 mM NADPH, 24.7 mM glucose 6-phosphate, 1.25 U of glucose-6-phosphate dehydrogenase/mL Both enzymatic assays were conducted in a 96-well microtiter plate (Black, Corning Costar) with a final volume of 100 μL. Preparation of the plate began with the addition of 74 μL of the E/S in the first well, and 50 μL to all subsequent wells (from 2-11). The test compounds (1 μL) were dissolved in the first well to give the first row a final volume of 75 μL. A 1:3 serial dilution of the test compound was conducted by removing 25 μL from the first well and diluting it with the second and so forth until the tenth row. Final concentrations yielded a range from 300 μM-0.01 μM. Well 11 contained no enzyme, and well 12 contained no inhibitor. Both were used as controls for background fluorescence. The plate was incubated for 10 min at 37° C. for CYP2D6, and 30 mins for CYP3A4. After incubation, the reaction was initiated by the addition of 50 μL of the 2× NRS to each well.

Immediately (within 1 min) the fluorescence was measured using a microplate reader (KC4, BioTek). CYP2D6 was monitored at Ex/Em=410/460 nm, and CYP3A4 monitored at Ex/Em=410/538 nm in kinetic mode that scanned every 5 min for 60 mins. Data was exported and corrected for background noise by subtracting the blank from the mean value of all other columns. Fluorescence readout was normalized to the fluorescence intensity of the reaction in the absence of the test substance (well 12, 0% inhibition) and the mixture of reaction components in the presence of "inhibitor cocktail" (well 11, 100% inhibition). The percent of inactivated enzyme for each dilution of test compounds or controls (designated as I %): I=(1−(mean of individual column−mean of column 11)/mean of column 12−mean of 11))×100. The $IC_{50}$ value was derived after the data was fitted on a 10-point curve using a four-parameter logistic regression model using Graph Pad Prism 7.

TABLE 2

CYP3A4 and 2D6 IC50 values for the respective compounds.

| Compound | rCYP3A4 ($IC_{50}$) μM | rCYP2D6 ($IC_{50}$) μM |
|---|---|---|
| 1 | 63.46 Range: 43.1 to 118.9 | 58.32 Range: 44.58 to 85.35 |
| 2 | 750.6 Range: >1000 | 156.2 Range: 49.67 to >200 |

TABLE 3

Activity data for selected compounds.

| Compound | MAGI HIV-1$_{IIIB}$ $IC_{50}$, μM | MAGI HIV-1$_{IIIB}$ $IC_{90}$, μM | MAGI HIV-1$_{BaL}$ $IC_{50}$, μM | MAGI HIV-1$_{BaL}$ $IC_{90}$, μM | MAGI HIV-1$_{IIIB}$ $TC_{50}$, μM | MAGI HIV-1$_{BaL}$ $TC_{90}$, μM |
|---|---|---|---|---|---|---|
| 2 | 0.07 | 0.68 | 2.61 | 29.1 | >10.0 | 33.1 |
| 66 | 12.4 | 65.8 | 0.33 | 4.38 | >100 | >100 |
| 67 | 3.19 | 44.6 | 2.33 | 36.7 | >100 | >100 |
| 68 | 10.2 | 70.2 | 4.16 | 66.8 | >100 | >100 |
| 77 | 0.002 | 0.009 | 1.54 | 23.0 | >100 | >100 |
| 75 | 6.61 | 68.5 | 2.51 | 97.1 | >100 | >100 |
| 79 | 2.58 | 36.5 | 0.66 | 7.35 | >100 | >100 |
| 81 | 3.49 | 52.7 | 0.95 | 22.7 | >100 | >100 |
| URf isomer 95 | 0.17 | 0.90 | 0.82 | 8.96 | >10.0 | >100 |
| LRf isomer 95 | >10.0 | >10.0 | 9.36 | >100 | >10.0 | >100 |

The invention claimed is:

1. A compound according to Formula (I) or a salt thereof,

Formula (I)

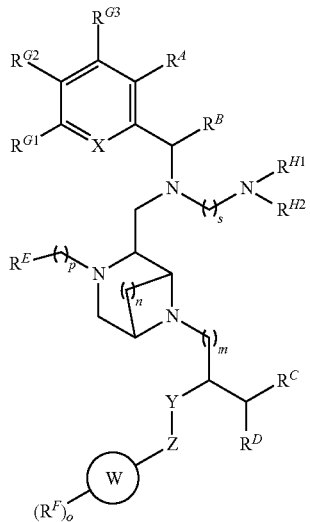

wherein $R^A$, $R^B$, $R^C$ and $R^D$ are individually and independently H, aryl or a C1 to C4 alkyl which may be straight, branched, saturated or unsaturated, or $R^A$ and $R^B$, together with the atoms to which they are attached, or $R^C$ and $R^D$, together with the atoms to which they are attached, are connected to form a carbocycle, heterocarbocycle, aryl or heteroaryl, and $R^A$, $R^B$, $R^C$ and $R^D$ are individually and independently optionally substituted with $R^X$;

wherein $R^E$, $R^{G1}$, $R^{G2}$, $R^{G3}$, $R^{H1}$ and $R^{H2}$ are each individually and independently selected from the group consisting of H, alkyl, carbocycle, heterocarbocycle, aryl and heteroaryl, each of which is optionally substituted with $R^X$;

wherein ring W is a carbocycle, heterocarbocycle, aryl or heteroaryl;

wherein o is 0, 1, 2, 3 or 4;

wherein $R^F$ is a chloro, fluoro, bromo, iodo, C1 to C3 alkyl, trifluoromethyl, or O;

wherein X is a N or a CH;

wherein Y is NH when Z is CO and Y is CO when Z is NH;

wherein n, m and p are each independently 0, 1 or 2; s is 1, 2, 3, 4 or 5; and wherein $R^X$ is a halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, N-methylsulfamoyl, N-ethyl sulfamoyl, N,N-dimethyl sulfamoyl, N,N-diethylsulfamoyl, N-methyl-N-ethyl sulfamoyl, carbocyclyl, aryl, or heterocyclyl.

2. A compound selected from the following structures or a salt thereof:

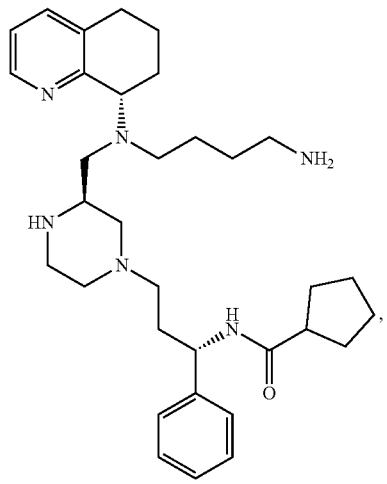

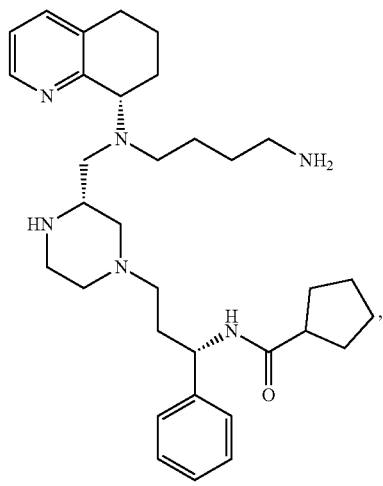

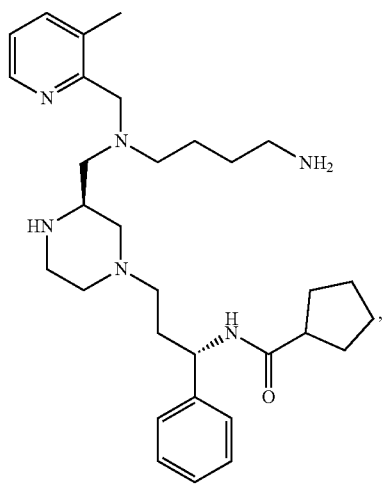

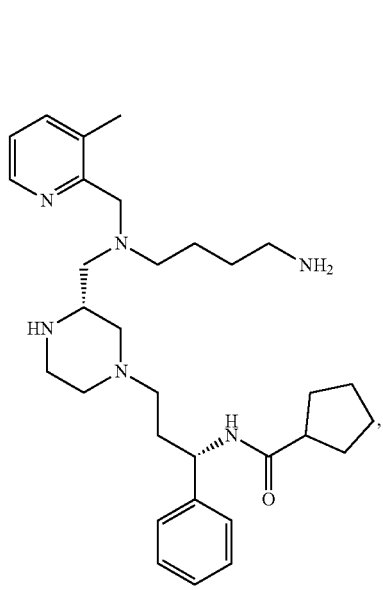

95
-continued
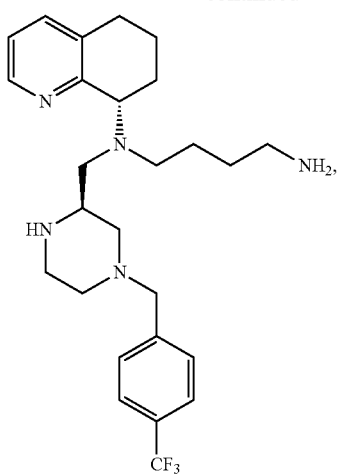
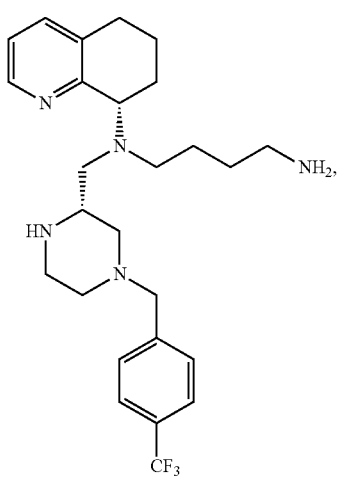
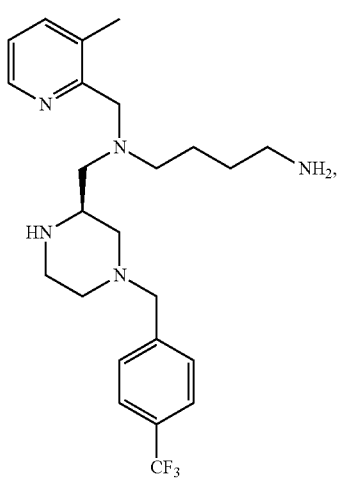
96
-continued
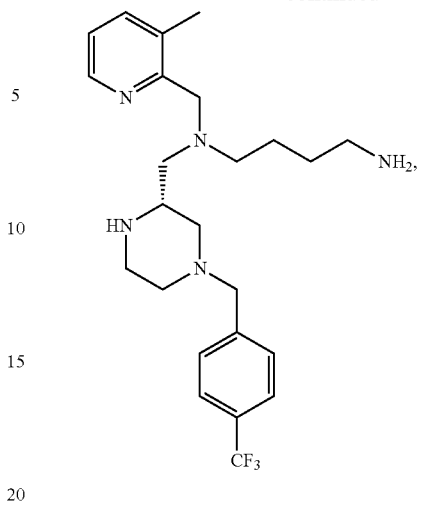
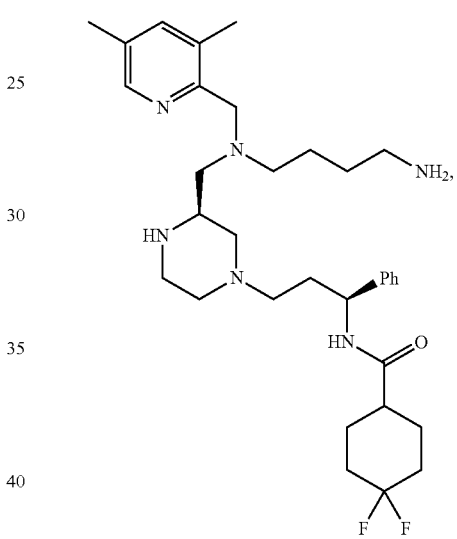
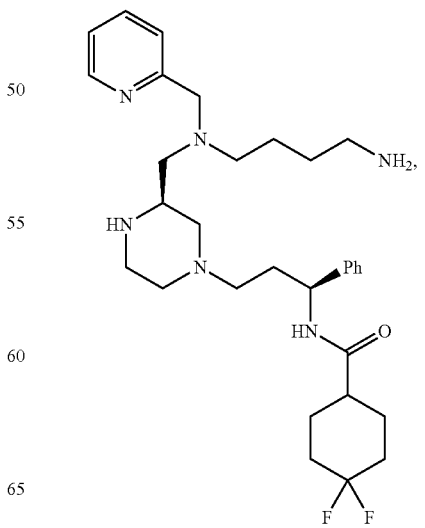

97
-continued
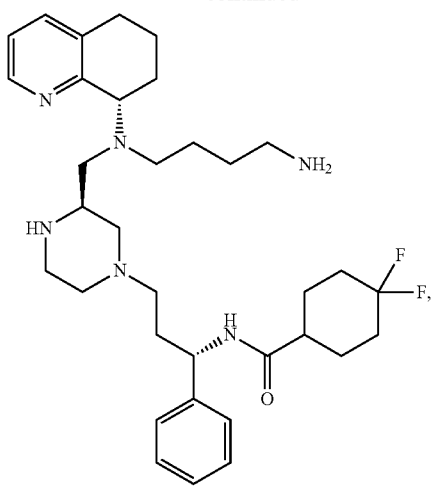
98
-continued
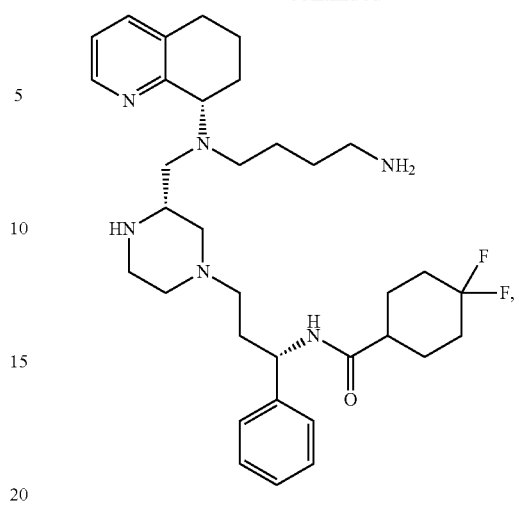
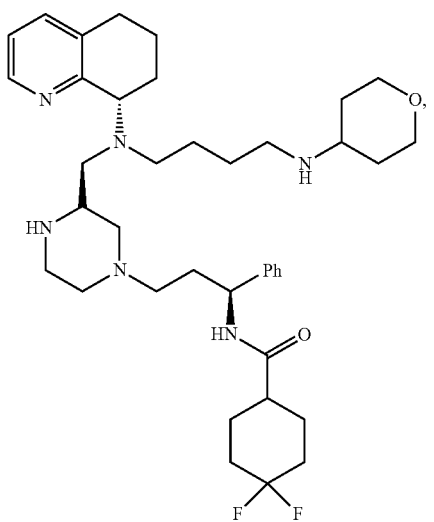
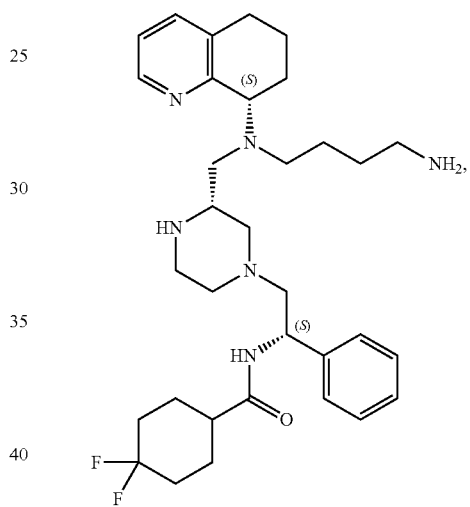
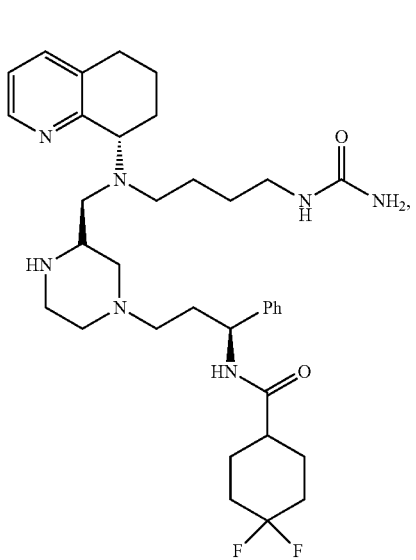
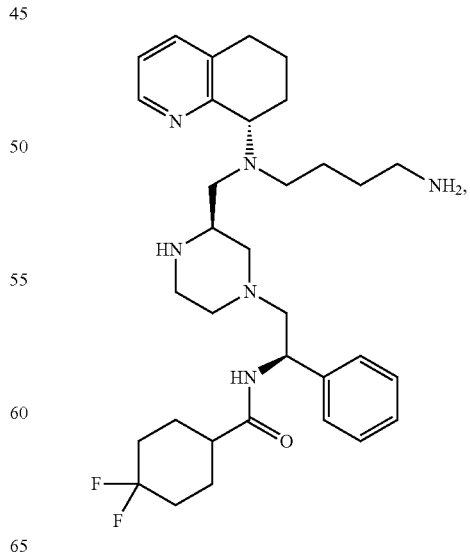

99
-continued
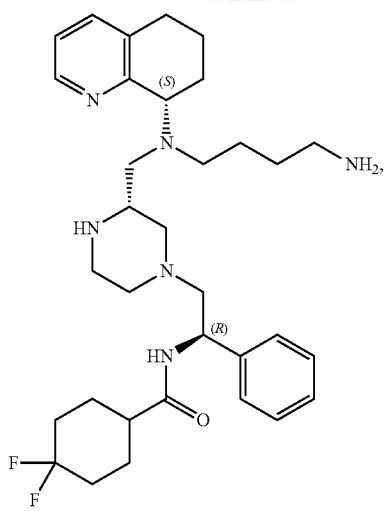
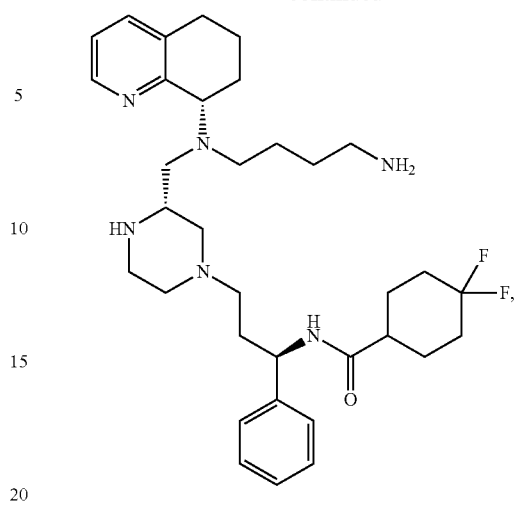
100
-continued
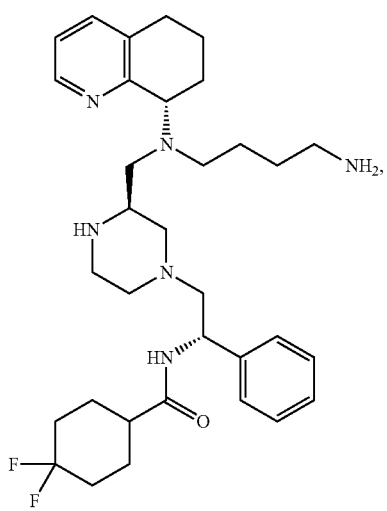
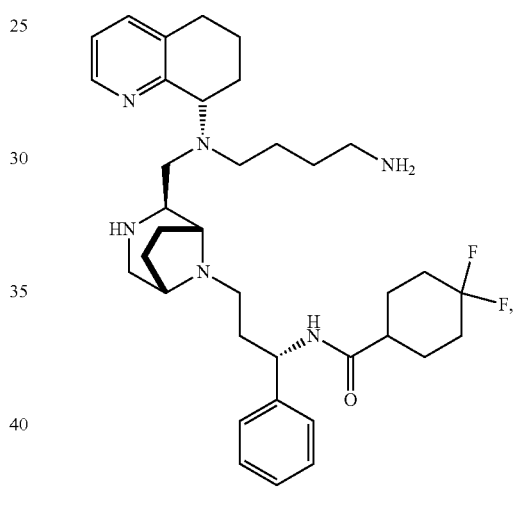
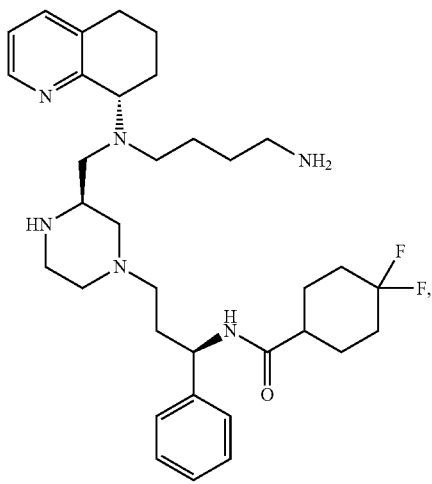
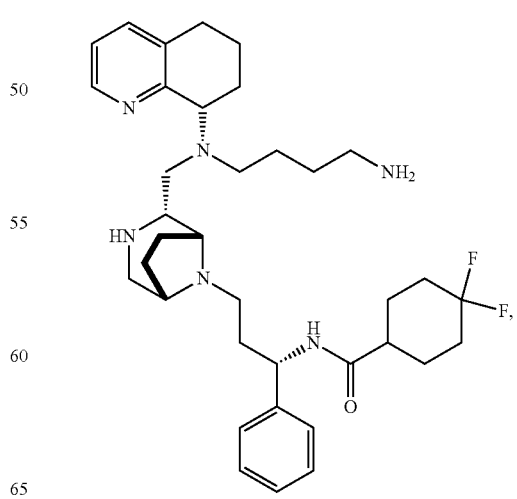

101
-continued
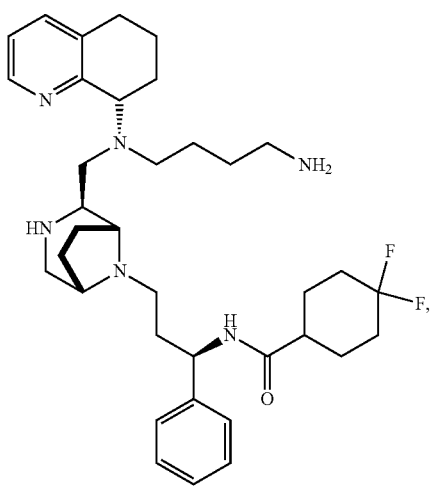
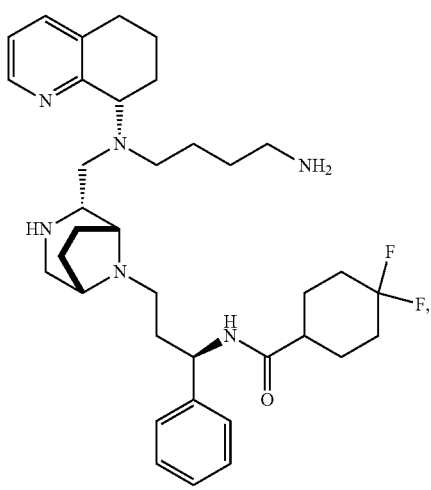
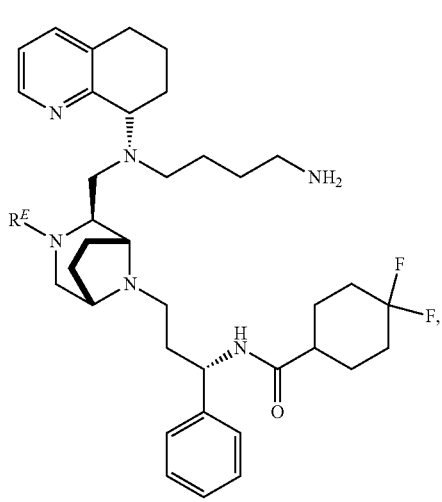
102
-continued
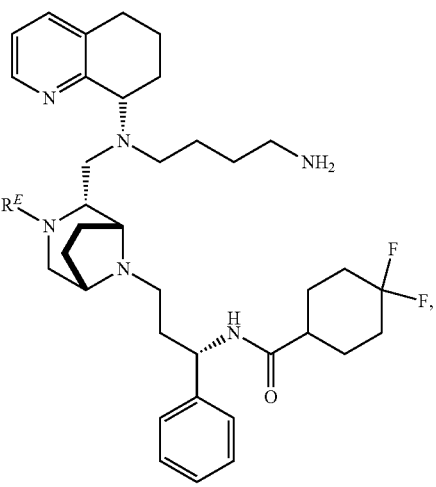
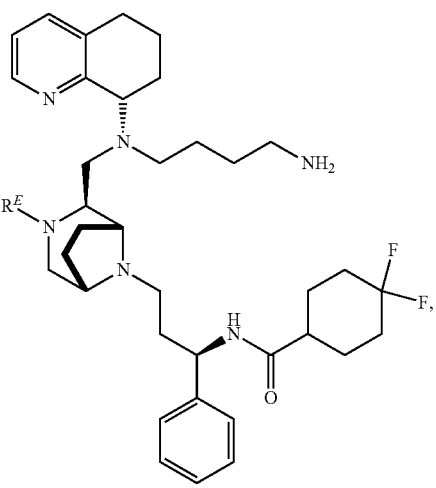
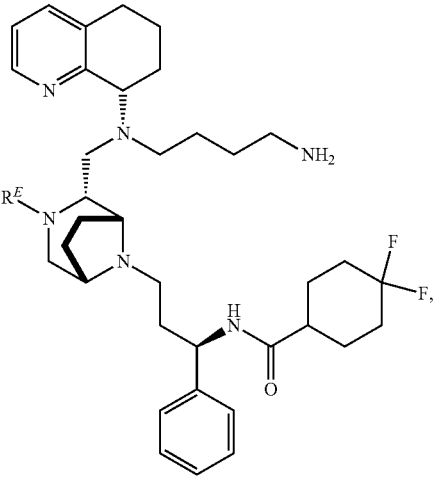

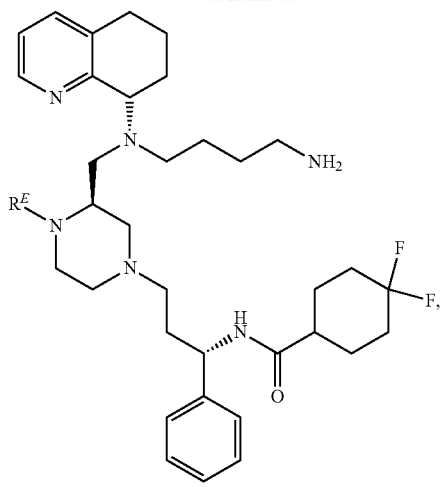

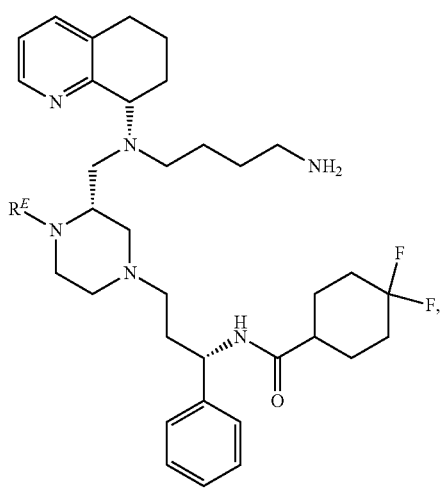

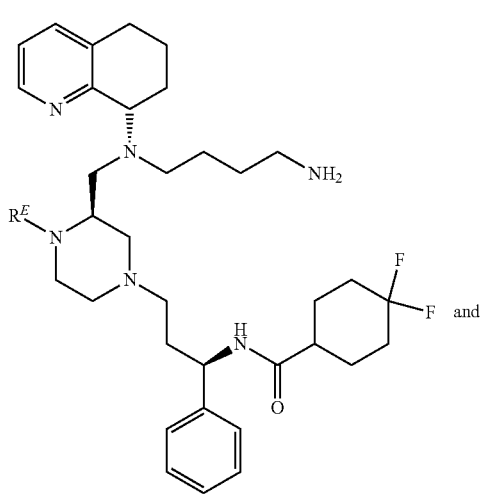

and

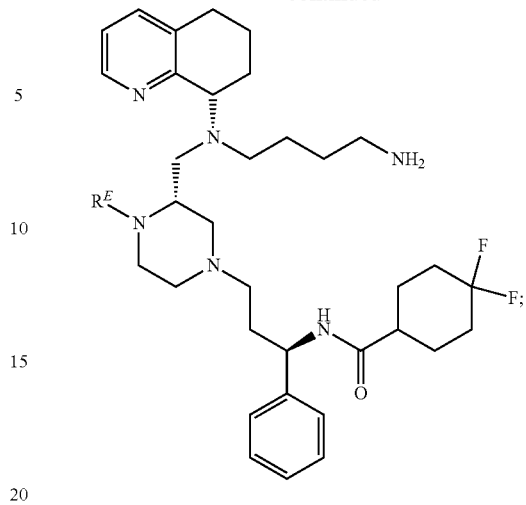

wherein $R^E$ is an optionally substituted alkyl, optionally substituted carbocycle, optionally substituted heterocarbocycle, optionally substituted aryl, or optionally substituted heteroaryl.

3. The compound of claim 2, wherein $R^E$ is selected from the group consisting of:

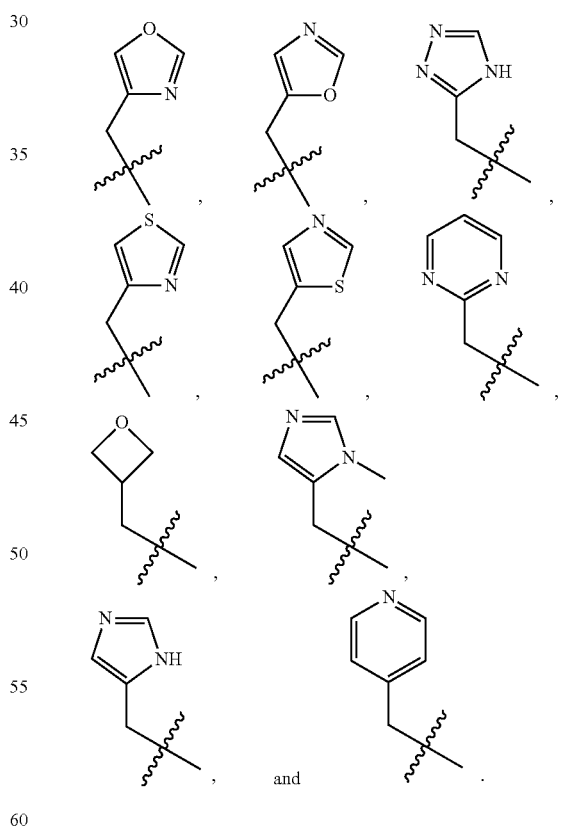

4. A pharmaceutical formulation comprising a compound of claim 1 in combination with a pharmaceutically acceptable excipient, diluent, or carrier, in the form of a tablet, pill, capsule, gel or aqueous buffered solution.

5. The pharmaceutical formulation of claim 4, further comprising an antiviral agent or chemotherapeutic agent.

6. A method of treating a viral infection, the method comprising administering a compound of claim 1 to a subject in need thereof, wherein the viral infection is an HIV infection.

7. The method of claim 6, wherein the subject is at risk of, exhibiting symptoms of, or diagnosed with the viral infection.

8. The compound of claim 2, wherein the compound has a structure of the following or a salt thereof:

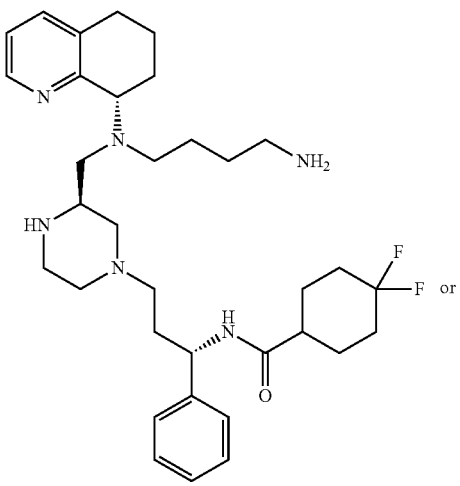

-continued

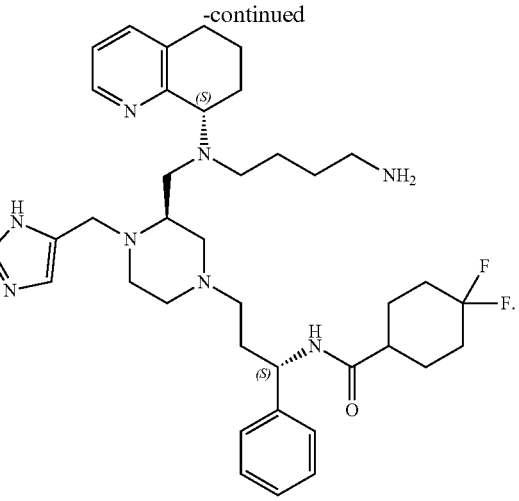

9. A pharmaceutical formulation comprising a compound of claim 2 in combination with a pharmaceutically acceptable excipient, diluent, or carrier, in the form of a tablet, pill, capsule, gel or aqueous buffered solution.

10. The pharmaceutical formulation of claim 9, further comprising an antiviral agent or chemotherapeutic agent.

11. A method of treating a viral infection, the method comprising administering a compound of claim 2 to a subject in need thereof, wherein the viral infection is an HIV infection.

12. The method of claim 11, wherein the subject is at risk of, exhibiting symptoms of, or diagnosed with the viral infection.

\* \* \* \* \*